US010959724B2

(12) United States Patent
Miller et al.

(10) Patent No.: US 10,959,724 B2
(45) Date of Patent: Mar. 30, 2021

(54) SURGICAL STAPLER WITH ROTARY CAM DRIVE AND RETURN

(71) Applicant: ETHICON LLC, Guaynabo, PR (US)

(72) Inventors: Christopher C. Miller, Loveland, OH (US); John P. Measamer, Cincinnati, OH (US); Brian F. DiNardo, Cincinnati, OH (US); Richard F. Schwemberger, Cincinnati, OH (US); Johnny H. Alexander, III, West Chester, OH (US)

(73) Assignee: Ethicon LLC, Guaynabo, PR (US)

(*) Notice: Subject to any disclaimer, the term of this patent is extended or adjusted under 35 U.S.C. 154(b) by 56 days.

(21) Appl. No.: 16/109,020

(22) Filed: Aug. 22, 2018

(65) Prior Publication Data

US 2019/0053796 A1 Feb. 21, 2019

Related U.S. Application Data

(63) Continuation of application No. 14/033,688, filed on Sep. 23, 2013, now abandoned.

(51) Int. Cl.
| | |
|---|---|
| *A61B 17/068* | (2006.01) |
| *A61B 17/115* | (2006.01) |
| *A61B 17/00* | (2006.01) |

(52) U.S. Cl.
CPC ........ *A61B 17/068* (2013.01); *A61B 17/1155* (2013.01); *A61B 2017/00199* (2013.01);
(Continued)

(58) Field of Classification Search
CPC . A61B 17/068; A61B 17/115; A61B 17/1155; A61B 2017/00199;
(Continued)

(56) References Cited

U.S. PATENT DOCUMENTS 2,211,741 A * 8/1940 Elwell .................... B25D 17/04
74/56
3,974,705 A * 8/1976 Wittkamp ................ B23B 9/00
74/53
(Continued)

FOREIGN PATENT DOCUMENTS

| EP | 1 992 296 A1 | 11/2008 |
| EP | 2 025 293 A1 | 2/2009 |

(Continued)

OTHER PUBLICATIONS

Chinese Office Action, The Second Office Action, dated Nov. 23, 2018 for Application No. CN 201480052189.7, 4 pgs.
(Continued)

*Primary Examiner* — Dariush Seif
(74) *Attorney, Agent, or Firm* — Frost Brown Todd LLC

(57) ABSTRACT

A surgical circular stapler has a body, shaft, a stapling assembly, a motor, a cam assembly, and a firing assembly. The shaft extends distally from the body. The stapling assembly is secured to a distal end of the shaft. Longitudinal translation of the firing assembly causes the stapling assembly to drive a plurality of staples in a circular array to secure two lumens of tissue together. The stapling assembly may further drive a blade to sever any excess tissue interior of the circular array of staples. The motor is operable to rotate the cam assembly. Rotation of the cam assembly causes longitudinal translation of the firing assembly. A single rotation of the cam assembly is operable to drive the firing assembly from a proximal position to a distal position and back to a proximal position.

19 Claims, 51 Drawing Sheets

(52) U.S. Cl.
CPC ........... *A61B 2017/00221* (2013.01); *A61B 2017/00367* (2013.01); *A61B 2017/00398* (2013.01)

(58) Field of Classification Search
CPC ........... A61B 2017/00221; A61B 2017/00367; A61B 2017/00398; A61B 2017/2925
USPC .................................................. 227/175.1
See application file for complete search history.

(56) References Cited

U.S. PATENT DOCUMENTS

| | | | |
|---|---|---|---|
| 4,289,041 A * | 9/1981 | Valdespino | B25F 3/00 173/121 |
| 4,644,952 A * | 2/1987 | Patipa | A61M 37/0076 173/205 |
| 4,805,823 A | 2/1989 | Rothfuss | |
| 5,205,459 A | 4/1993 | Brinkerhoff et al. | |
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,333,773 A | 8/1994 | Main et al. | |
| 5,337,623 A * | 8/1994 | Huang | B23Q 3/1554 74/53 |
| 5,350,104 A | 9/1994 | Main et al. | |
| 5,415,334 A | 5/1995 | Williamson, IV et al. | |
| 5,465,895 A | 11/1995 | Knodel et al. | |
| 5,533,661 A | 7/1996 | Main et al. | |
| 5,597,107 A | 1/1997 | Knodel et al. | |
| 5,628,446 A * | 5/1997 | Geiste | A61B 17/0684 227/175.1 |
| 5,632,432 A | 5/1997 | Schulze et al. | |
| 5,673,840 A | 10/1997 | Schulze | |
| 5,704,534 A | 1/1998 | Huitema et al. | |
| 5,814,055 A | 9/1998 | Knodel et al. | |
| 6,021,573 A * | 2/2000 | Kikuchi | B23D 49/02 30/392 |
| 6,050,472 A * | 4/2000 | Shibata | A61B 17/115 227/175.2 |
| 6,058,815 A * | 5/2000 | Habermehl | B25B 21/00 81/177.1 |
| 6,443,973 B1 * | 9/2002 | Whitman | A61B 17/07207 606/219 |
| 6,471,713 B1 * | 10/2002 | Vargas | A61B 17/11 606/153 |
| 6,698,177 B1 * | 3/2004 | Akehi | B21D 53/28 56/236 |
| 6,945,444 B2 * | 9/2005 | Gresham | A61B 17/115 227/175.1 |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,422,136 B1 | 9/2008 | Marczyk | |
| 7,434,715 B2 | 10/2008 | Shelton, IV et al. | |
| 7,556,185 B2 * | 7/2009 | Viola | A61B 17/07207 227/175.1 |
| 7,721,930 B2 | 5/2010 | McKenna et al. | |
| 7,770,775 B2 * | 8/2010 | Shelton, IV | A61B 34/76 227/178.1 |
| 7,794,475 B2 | 9/2010 | Hess et al. | |
| 7,959,050 B2 | 6/2011 | Smith et al. | |
| 8,025,199 B2 * | 9/2011 | Whitman | A61B 17/115 227/179.1 |
| 8,397,832 B2 * | 3/2013 | Blickle | B24B 23/028 173/109 |
| 8,453,914 B2 | 6/2013 | Laurent et al. | |
| 8,910,847 B2 | 12/2014 | Nalagatla et al. | |
| 9,161,803 B2 | 10/2015 | Yates et al. | |
| 9,232,945 B2 * | 1/2016 | Zingman | A61B 17/1155 |
| 9,289,207 B2 | 3/2016 | Shelton, IV | |
| 9,463,022 B2 | 10/2016 | Swayze et al. | |
| 9,498,222 B2 | 11/2016 | Scheib et al. | |
| 9,532,783 B2 | 1/2017 | Swayze et al. | |
| 9,572,573 B2 | 2/2017 | Scheib et al. | |
| 9,597,081 B2 | 3/2017 | Swayze et al. | |
| 9,724,100 B2 | 8/2017 | Scheib et al. | |
| 9,907,552 B2 | 3/2018 | Measamer et al. | |
| 2007/0175955 A1 * | 8/2007 | Shelton, IV | A61B 17/07207 227/178.1 |
| 2007/0175957 A1 * | 8/2007 | Shelton, IV | A61B 34/76 227/178.1 |
| 2009/0108048 A1 | 4/2009 | Zemlok et al. | |
| 2009/0270895 A1 * | 10/2009 | Churchill | A61B 1/303 606/170 |
| 2012/0116379 A1 * | 5/2012 | Yates | A61B 34/25 606/33 |
| 2012/0264193 A1 | 10/2012 | Kuwana et al. | |
| 2014/0158747 A1 | 6/2014 | Measamer et al. | |
| 2014/0305992 A1 * | 10/2014 | Kimsey | A61B 17/0686 227/176.1 |
| 2015/0083772 A1 * | 3/2015 | Miller | A61B 17/1155 227/175.1 |
| 2015/0083774 A1 * | 3/2015 | Measamer | A61B 17/068 227/175.1 |
| 2015/0083775 A1 * | 3/2015 | Leimbach | A61B 17/1155 227/175.1 |

FOREIGN PATENT DOCUMENTS

| | | |
|---|---|---|
| JP | 2009-045450 A | 3/2009 |
| RU | 2009105055 A | 8/2010 |
| WO | WO 03/079911 A1 | 10/2003 |

OTHER PUBLICATIONS

Chinese Search Report, First Search, dated Feb. 24, 2018 for Application No. CN 201480052189.7, 2 pgs.
European Search Report and Written Opinion dated Feb. 10, 2015 for Application No. EP 14185807.6, 8 pgs.
European Exam Report dated Feb. 29, 2016 for Application No. EP 14185807.6, 5 pgs.
European Communication, Intention to Grant, dated Mar. 30, 2017 for Application No. EP 14185807.6, 125 pgs.
International Search Report and Written Opinion dated Dec. 22, 2014 for Application No. PCT/US2014/056514, 11 pgs.
Japanese Office Action, Notification of Reasons for Refusal, and Search Report by Registered Searching Organization dated May 8, 2018 for Application No. JP 2016-544011, 21 pgs.
Japanese Office Action, Decision to Grant a Patent, dated Jul. 24, 2018 for Application No. JP 2016-544011, 3 pgs.
Brazilian Office Action dated Feb. 14, 2020 for Application No. BR112016006337-6, 4 pgs.
Indian Office Action dated Sep. 14, 2020 for Application No. IN 201617011060, 7 pgs.
Russian Office Action and Search Report dated May 14, 2018 for Application No. RU 2016115744, 9 pgs.

* cited by examiner

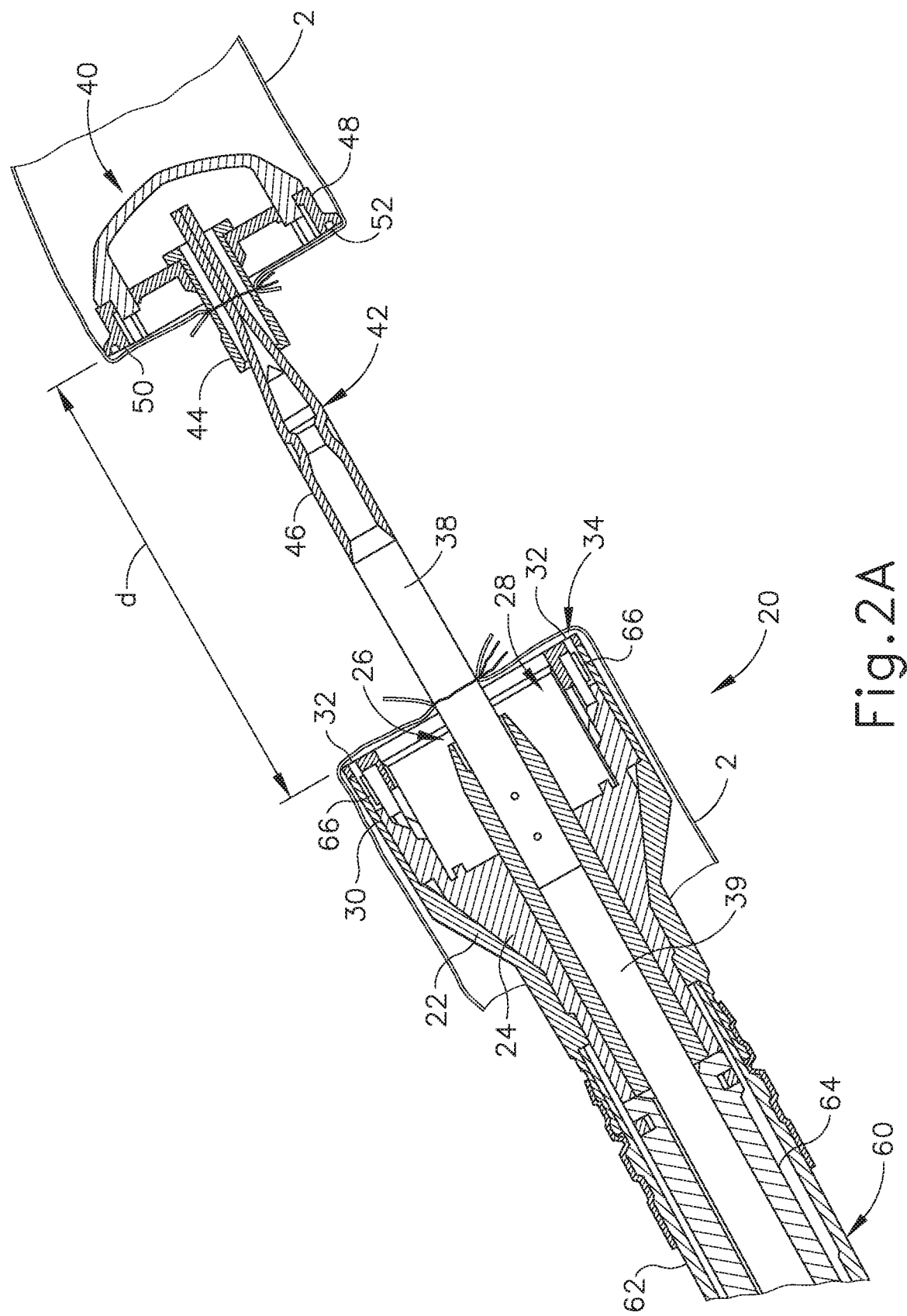

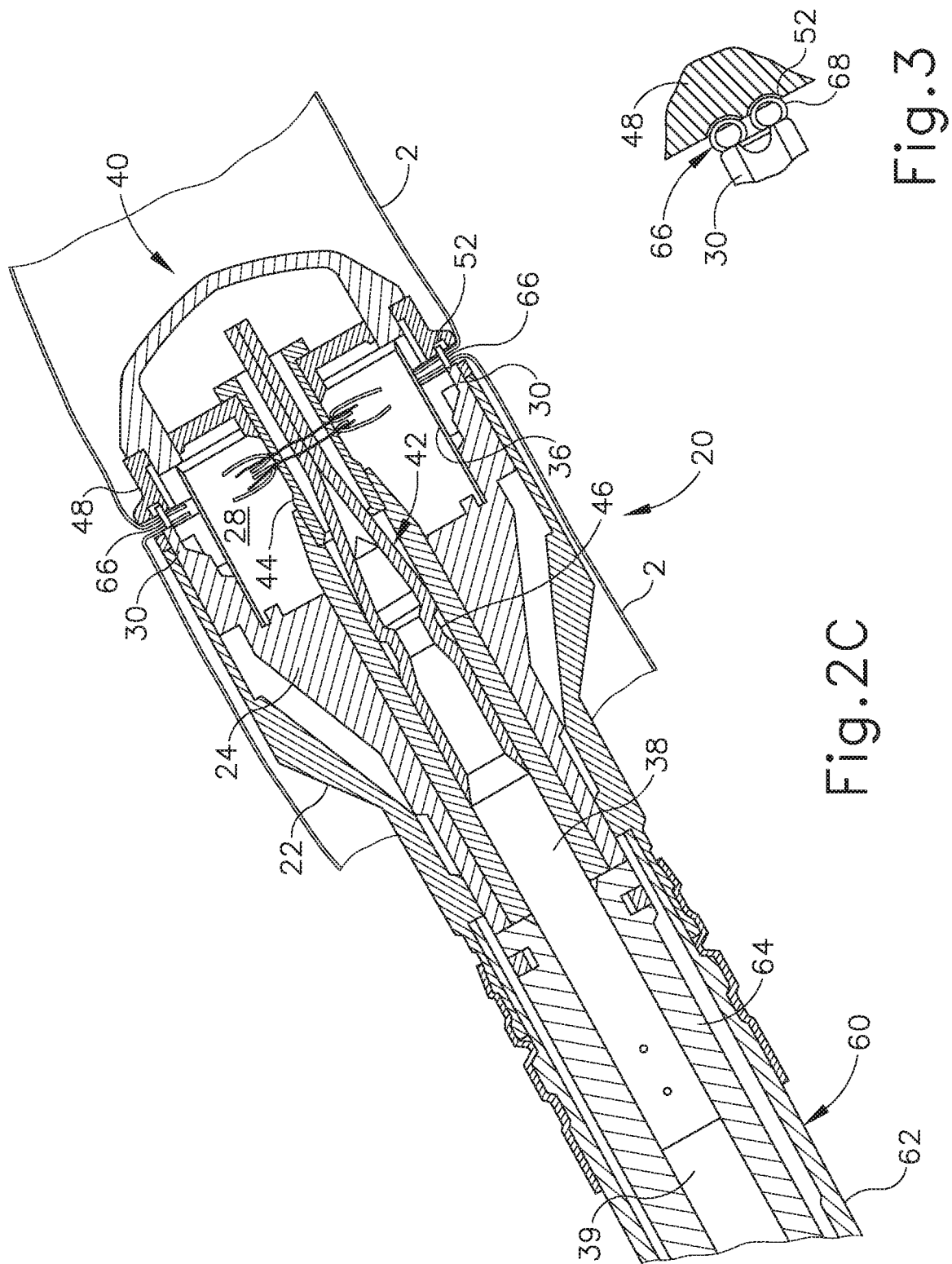

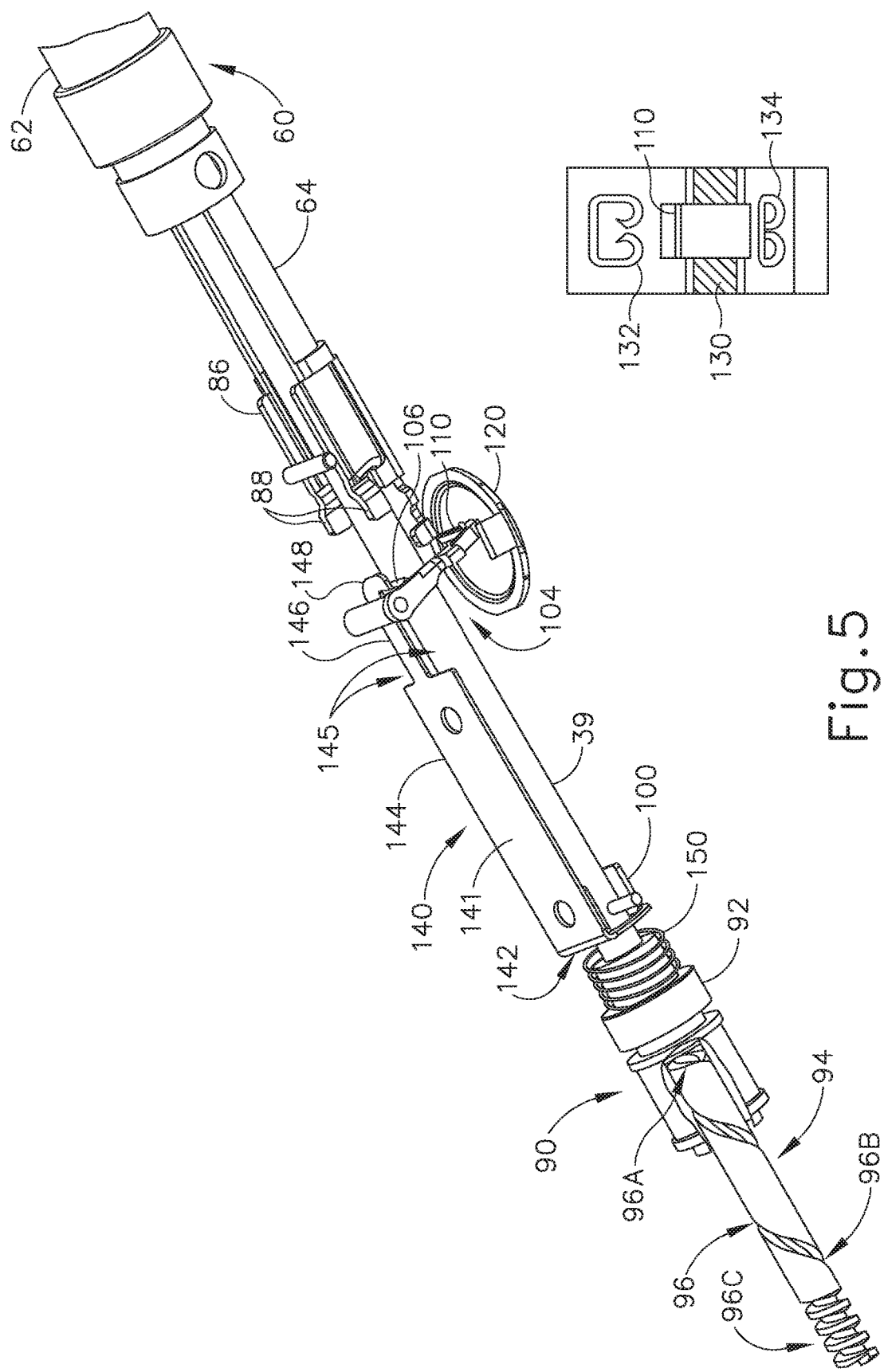

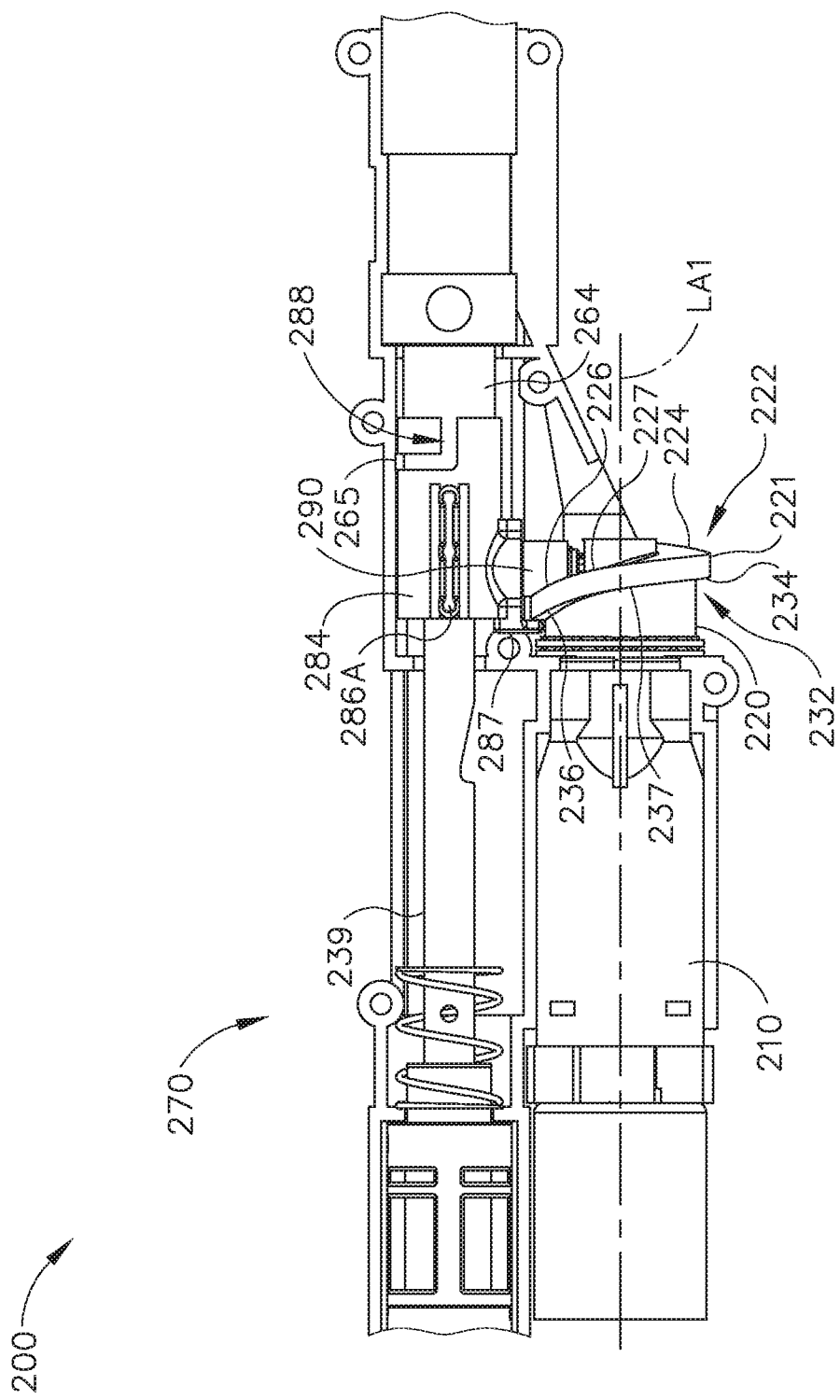

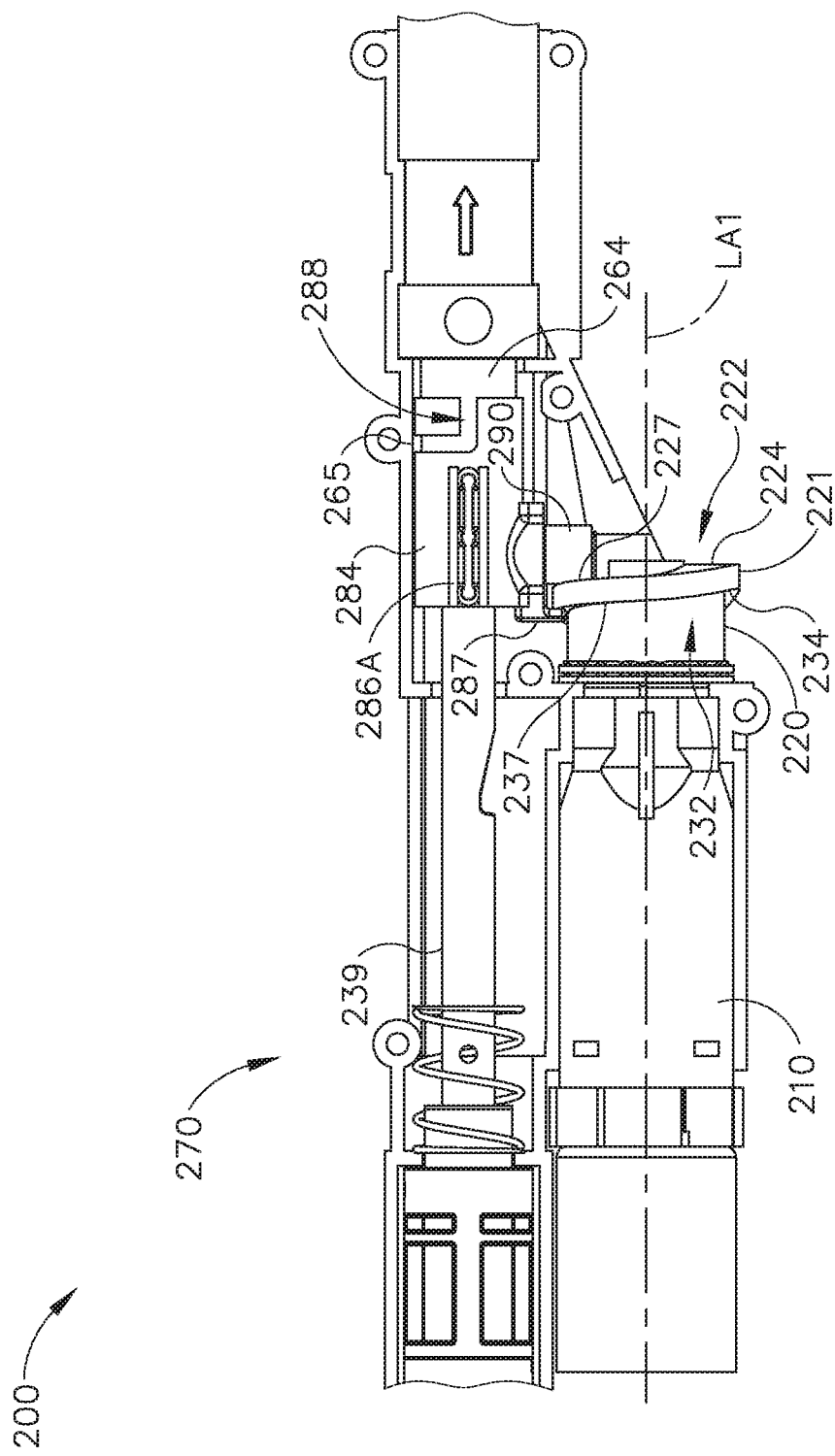

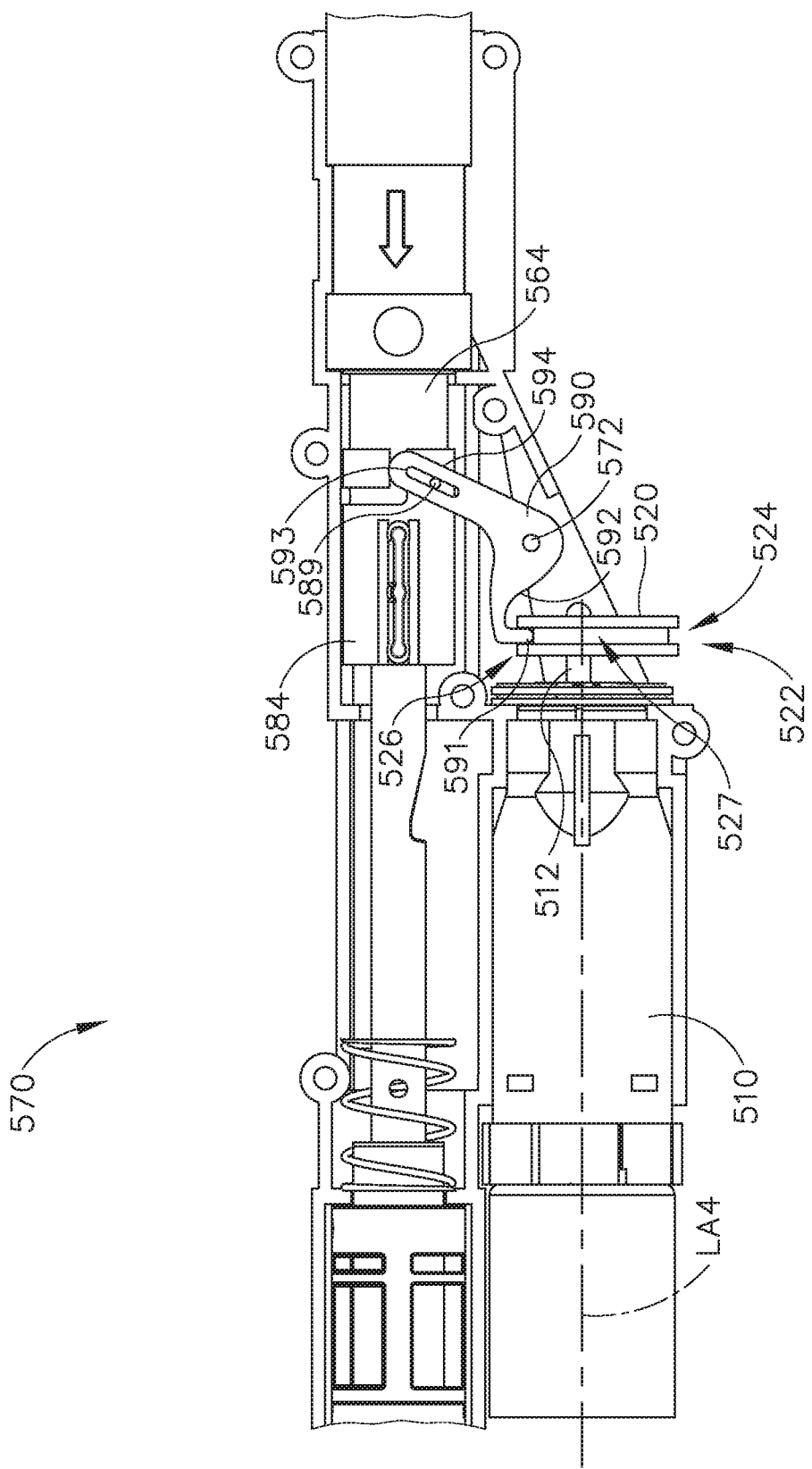

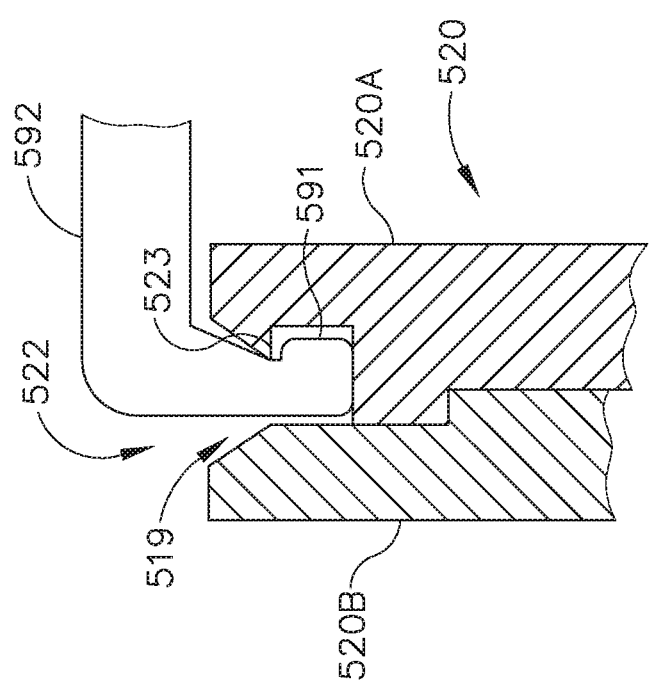

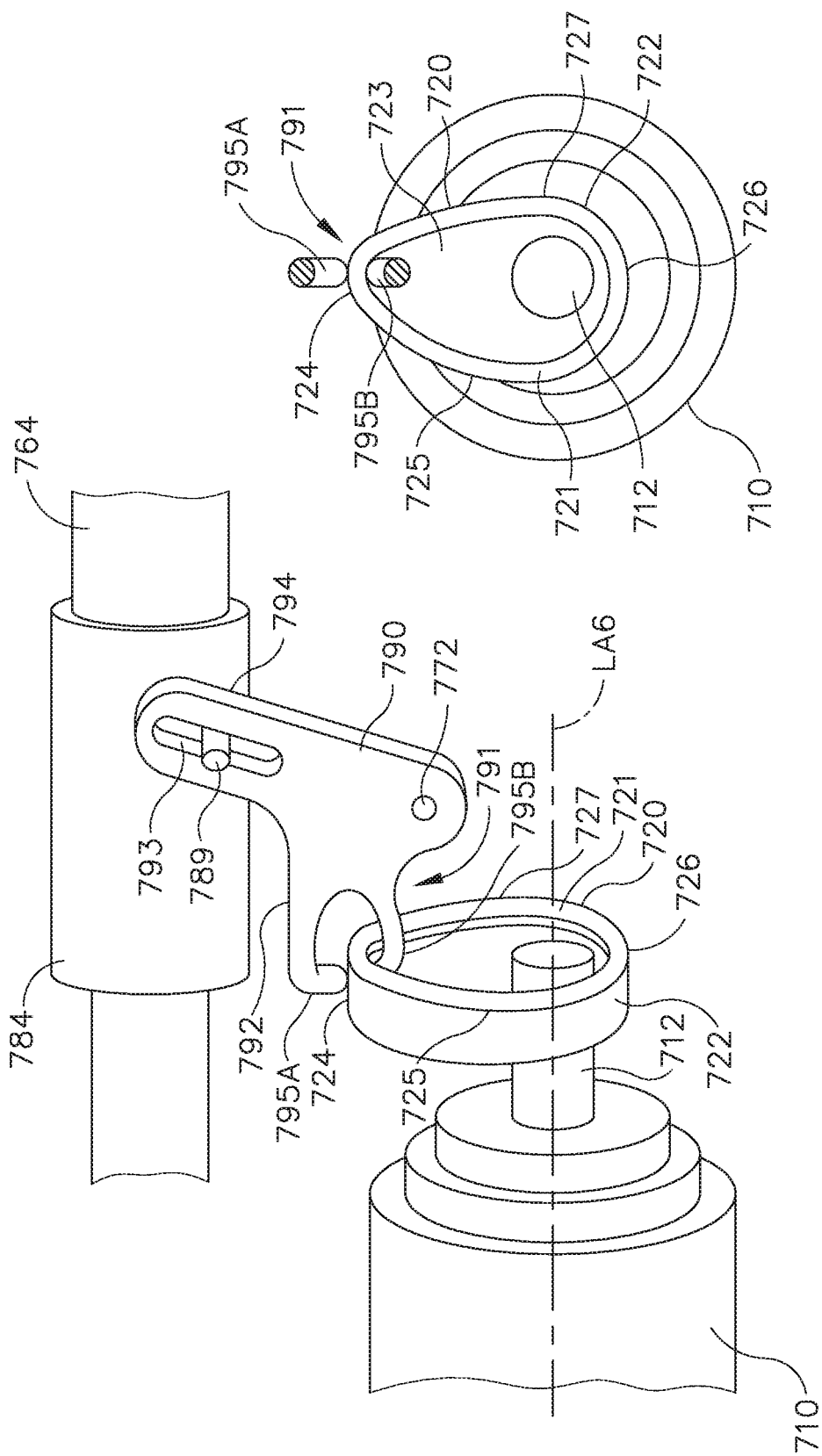

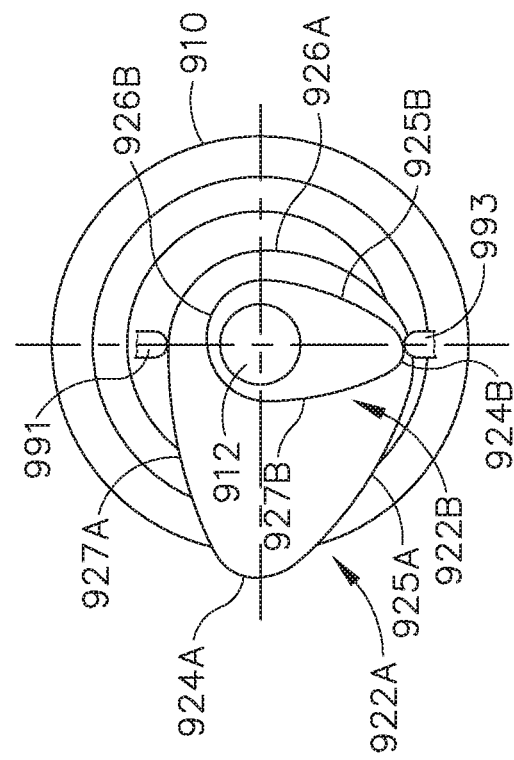
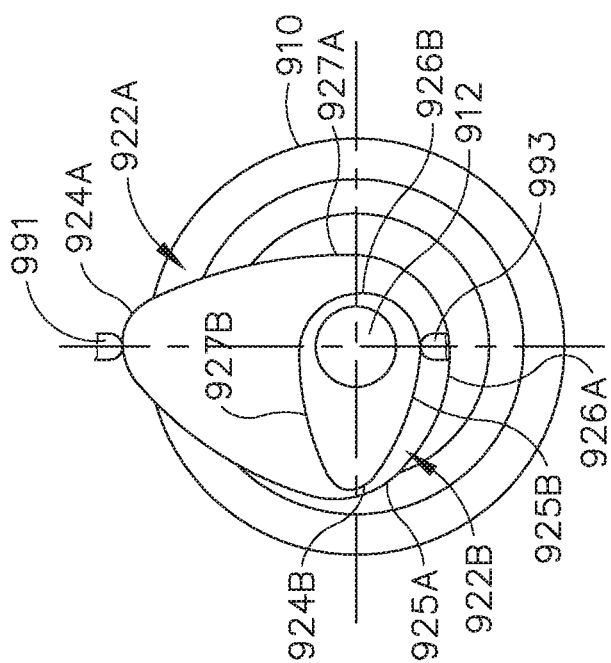
Fig.26B
Fig.26A

SURGICAL STAPLER WITH ROTARY CAM DRIVE AND RETURN

This application is a continuation of U.S. application Ser. No. 14/033,688, filed Sep. 23, 2013, published as U.S. Pub. No. 2015/0083772, entitled "Surgical Stapler with Rotary Cam Drive and Return," now abandoned.

BACKGROUND

In some settings, a surgeon may want to position a surgical instrument through an orifice of the patient and use the instrument to adjust, position, attach, and/or otherwise interact with tissue within the patient. For instance, in some surgical procedures (e.g., colorectal, bariatric, thoracic, etc.), portions of the gastrointestinal tract and/or esophagus, etc. may be cut and removed to eliminate undesirable tissue or for other reasons. Once the desired tissue is removed, the remaining portions may need to be recoupled together in an end-to-end anastomosis. One such tool for accomplishing these anastomotic procedures is a circular stapler that is inserted through a patient's naturally occurring orifice. Some circular staplers are configured to sever tissue and staple tissue substantially simultaneously. For instance, a circular stapler may sever excess tissue that is interior to an annular array of staples at an anastomosis, to provide a substantially smooth transition between lumen sections that are joined at the anastomosis.

Examples of circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pub. No. 2012/0292372, entitled "Low Cost Anvil Assembly for a Circular Stapler," published Nov. 22, 2012, now U.S. Pat. No. 8,910,847, issued Dec. 16, 2014. The disclosure of each of the above-cited U.S. Patents and U.S. Patent Application Publication is incorporated by reference herein. Some such staplers are operable to clamp down on layers of tissue, cut through the clamped layers of tissue, and drive staples through the layers of tissue to substantially seal the severed layers of tissue together near the severed ends of the tissue layers, thereby joining two severed ends of an anatomical lumen.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. Patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 2A depicts an enlarged longitudinal cross-section view of an exemplary stapling head assembly of the instrument of FIG. 1 showing an exemplary anvil in an open position;

FIG. 2C depicts an enlarged longitudinal cross-sectional view of the stapling head assembly of FIG. 2A showing an exemplary staple driver and blade in a fired position;

FIG. 3 depicts an enlarged partial cross-sectional view of an exemplary staple formed against the anvil;

FIG. 5 depicts an enlarged partial perspective view of an exemplary indicator assembly of the surgical instrument of FIG. 1 showing an indicator window and indicator lever;

FIG. 6 depicts an diagrammatic view of the indicator window of FIG. 5 showing an exemplary indicator bar and exemplary corresponding staple representations:

FIG. 11A depicts a side elevational view of the instrument of FIG. 7 with the motor and barrel cam in a first rotational position;

FIG. 11B depicts a side elevational view of the instrument of FIG. 7 with the motor and barrel cam a second rotational position;

FIG. 16E depicts a side elevational view of the instrument of FIG. 16A with the motor and cam of FIG. 14 returned to the first rotational position upon completion of a firing stroke;

FIG. 17 depicts a side cross-sectional view of an exemplary cam locking feature;

FIG. 21 depicts a perspective view of a motor and yet another exemplary alternative cam that may be incorporated into the instrument of FIG. 7;

FIG. 22 depicts a front elevational view of the motor and cam of FIG. 21;

FIG. 26A depicts a front elevational view of the motor and multi-cam shaft of FIG. 25A in the first rotational position;

FIG. 26B depicts a front elevational view of the motor and multi-cam shaft of FIG. 25A in the second rotational position;

Figure 1:
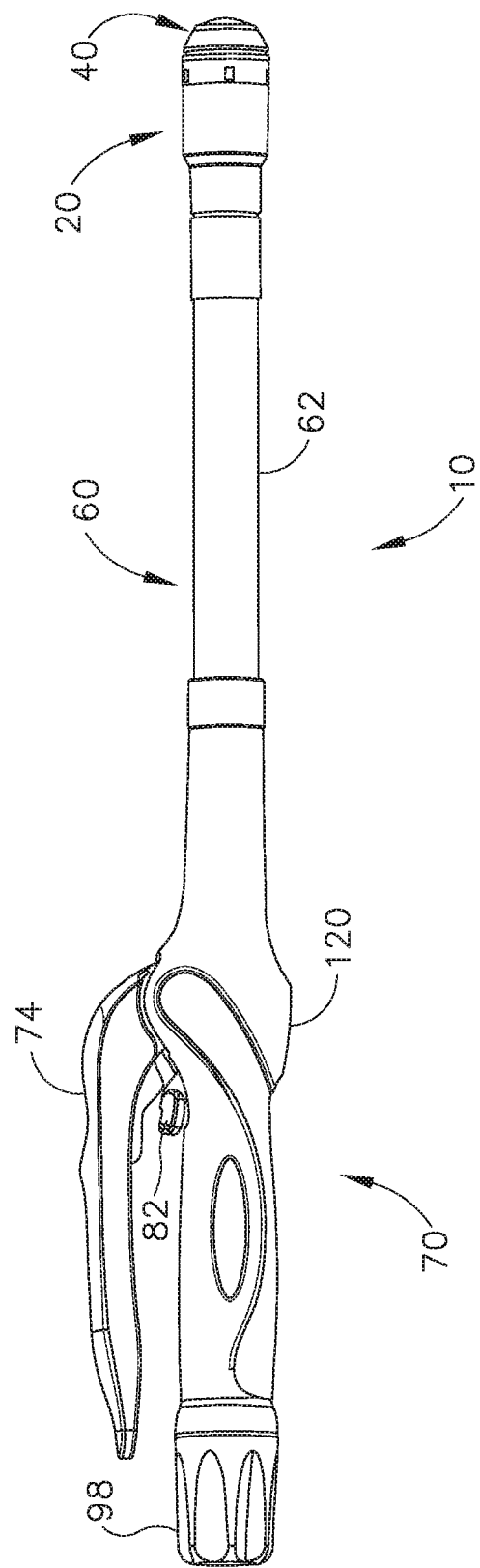
FIG. 1 depicts a side elevational view of an exemplary circular stapling surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, Which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-6 depict an exemplary circular surgical stapling instrument (10) having a stapling head assembly (20), a shaft assembly (60), and an actuator handle assembly (70), each of which will be described in more detail below. Shaft assembly (60) extends distally from actuator handle assembly (70) and stapling head assembly (20) is coupled to a distal end of shaft assembly (60). In brief, actuator handle assembly (70) is operable to actuate a staple driver (24) of stapling head assembly (20) to drive a plurality of staples (66) out of stapling head assembly (20). Staples (66) are bent to form completed staples by an anvil (40) that is attached at the distal end of instrument (10). Accordingly, tissue (2), shown in FIGS. 2A-2C, may be stapled utilizing instrument (10).

In the present example, instrument (10) comprises a closure system and a firing system. The closure system comprises a trocar (38), a trocar actuator (39), and a rotating knob (98). An anvil (40) may be coupled to a distal end of trocar (38). Rotating knob (98) is operable to longitudinally translate trocar (38) relative to stapling head assembly (20), thereby translating anvil (40) when anvil (40) is coupled to trocar (38), to clamp tissue between anvil (40) and stapling head assembly (20). The firing system comprises a trigger (74), a trigger actuation assembly (84), a driver actuator (64), and a staple driver (24). Staple driver (24) includes a knife (36) configured to sever tissue when staple driver (24) is actuated longitudinally. In addition, staples (66) are positioned distal to a plurality of staple driving features (30) of staple driver (24) such that staple driver (24) also drives staples (66) distally when staple driver (24) is actuated longitudinally. Thus, when trigger (74) is actuated and trigger actuation assembly (84) actuates staple driver (24) via driver actuator (64), knife (36) and members (30) substantially simultaneously sever tissue (2) and drive staples (66) distally relative to stapling head assembly (20) into tissue. The components and functionalities of the closure system and firing system will now be described in greater detail.

A. Exemplary Anvil

Figure 2B:
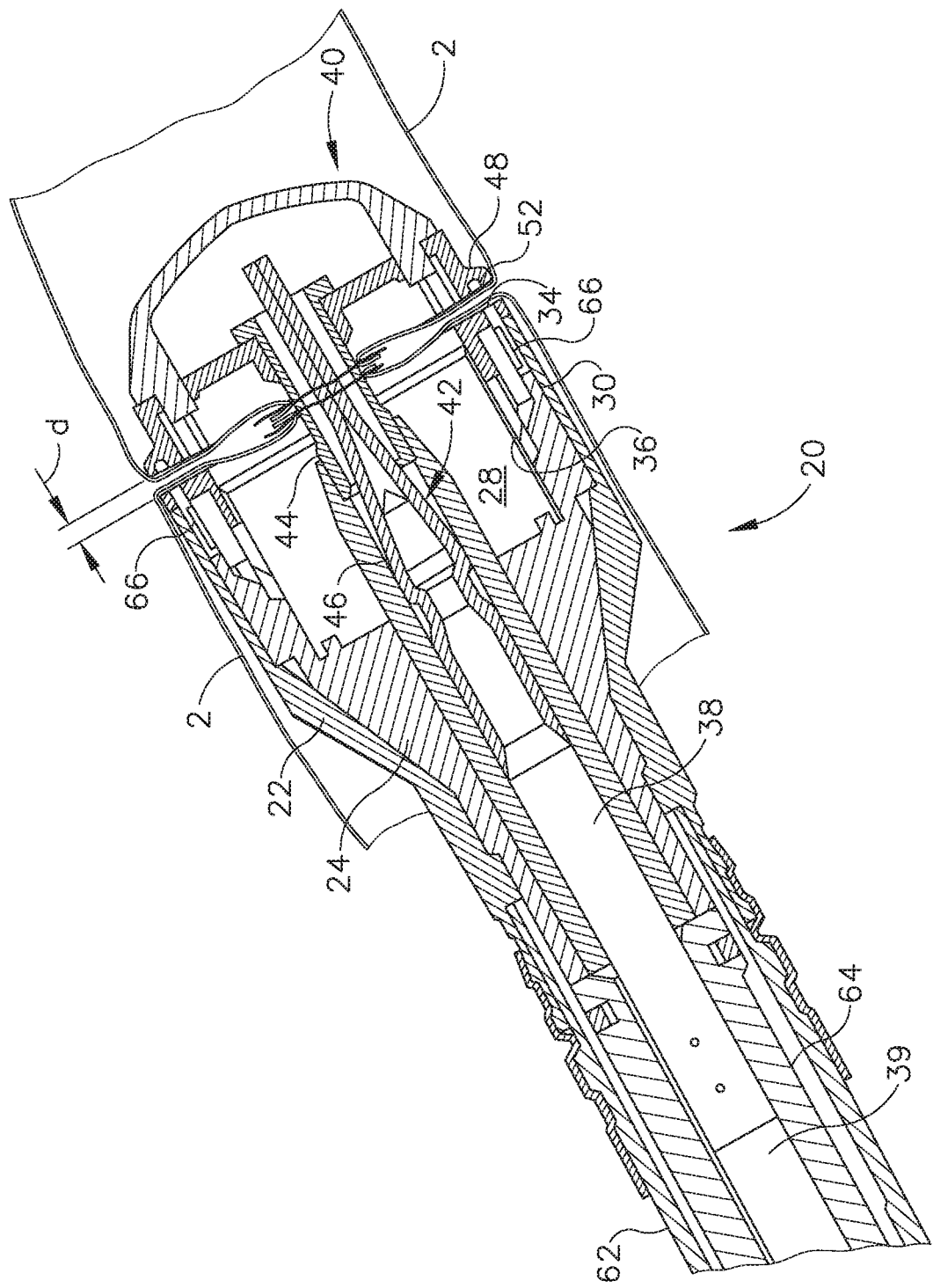
FIG. 2B depicts an enlarged longitudinal cross-sectional view of the stapling head assembly of FIG. 2A showing the anvil in a closed position.

As shown in FIGS. 1-2C, anvil (40) is selectively coupleable to instrument (10) to provide a surface against which staples (66) may be bent to staple material contained between stapling head assembly (20) and anvil (40), Anvil (40) of the present example is selectively coupleable to a trocar or pointed rod (38) that extends distally relative to stapling head assembly (20). Referring to FIGS. 2A-2C, anvil (40) is selectively coupleable via the coupling of a proximal shaft (42) of anvil (40) to a distal tip of trocar (38). Anvil (40) comprises a generally circular anvil head (48) and a proximal shaft (42) extending proximally from anvil head (48), In the example shown, proximal shaft (42) comprises a tubular member (44) having resiliently biased retaining clips (46) to selectively couple anvil (40) to trocar (38), though this is merely optional, and it should be understood that other retention features for coupling anvil (40) to trocar (38) may be used as well. For example, C-clips, clamps, threading, pins, adhesives, etc. may be employed to couple anvil (40) to trocar (38). In addition, while anvil (40) is described as selectively coupleable to trocar (38), in some versions proximal shaft (42) may include a one-way coupling feature such that anvil (40) cannot be removed from trocar (38) once anvil (40) is attached. Merely exemplary one-way features include barbs, one way snaps, collets, collars, tabs, bands, etc. Of course still other configurations for coupling anvil (40) to trocar (38) will be apparent to one of ordinary skill in the art in view of the teachings herein. For instance, trocar (38) may instead be a hollow shaft and proximal shaft (42) may comprise a sharpened rod that is insertable into the hollow shaft.

Anvil head (48) of the present example comprises a plurality of staple forming pockets (52) formed in a proximal face (50) of anvil head (48). Accordingly, when anvil (40) is in the closed position and staples (66) are driven out of stapling head assembly (20) into staple forming pockets (52), as shown in FIG. 2C, legs (68) of staples (66) are bent to form completed staples.

With anvil (40) as a separate component, it should be understood that anvil (40) may be inserted and secured to a portion of tissue (2) prior to being coupled to stapling head assembly (20). By way of example only, anvil (40) may be inserted into and secured to a first tubular portion of tissue (2) while instrument (10) is inserted into and secured to a second tubular portion of tissue (2). For instance, the first tubular portion of tissue (2) may be sutured to or about a portion of anvil (40), and the second tubular portion of tissue (2) may be sutured to or about trocar (38).

As shown in FIG. 2A, anvil (40) is then coupled to trocar (38). Trocar (38) of the present example is shown in a distal most actuated position. Such an extended position for trocar (38) may provide a larger area to which tissue (2) may be coupled prior to attachment of anvil (40). In addition, the extended position of trocar (38) may also provide for easier attachment of anvil (40) to trocar (38). Trocar (38) further includes a tapered distal tip. Such a tip may be capable of piercing through tissue and/or aiding the insertion of anvil (40) on to trocar (38), though the tapered distal tip is merely optional. For instance, in other versions trocar (38) may have a blunt tip. In addition, or in the alternative, trocar (38) may include a magnetic portion (not shown) which may attract anvil (40) towards trocar (38). Of course still further configurations and arrangements for anvil (40) and trocar (38) will be apparent to one of ordinary skill in the art in view of the teachings herein.

When anvil (40) is coupled to trocar (38), the distance between a proximal face of the anvil (40) and a distal face of stapling head assembly (20) defines a gap distance d. Trocar (38) of the present example is translatable longitudinally relative to stapling head assembly (20) via an adjustment knob (98) located at a proximal end of actuator handle assembly (70), as will be described in greater detail below.

Accordingly, when anvil (40) is coupled to trocar (38), rotation of adjustment knob (98) enlarges or reduces gap distance d by actuating anvil (40) relative to stapling head assembly (20). For instance, as shown sequentially in FIGS. 2A-2B, anvil (40) is shown actuating proximally relative to actuator handle assembly (70) from an initial, open position to a closed position, thereby reducing the gap distance d and the distance between the two portions of tissue (2) to be joined. Once the gap distance d is brought within a predetermined range, stapling head assembly (20) may be fired, as shown in FIG. 2C, to staple and sever tissue (2) between anvil (40) and stapling head assembly (20). Stapling head assembly (20) is operable to staple and sever tissue (2) by a user pivoting a trigger (74) of actuator handle assembly (70), as will be described in greater detail below.

As noted above, gap distance d corresponds to the distance between anvil (40) and stapling head assembly (20). When instrument (10) is inserted into a patient, this gap distance d may not be easily viewable. Accordingly, a moveable indicator bar (110), shown in FIGS. 5-6, is provided to be visible through an indicator window (120) positioned opposite to trigger (74). Indicator bar (110) is operable to move in response to rotation of adjustment knob (98) such that the position of indicator bar (110) is representative of the gap distance d. As shown in FIG. 6, indicator window (120) further comprises a scale (130) which indicates that the anvil gap is within a desired operating range (e.g., a green colored region or "green zone") and a corresponding staple compression representation at each end of scale (130). By way of example only, as shown in FIG. 6, a first staple image (132) depicts a large staple height while a second staple image (134) depicts a small staple height. Accordingly, a user can view the position of the coupled anvil (40) relative to the stapling head assembly (20) via indicator bar (110) and scale (130). The user may then adjust the positioning of anvil (40) via adjustment knob (98) accordingly.

Referring back to FIGS. 2A-2C, a user sutures a portion of tissue (2) about tubular member (44) such that anvil head (48) is located within a portion of the tissue (2) to be stapled. When tissue (2) is attached to anvil (40), retaining clips (46) and a portion of tubular member (44) protrude out from tissue (2) such that the user may couple anvil (40) to trocar (38). With tissue (2) coupled to trocar (38) and/or another portion of stapling head assembly (20), the user attaches anvil (40) to trocar (38) and actuates anvil (40) proximally towards stapling head assembly (20) to reduce the gap distance d. Once instrument (10) is within the operating range, the user then staples together the ends of tissue (2), thereby forming a substantially contiguous tubular portion of tissue (2).

Anvil (40) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, now U.S. Pat. No. 8,910,847, the disclosures of which are incorporated by reference herein; and/or in accordance with other configurations as will be apparent to one of ordinary skill in the art in view of the teachings herein.

B. Exemplary Stapling Head Assembly

Stapling head assembly (20) of the present example is coupled to a distal end of shaft assembly (60) and comprises a tubular casing (22) housing a slidable staple driver (24) and a plurality of staples (66) contained within staple pockets (32). Staples (66) and staple pockets (32) are disposed in a circular array about tubular casing (22). In the present example, staples (66) and staple pockets (32) are disposed in a pair of concentric annular rows of staples (66) and staple pockets (32). Staple driver (24) is operable to actuate longitudinally within tubular casing (22) in response to rotation of trigger (74) of actuator handle assembly (70), As shown in FIGS. 2A-2C, staple driver (24) comprises a flared cylindrical member having a trocar opening (26), a central recess (28), and a plurality of members (30) disposed circumferentially about central recess (28) and extending distally relative to shaft assembly (60). Each member (30) is configured to contact and engage a corresponding staple (66) of the plurality of staples (66) within staple pockets (32). Accordingly, when staple driver (24) is actuated distally relative to actuator handle assembly (70), each member (30) drives a corresponding staple (66) out of its staple pocket (32) through a staple aperture (34) formed in a distal end of tubular casing (22). Because each member (30) extends from staple driver (24), the plurality of staples (66) are driven out of stapling head assembly (20) at substantially the same time. When anvil (40) is in the closed position, staples (66) are driven into staple forming pockets (52) to bend legs (68) of the staples (66), thereby stapling the material located between anvil (40) and stapling head assembly (20). FIG. 3 depicts one merely exemplary staple (66) driven by a member (30) into a staple forming pocket (32) of anvil (40) to bend legs (68).

Staple driver (24) further includes a cylindrical knife (36) that is coaxial to trocar opening (26) and inset from staple pockets (32). In the present example, cylindrical knife (36) is disposed within central recess (28) to translate distally with staple driver (24). When anvil (40) is secured to trocar (38), as described above, anvil head (48) provides a surface against which cylindrical knife (36) cuts the material contained between anvil (40) and stapling head assembly (20). In some versions, anvil head (48) may include a recess (not shown) for cylindrical knife (36) to aid in cutting the material (e.g., by providing a cooperative shearing edge). In addition, or in the alternative, anvil head (48) may include one or more opposing cylindrical knives (not shown) offset from cylindrical knife (36) such that a scissor-type cutting action may be provided. Still other configurations will be apparent to one of ordinary skill in the art in view of the teachings herein. Stapling head assembly (20) is thus operable to both staple and cut tissue (2) substantially simultaneously in response to actuation by actuator handle assembly (70).

Of course stapling head assembly (20) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, now U.S. Pat. No. 8,910,847, the disclosures of which are incorporated by reference herein; and/or in accordance with other configurations as will be apparent to one of ordinary skill in the art in view of the teachings herein.

As noted previously, staple driver (24) includes a trocar opening (26). Trocar opening (26) is configured to permit trocar (38) to longitudinally slide relative to stapling head assembly (20) and/or shaft assembly (60). As shown in FIGS. 2A-2C, trocar (38) is coupled to a trocar actuator (39) such that trocar (38) can be actuated longitudinally via rotation of rotating knob (98), as will be described in greater detail below in reference to actuator handle assembly (70). In the present example, trocar actuator (39) comprises an elongated, relatively stiff shaft coupled to trocar (38), though this is merely optional. In some versions, actuator (39) may comprise a longitudinally stiff material while permitting lateral bending such that portions of instrument (10) may be selectively bent or curved during use; or instrument (10) may include a preset bent shaft assembly (60). When anvil (40) is coupled to trocar (38), trocar (38) and anvil (40) are translatable via actuator (39) to adjust the gap distance d between anvil (40) and stapling head assembly (20). Still further configurations for actuator (39) to longitudinally actuate trocar (38) will be apparent to one of ordinary skill in the art in view of the teachings herein.

C. Exemplary Shaft Assembly

Stapling head assembly (20) and trocar (38) are positioned at a distal end of shaft assembly (60), as shown in FIGS. 2A-2C. Shaft assembly (60) of the present example comprises an outer tubular member (62) and a driver actuator (64). Outer tubular member (62) is coupled to tubular casing (22) of stapling head assembly (20) and to a body (72) of actuator handle assembly (70), thereby providing a mechanical ground for the actuating components therein. The proximal end of driver actuator (64) is coupled to a trigger actuation assembly (84) of actuator handle assembly (70), described below. The distal end of driver actuator (64) is coupled to staple driver (24) such that the rotation of trigger (74) longitudinally actuates staple driver (24). As shown in FIGS. 2A-2C, driver actuator (64) comprises a tubular member having an open longitudinal axis such that actuator (39) coupled to trocar (38) may actuate longitudinally within and relative to driver actuator (64). Of course it should be understood that other components may be disposed within driver actuator (64) as will be apparent to one of ordinary skill in the art in view of the teachings herein.

Shaft assembly (60) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, now U.S. Pat. No. 8,910,847, the disclosures of which are incorporated by reference herein; and/or in accordance with other configurations as will be apparent to one of ordinary skill in the art in view of the teachings herein.

D. Exemplary Actuator Handle Assembly

Figure 4A:
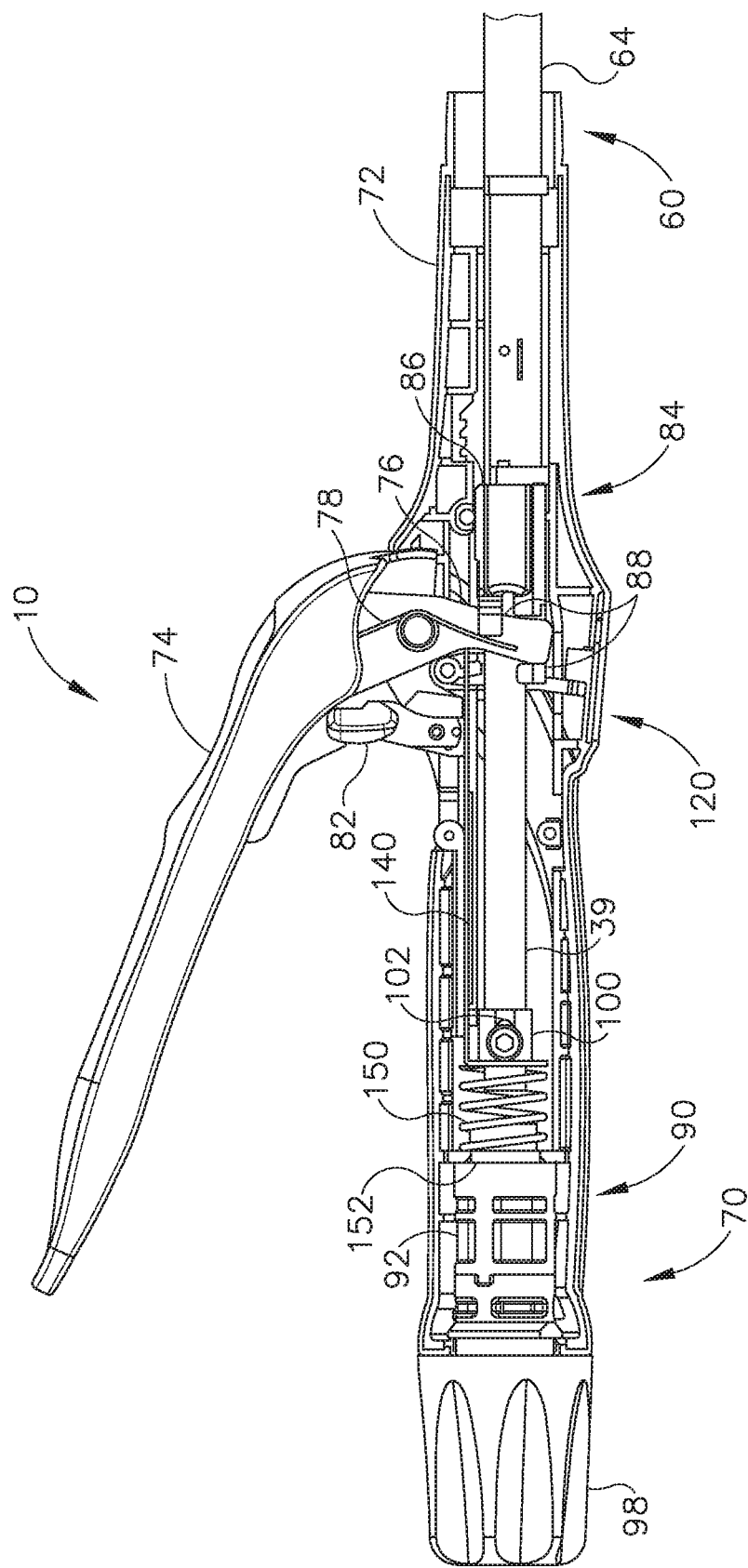
FIG. 4A depicts an enlarged side elevation view of an exemplary actuator handle assembly of the surgical instrument of FIG. 1 with a portion of the body removed, showing a trigger in an unfired position and a lockout feature in a locked position.
Figure 4B:
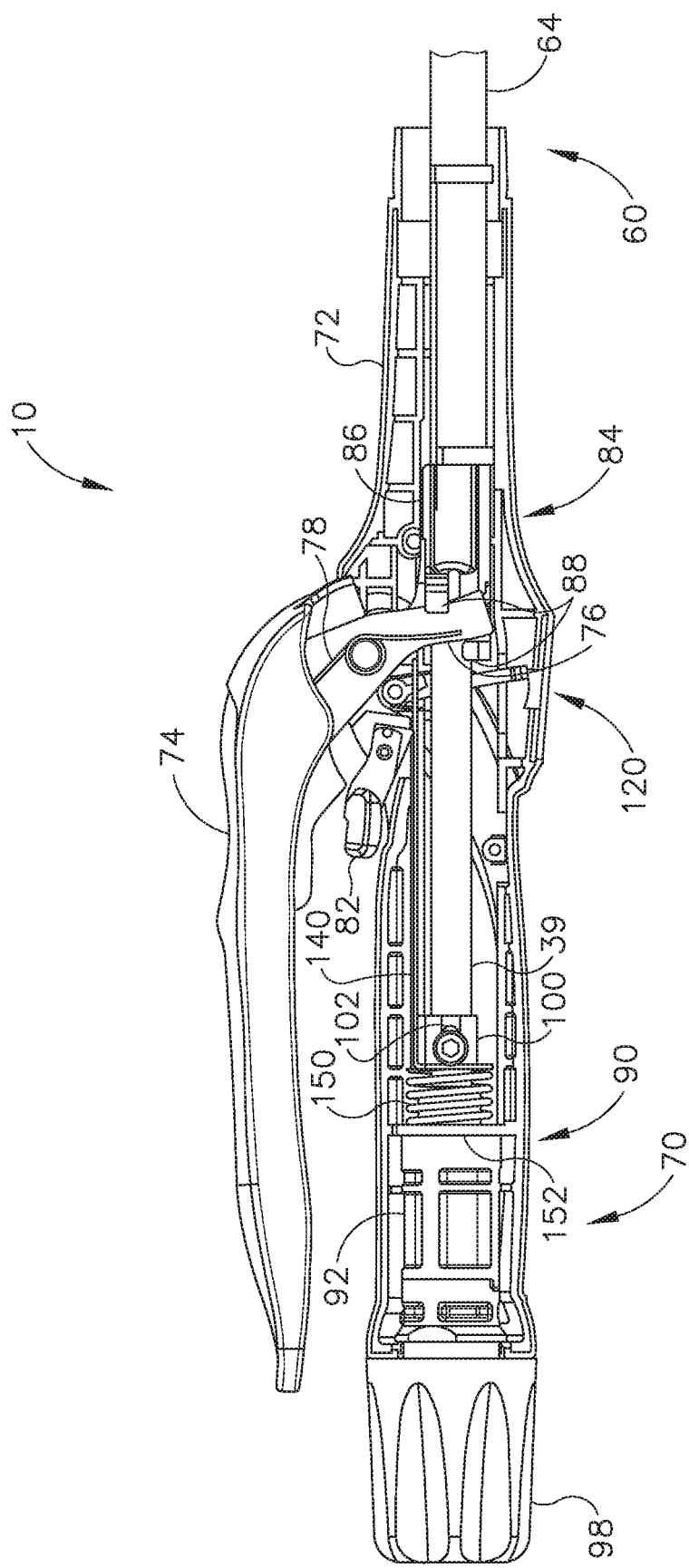
FIG. 4B depicts an enlarged side elevation view of the actuator handle assembly of FIG. 4A, showing the trigger in a fired position and the lockout feature in an unlocked position.

Referring now to FIGS. 4A-5, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 4A) to a fired position (shown in FIG. 4B) actuates driver actuator (64) described above. A spring (78) is coupled to body (72) and trigger (74) to bias trigger (74) towards the unfired position. Lockout feature (82) is a pivotable member that is coupled to body (72). In a first, locked position, lockout feature (82) is pivoted upwards and away from body (72) such that lockout feature (82) engages trigger (74) and mechanically resists actuation of trigger (74) by a user. In a second, unlocked position, such as that shown in FIGS. 1 and 4B, lockout feature (82) is pivoted downward such that trigger (74) may be actuated by the user. Accordingly, with lockout feature (82) in the second position, trigger (74) can engage a trigger actuation assembly (84) to tire instrument (10).

As shown in FIGS. 4A-4B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, now U.S. Pat. No. 8,910,847, the disclosures of which are incorporated by reference herein; and/or in accordance with other configurations as will be apparent to one of ordinary skill in the art in view of the teachings herein.

Body (72) also houses a trocar actuation assembly (90) configured to actuate trocar (38) longitudinally in response to rotation of adjustment knob (98). As best shown in FIGS. 4A-5, trocar actuation assembly (90) of the present example comprises adjustment knob (98), a grooved shank (94), and a sleeve (92). Grooved shank (94) of the present example is located at a proximal end of trocar actuator (39), though it should be understood that grooved shank (94) and trocar actuator (39) may alternatively be separate components that engage to transmit longitudinal movement. While grooved shank (94) is configured to translate within body (72), grooved shank (94) does not rotate within body (72). Adjustment knob (98) is rotatably supported by the proximal end of body (72) and is operable to rotate sleeve (92), which is engaged with grooved shank (94) via an internal tab (not shown). Adjustment knob (98) also defines internal threading (not shown) as will be described in greater detail below. Grooved shank (94) of the present example comprises a continuous groove (96) formed in the outer surface of grooved shank (94). Accordingly, when adjustment knob (98) is rotated, the internal tab of sleeve (92) rides within groove (96) and grooved shank (94) is longitudinally actuated relative to sleeve (92). Since grooved shank (94) is located at the proximal end of trocar actuator (39), rotating adjustment knob (98) in a first direction advances trocar actuator (39) distally relative to actuator handle assembly (70). Accordingly, the gap distance d between anvil (40) and stapling head assembly (20) is increased. By rotating adjustment knob (98) in the opposite direction, trocar actuator (39) is actuated proximally relative to actuator handle assembly (70) to reduce the gap distance d between anvil (40) and stapling head assembly (20). Titus, trocar actuation assembly (90) is operable to actuate trocar (38) in response to rotating adjustment knob (98). Of course other configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial length of grooved shank (94). Middle portion (96B) comprises a section with comparably coarser pitch or fewer grooves per axial length such that relatively few rotations are required for the internal tab of sleeve (92) to traverse a long axial distance. When anvil (40) is in an initial, distal position in relation to stapling head assembly (20), the internal tab of sleeve (92) is positioned in middle portion (96B). Accordingly, the gap distance d may be quickly reduced through relatively few rotations of adjustment knob (98) while the internal tab of sleeve (92) traverses middle portion (96B). Proximal portion (96C) of the present example is substantially similar to distal portion (96A) and comprises a fine pitch or a high number of grooves over a short axial distance of grooved shank (94) such that a large number of rotations are required to traverse the short axial distance. Proximal portion (96C) of the present example is engaged by the internal threading defined by knob (98) when anvil (40) is substantially near to stapling head assembly (20), such that indicator bar (110) moves within indicator window (120) along scale (130) to indicate that the anvil gap is within a desired operating range, as will be described in more detail below. Accordingly, when grooved shank (94) reaches a proximal position where the proximal portion (96C) of groove (96) engages the internal threading of knob (98), each rotation of adjustment knob (98) may reduce the gap distance d by a relatively small amount to provide for fine tuning. It should be understood that the internal tab of sleeve (92) may be disengaged from groove (96) when proximal portion (96C) is engaged with the internal threading of knob (98).

Trocar actuation assembly (90) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

In the example shown in FIGS. 4A-4B, a U-shaped clip (100) is attached to an intermediate portion of trocar actuator (39) located distally of grooved shank (94). In the present example, an extension of trocar actuator (39) engages a slot in the housing of handle assembly (70) to prevent trocar actuator (39) from rotating about its axis when adjustment knob (98) is rotated. U-shaped clip (100) of the present example further includes an elongated slot (102) on each of its opposite sides for receiving an attachment member, such as a screw, bolt, pin, etc., to selectively adjust the longitudinal position of elongated slot (102) of U-shaped clip (100) relative to trocar actuator (39) for purposes of calibrating indicator bar (110) relative to scale (130). In some versions, the attachment member (e.g., screw, bolt, pin, etc.) engages with a portion of body (72) to substantially prevent trocar actuator (39) from rotating about its axis when adjustment knob (98) is rotated.

As shown in FIG. 5, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (39) and/or grooved shank (94). A coil spring (150) is interposed between flange (142) and a boss (152) to bias flange (142) against U-shaped clip (100). Accordingly, when U-shaped clip (100) actuates distally with trocar actuator (39) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (39) and/or grooved shank (94) translate proximally, thereby compressing coil spring (150). Of course, it should be understood that in some versions indicator bracket (140) may be fixedly attached to trocar actuator (39) and/or grooved shank (94).

In the present example, a portion of lockout feature (82) abuts a surface (141) of indicator bracket (140) when indicator bracket (140) is in a longitudinal position that does not correspond to when the anvil gap is within a desired operating range (e.g., a green colored region or "green zone"). When the anvil gap is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Of course it should be understood that lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between anvil (40) and stapling head assembly (20).

Of course indicator bracket (140), indicator (104), and/or actuator handle assembly (70) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, now U.S. Pat. No. 8,910,847, the disclosures of which are incorporated by reference herein; and/or in accordance with other configurations as will be apparent to one of ordinary skill in the art in view of the teachings herein.

II. Exemplary Motorized Circular Surgical Stapling Instrument

In some instances, it may be desirable to drive staples (66) and knife (36) in a way that avoids manually driving circular surgical stapling instrument (10). For instance, in the event that the operator has inadequate hand strength to actuate circular surgical stapling instrument (10), it may be desirable to provide a motorized assembly for staple driver (24) and knife (36). Motorizing at least part of instrument (10) may also reduce the risk of operator error in driving staple driver (24) and knife (36). In some cases, operator error with a manually driven instrument (10) may result in instrument (10) failing to actuate fully. This may occur when an operator fails to fully manually actuate trigger (74), which may result in staples (66) not fully forming and thus not fully securing an anastomsis. Thus, motorizing the driving of staple driver (24) and knife (36) may ensure that knife (36) is fully driven to cut tissue, and that staples (66) are fully deployed to fasten tissue, in a single drive stroke. Various examples of how instrument (10) may be reconfigured to incorporate a motor will be described in greater detail below; while other examples will be apparent to those of ordinary skill in the art according to the teachings herein. It should be understood that the examples described below may function substantially similar to instrument (10) described above. In particular, the circular surgical stapling instruments described below may be used to staple tissue in an annular array and sever excess tissue that is interior to the annular array of staples to provide a substantially smooth transition between lumen sections.

While it may be desirable to at least partially motorize circular surgical stapling instrument (10), it may not necessarily be desirable to motorize all portions of circular surgical stapling instrument (10). For instance, it may be desirable to maintain manual adjustment of knob (98) or a similar feature to control the distance d between anvil (40) and stapling head assembly (20). Other suitable portions of circular surgical stapling instrument (10) may also rely on manual actuation despite motorization of other features, as will be apparent to one of ordinary skill in the art in view of the teachings herein.

Figure 7:
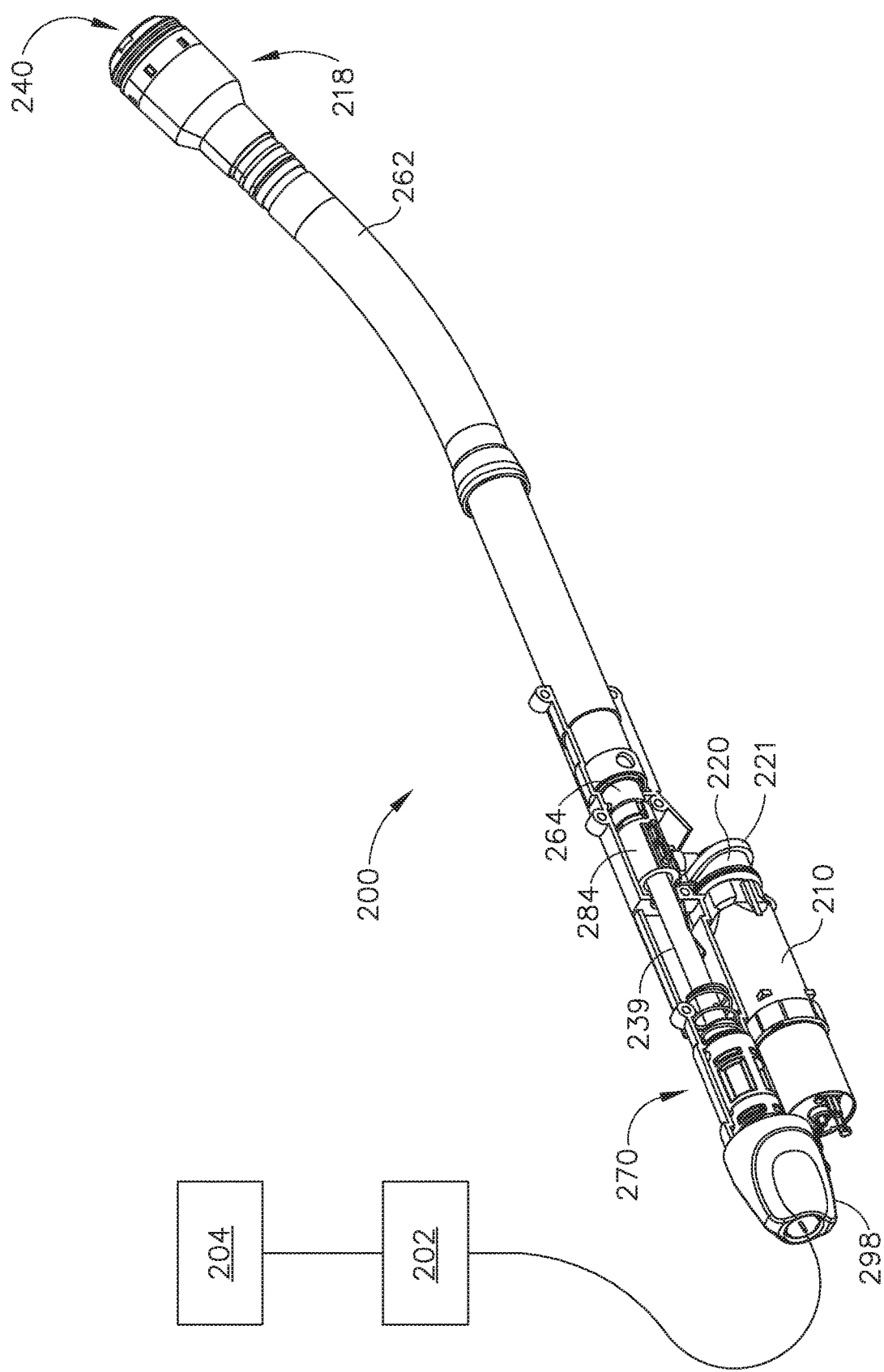
FIG. 7 depicts a perspective view of an exemplary alternative circular stapling surgical instrument having a motor and exemplary barrel cam.

One merely exemplary variation of a motorized circular surgical stapling instrument (200) is shown in FIG. 7. Instrument (200) of the present example comprises a closure system and a firing system. The closure system of the present example comprises a rotating knob (298), which is operable to drive an anvil (240). Closure system and rotating knob (298) of the present example function substantially similar to the closure system and knob (98) of instrument (10) described above. In particular, rotating knob (298) of the closure system of the present example may be rotated to longitudinally actuate a trocar actuator (239) to enlarge or reduce a gap distance between a proximal face of an anvil (240) and a distal face of a stapling head assembly (218).

The firing system of the present example functions substantially similar to the firing system of instrument (10) described above except for the differences discussed below. In particular, the firing system of the present example may be used to actuate a staple driver (not shown). The firing system of the present example comprises a motor (210), a cam follower body (284), a driver actuator (264), and the staple driver. As will be discussed in more detail below, motor (210) is configured to actuate the staple driver. Driver actuator (264) of the present example is configured to operate substantially similar to driver actuator (64) of instrument (10) discussed above. In particular, a distal end of driver actuator (264) is coupled to the staple driver such that actuation of motor (210) longitudinally translates driver actuator (264), which in turn longitudinally actuates the staple driver. The staple driver includes a plurality of staple driving features, a plurality of staples, and a knife configured to sever tissue when the staple driver is actuated longitudinally. The staple driver of the present example functions substantially similar to staple driver (24) of instrument (10) described above except for the differences discussed below. In particular, the staple driver of the present example may be used to drive an annular array of staples into tissue and to drive a knife (not shown) to sever excess tissue that is interior to the annular array of staples to provide a substantially smooth transition between lumen sections in response to the staple driver being actuated, similar to what is shown in FIG. 2C.

Figure 8:
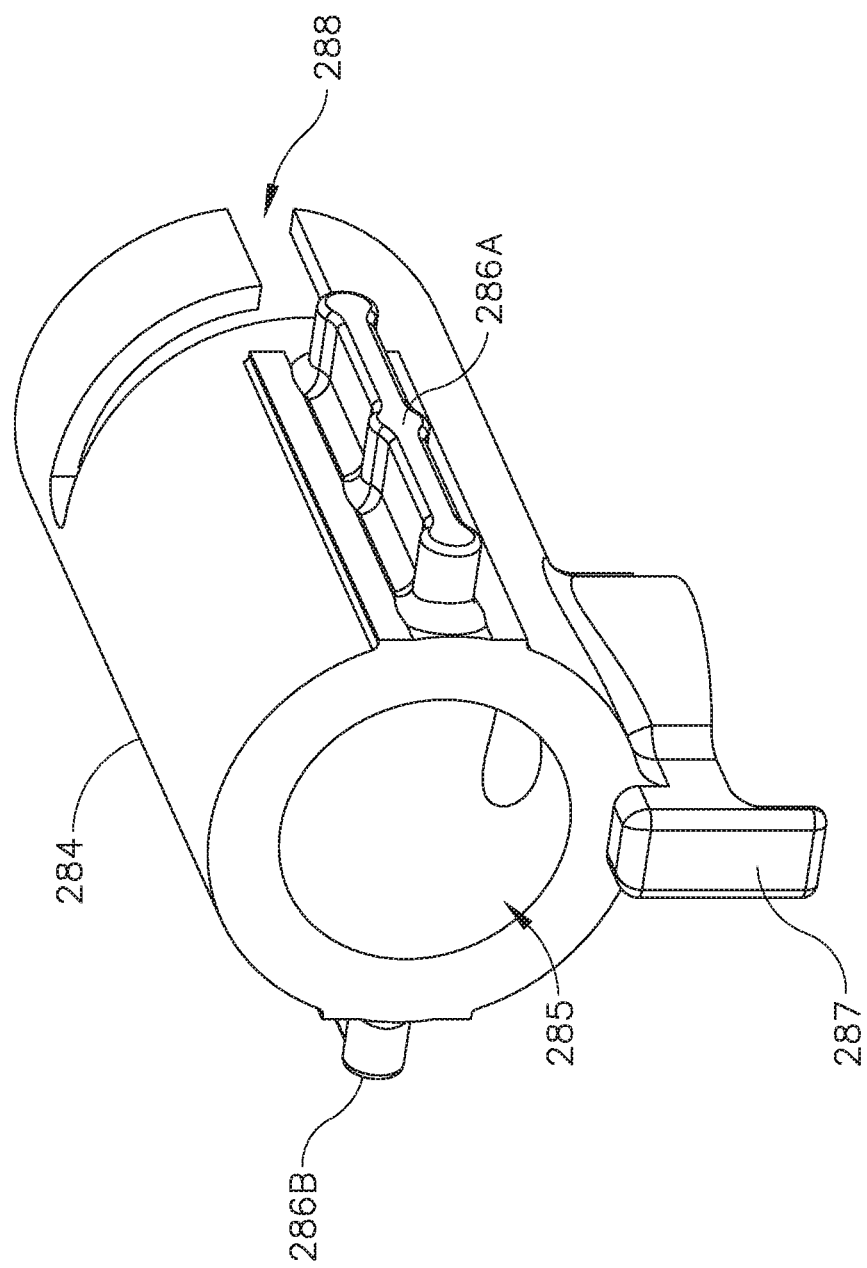
FIG. 8 depicts a perspective view of an exemplary cam follower body.
Figure 9:
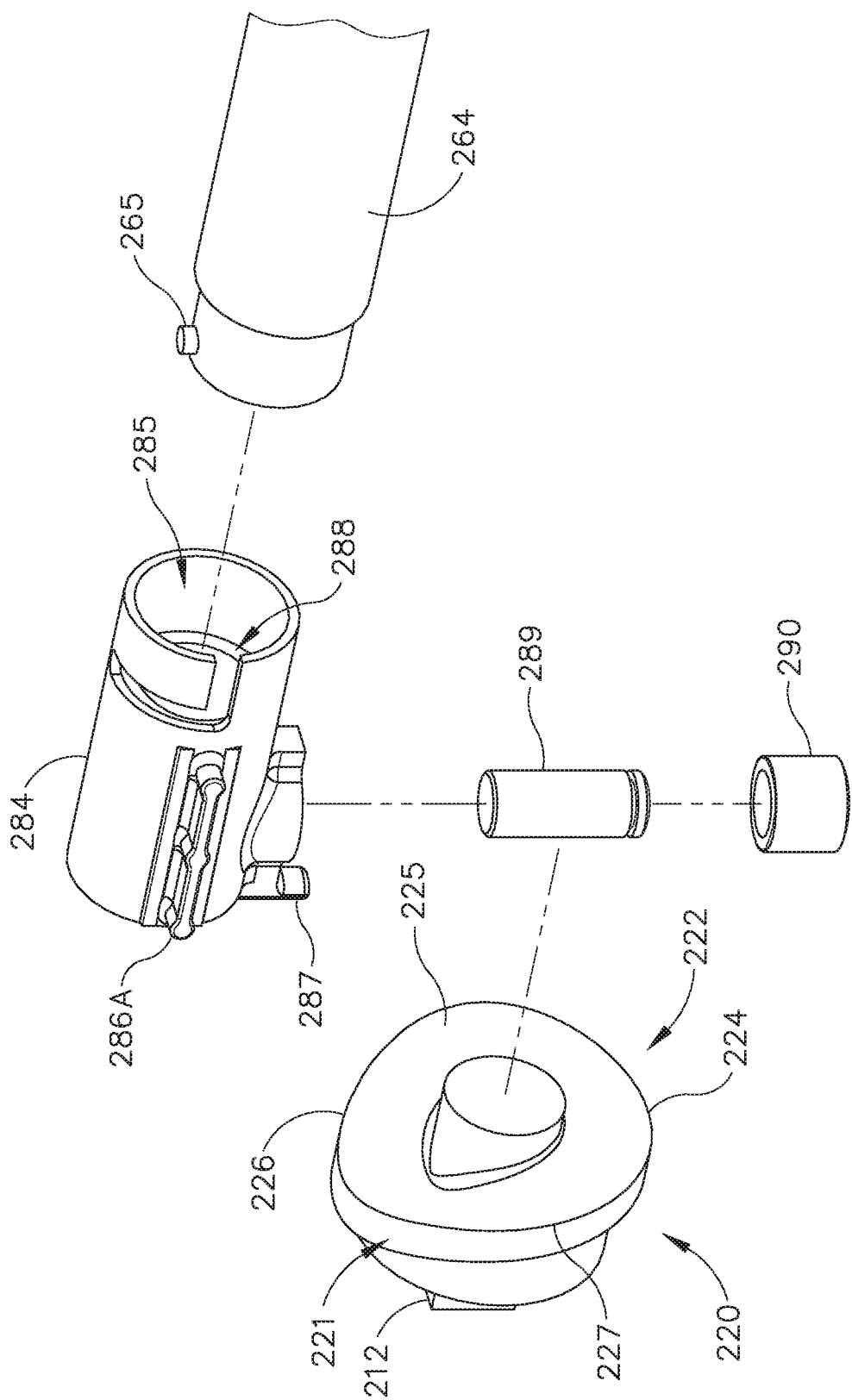
FIG. 9 depicts an exploded perspective view of a firing system, including the cam follower body of FIG. 8.

As shown in FIG. 8, cam follower body (284) comprises a pair of longitudinal projections (286A, 286B) disposed on opposite sides of cam follower body (284). Projections (286A, 286B) are slidably disposed within a pair of slots (not shown) formed in an interior surface of actuator handle assembly (270). As best seen in FIG. 9, a proximal end of driver actuator (264) comprises a radial pin (265) extending from an exterior surface of driver actuator (264). A distal end of cam follower body (284) presents a bayonet slot (288) configured to receive radial pin (265) of driver actuator (264) such that cam follower body (284) and driver actuator (264) may be coupled together and such that longitudinal translation of cam follower body (284) causes longitudinal translation of driver actuator (264). A distal end of driver actuator (264) is coupled to the staple driver such that longitudinal translation of cam follower body (284) actuates the staple driver. As will be discussed in more detail below, motor (210) is operable to cause longitudinal translation of cam follower body (284) via a cam assembly. Thus, when motor (210) is actuated and cam follower body (284) actuates the staple driver via driver actuator (264), the knife and the staple driving features substantially simultaneously sever tissue and drive staples distally into tissue.

As shown in FIGS. 7-8, trocar actuator (239) is slidably disposed within a longitudinal opening (285) formed in a cam follower body (284) such that trocar actuator (239) may translate independently relative to cam follower body (284) and vice versa. This enables operation of the closure system independently from the firing system.

Motor (210) is in communication with an operator input (202) and a power source (204). Operator input (202) may include a manually actuated trigger (e.g., similar to trigger (74), etc.) and/or some other input operable to activate motor (210). For instance, operator input (202) could include a button, trigger, lever, slider, touchpad, etc. that electrically activates motor (210). In addition or in the alternative, operator input (202) may include an electrical or software driven actuator operated by the operator to activate motor (210). In some versions, operator input (202) may include a foot actuated pedal in communication with motor (210). Other suitable forms that operator input (202) may take will be apparent to those of ordinary skill in the art in view of the teachings herein.

It will also be understood that operator input (202) may be placed in any appropriate position on or relative to circular surgical stapling instrument (10) as will be apparent to one of ordinary skill in the art in view of the teachings herein. For instance, operator input (202) may be positioned on any portion of actuator handle assembly (70) as seen in FIG. 1. Alternatively, operator input (202) may also be positioned somewhere separately from circular surgical stapling instrument (10), which may include locating operator input (202) on a separate console or computer. Operator input (202) could also be located on a console or device in wireless communication with circular surgical stapling instrument (10). Other suitable locations for operator input (202) will be apparent to those of ordinary skill in the art in view of the teachings herein.

Power source (204) may take a variety of forms. For instance, power source (204) may comprise an external source (e.g., wall outlet, etc.) coupled with instrument (10) by a cable. Power source (204) may also include a battery or battery pack (e.g., within instrument (10)) operable to deliver energy to drive assembly (200). Power source (204) in some instances may also provide a wirelessly induced energy operable to power drive assembly (200). Other suitable variations of power source (204) will be apparent to those of ordinary skill in the art in view of the teachings herein. Exemplary components and functionalities of the motor and cam assembly will now be described in greater detail.

A. First Exemplary Motor and Cam Assembly

FIGS. 7-11E show exemplary components that are incorporated into instrument (200) to actuate the staple driver and knife. In particular, a motor (210) is disposed within actuator handle assembly (270) parallel to a proximal portion of driver actuator (264). A barrel cam (220) is coupled with a distal end of motor (210) via a shaft (212). Actuation of motor (210) causes rotation of barrel cam (220) about a longitudinal axis (LA1) defined by motor (210). It should be understood that, although motor (210) of the present example is disposed within actuator handle assembly (270), motor (210) may be located externally of actuator handle assembly (270). For instance, motor (210) may be located externally of actuator handle assembly (270) and coupled with cam (220) via a flexible drive shaft.

Figure 10:
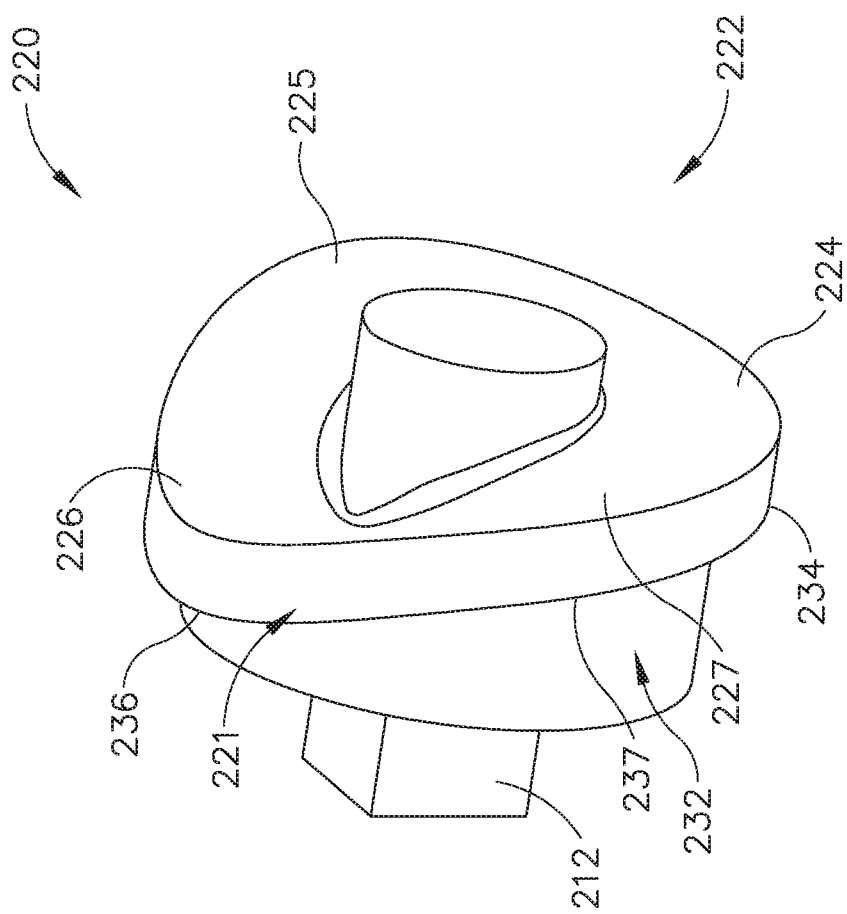
FIG. 10 depicts a perspective view of the barrel cam of FIG. 7.

As best seen in FIG. 10, barrel cam (220) comprises a lip (221) projecting from an exterior surface of barrel cam (220). Lip (221) comprises an annular sloped distal face (222). Sloped distal face (222) comprises a distal portion (224) and a proximal portion (226). Distal portion (224) and proximal portion (226) are disposed on radially opposite sides of barrel cam (220), Distal portion (224) presents a portion of sloped distal face (222) having a longitudinal position relative to longitudinal axis (LA1) more distal than that of proximal portion (226). Sloped distal face (222) further comprises intermediate portions (225, 227) disposed between distal portion (224) and proximal portion (226). Intermediate portions (225, 227) are contoured to provide a substantially smooth transition between distal portion (224) and proximal portion (226) along opposite sides of barrel cam (220). Thus, relative to a fixed point in space, the longitudinal position of sloped distal face (222) will change from the proximal position presented by proximal portion (226) to the distal position presented by distal portion (224); and back again as barrel cam (220) is rotated through one revolution.

As shown in FIG. 10, lip (221) further comprises an annular sloped proximal face (232). Sloped proximal face (232) and sloped distal face (222) have parallel contours. Sloped proximal face (232) comprises a distal portion (234) and a proximal portion (236). Distal portion (234) and proximal portion (236) are disposed on radially opposite sides of barrel cam (220). Distal portion (234) presents a portion of sloped proximal face (232) having a longitudinal position relative to longitudinal axis (LA1) more distal than that of proximal portion (236). Sloped proximal face (232) further comprises intermediate portions (235, 237) disposed between distal portion (234) and proximal portion (236). Intermediate portions (235, 237) are contoured to provide a substantially smooth transition between distal portion (234) and proximal portion (236) along opposite sides of barrel cam (220). Thus, it should be understood that, relative to a fixed point in space, the longitudinal position of sloped proximal face (232) will change from the proximal position presented by proximal portion (236) to the distal position presented by distal portion (234); and back again as barrel cam (220) is rotated through one revolution.

As shown in FIG. 9, cam follower body (284) is coupled to a pin (289) and a roller (290). Pin (289) is coupled to and extends from a bottom of cam follower body (284) such that longitudinal translation of pin (289) causes longitudinal translation of cam follower body (284). Roller (290) is rotatably coupled to pin (289) such that roller (290) freely rotates about pin (289). As will be discussed in more detail below, roller (290) is in contact with sloped distal face (222) during operation of instrument (200). As shown in FIGS. 8-9, cam follower body (284) further comprises a cam follower arm (287). As will also be discussed in more detail below, cam follower arm (287) is in contact with sloped proximal face (232) during operation of instrument (200). It should therefore be understood that lip (221) is slidably disposed between roller (290) and cam follower arm (287). Contact between cam follower arm (287) and sloped proximal face (232) is configured to cause roller (290) to remain in contact with sloped distal face (222) as barrel cam (220) rotates. Thus, it should be understood that as barrel cam (220) is rotated through one revolution, the longitudinal position of cam follower body (284) will translate from a proximal position caused by contact between roller (290) and proximal portion (226) of sloped distal face (222) to a distal position caused by contact between roller (290) and distal portion (224) of sloped distal face (222); and then back to the proximal position due to contact between cam follower arm (287) and proximal portion (236) of sloped proximal face (232).

Figure 11C:
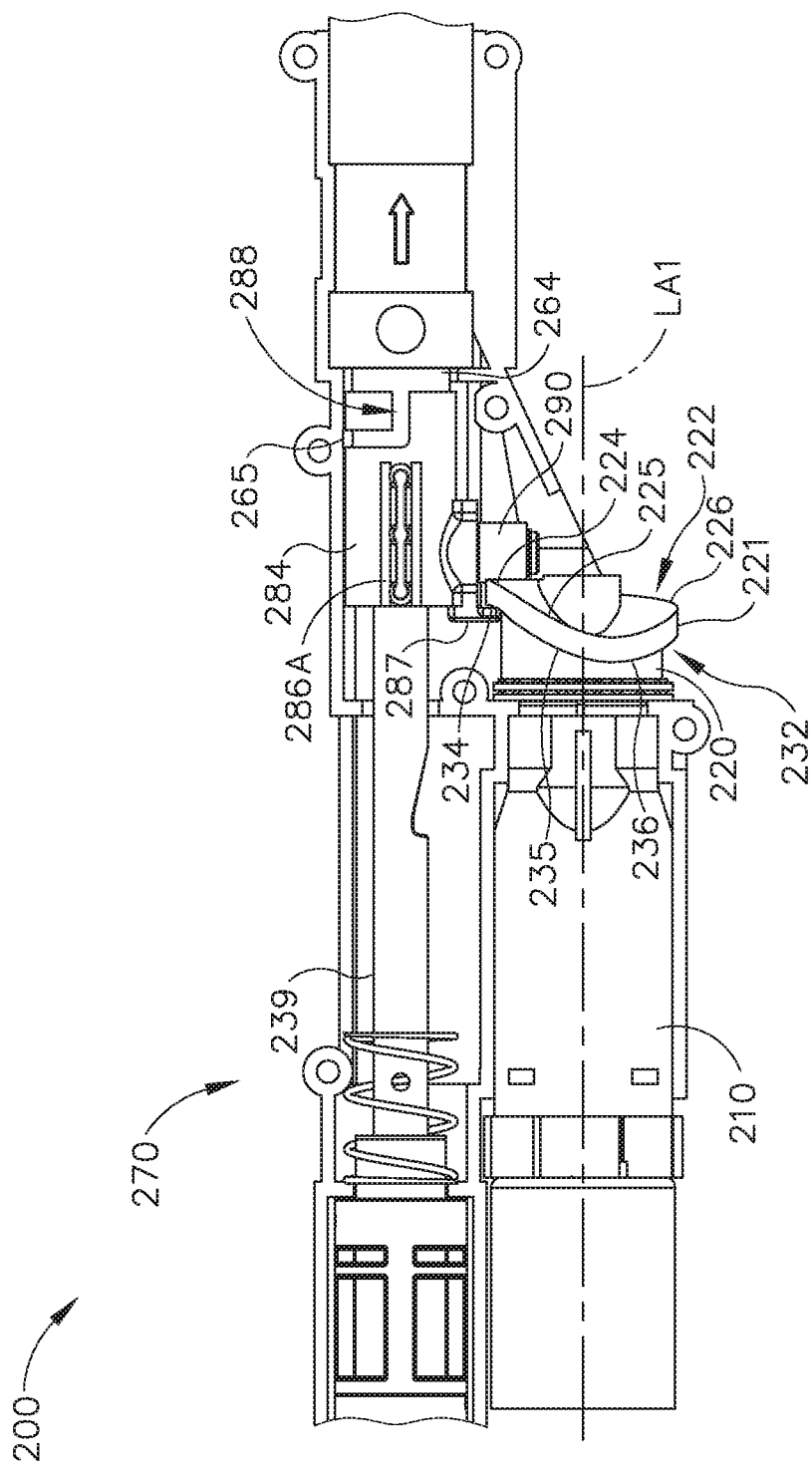
FIG. 11C depicts a side elevational view of the instrument of FIG. 7 with the motor and barrel cam a third rotational position.
Figure 11D:
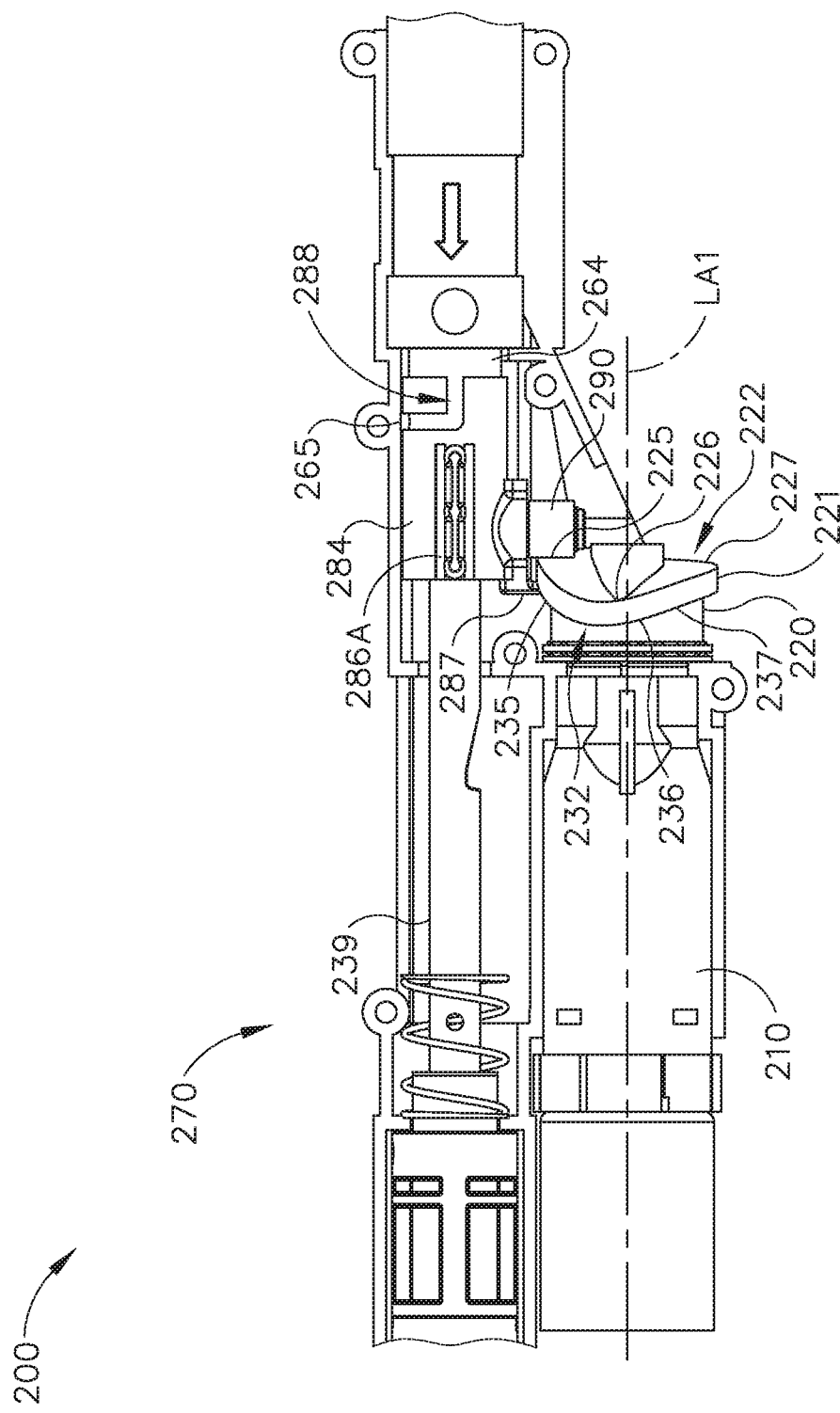
FIG. 11D depicts a side elevational view of the instrument of FIG. 7 with the motor and barrel cam a fourth rotational position.
Figure 11E:
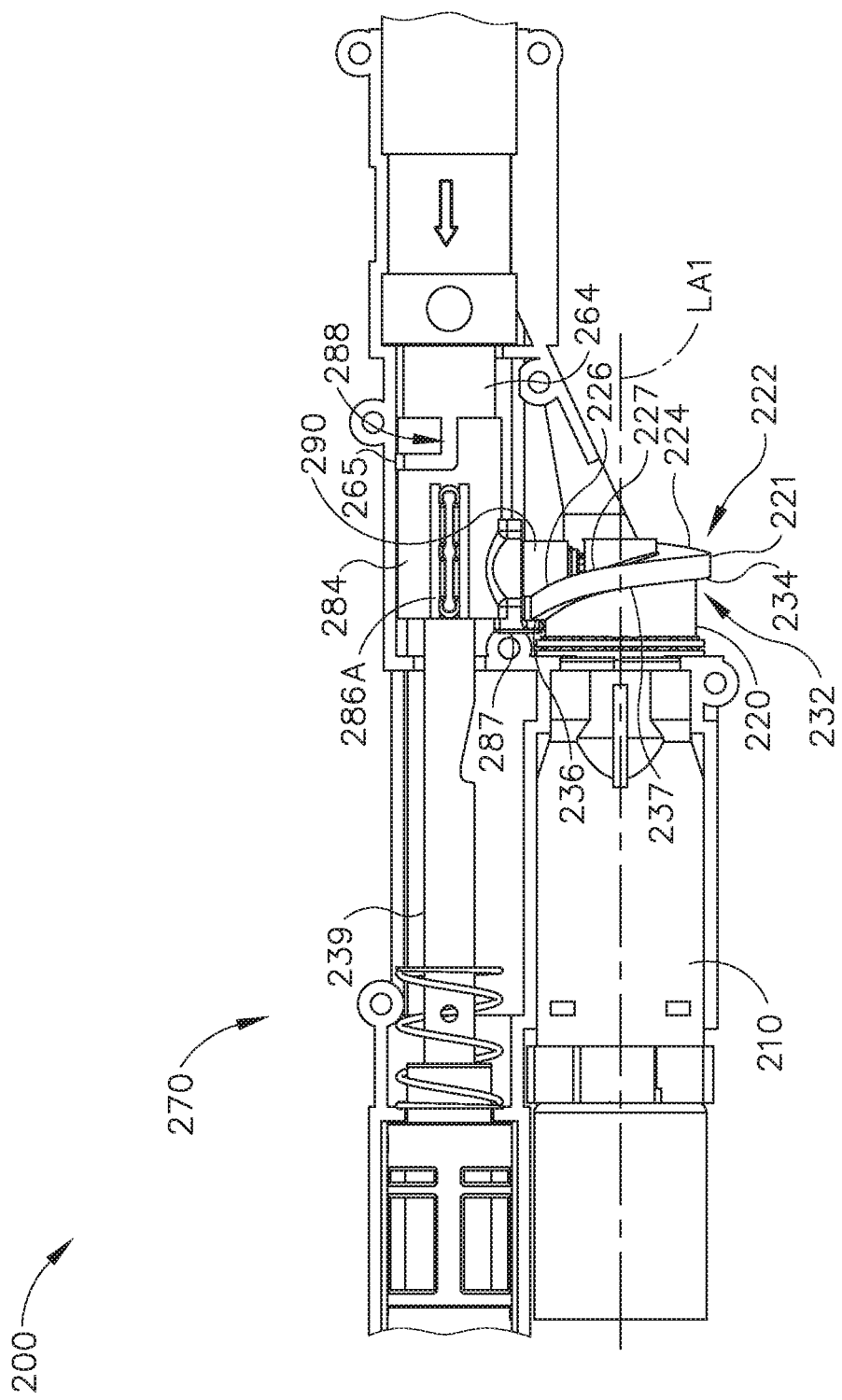
FIG. 11E depicts a side elevational view of the instrument of FIG. 7 with the motor and barrel cam returned to the first rotational position upon completion of a firing stroke.

For instance, as shown in FIG. 11A, roller (290) is in contact with proximal portion (226) of sloped distal face (222) of barrel cam (220). In this position, cam follower body (284) and driver actuator (264) are in a proximal position, and thus the staple driver remains in a proximal position. As shown in FIG. 11B, as motor (210) rotates barrel cam (220), roller (290) remains in contact with sloped distal face (222) and transfers distal motion to cam follower body (284) and driver actuator (264). As barrel cam (220) is rotated to the position shown in FIG. 11B, roller (290) is transitioned via intermediate portion (227) from proximal portion (226) to distal portion (224). As shown in FIG. 11C, roller (290) is in contact with distal portion (224) of sloped distal face (222) of barrel cam (220) as barrel cam (220) reaches approximately 270° of rotation. In this position, cam follower body (284) and driver actuator (264) are each in a distal position, and thus the staple driver is driven into a distal position such that the plurality of staple driving features, the annular array of staples, and the knife are driven distally as well. As shown in FIG. 11D, as motor (210) rotates barrel cam (220) further in the same direction, sloped proximal face (232) drives cam follower body (284) and driver actuator (264) proximally via cam follower arm (287). As barrel cam (220) completes 360° of rotation, sloped proximal face (232) returns cam follower body (284) and driver actuator (264) back to the fully proximal position via cam follower arm (287) as shown in FIG. 11E; and thus the staple driver and knife are returned back to the fully proximal position as well. While the full 360° revolution of barrel cam (220) is allocated as 270° for distal motion of driver actuator (264) and the remaining 90° for proximal motion of driver actuator, it should be understood that the allocation may be made in any other suitable fashion (e.g., 180° for distal motion and 180° for proximal motion, etc.). It should also be understood that a full range of distal and proximal travel may be provided by less than 360° of rotation of barrel cam (720).

Figure 42:
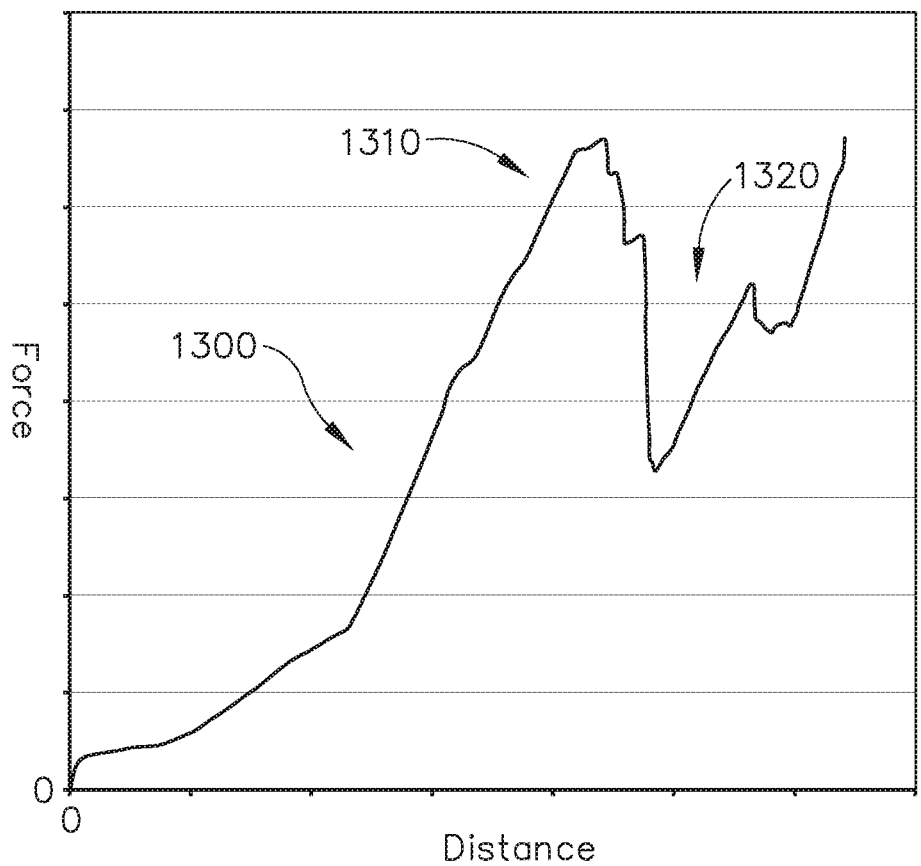
FIG. 42 depicts an exemplary force profile associated with a firing stroke for a circular stapling surgical instrument.

In some versions of instrument (200), anvil (240) contains a breakable washer that is broken by the knife when the knife completes a full distal range of motion. In some instances, the washer thus provides an audible or haptic feedback through actuator handle assembly (270) as the washer breaks in response to completion of full advancement of the knife toward anvil (240), though such audible/haptic feedback is not necessary. It should be understood that the presence of the washer may present a sudden increase in the force required to advance driver actuator (264) distally. FIG. 42 shows an exemplary force profile encountered by driver actuator (264) during the range of distal travel of driver actuator (264). In a first range (1300) of distal motion, driver actuator (264) encounters a gradually increasing load or resisting force as the knife passes through tissue. In a second range (1310) of distal motion, driver actuator (264) encounters a spike in load or resisting force as the knife passes through the washer. In a third range (1320) of distal motion, driver actuator (264) first encounters a sudden drop in load or resisting force after the washer breaks, then a subsequent increase in load or resisting force as stapling head assembly (218) drives staples into anvil (240) to thereby form staples to their final height. In view of the foregoing, it should be further understood that during the transition from the position shown in FIG. 11A to the position shown in FIG. 11C, the configuration of sloped distal face (222) may provide an increasing mechanical advantage as driver actuator (264) reaches the end of its distal movement, thereby providing greater force by which to break the washer. For instance, the knife may encounter the washer as the knife travels from a position associated with the configuration shown in FIG. 11B to a position associated with the configuration shown in FIG. 11C; and sloped distal face (222) may provide an increasing mechanical advantage as knife (236) approaches the end of its distal range of movement, thereby providing greater distal driving force by which to break the washer and form the staples. Of course, the breakable washer may be omitted entirely in some versions.

B. Second Exemplary Motor and Cam Assembly

Figure 12:
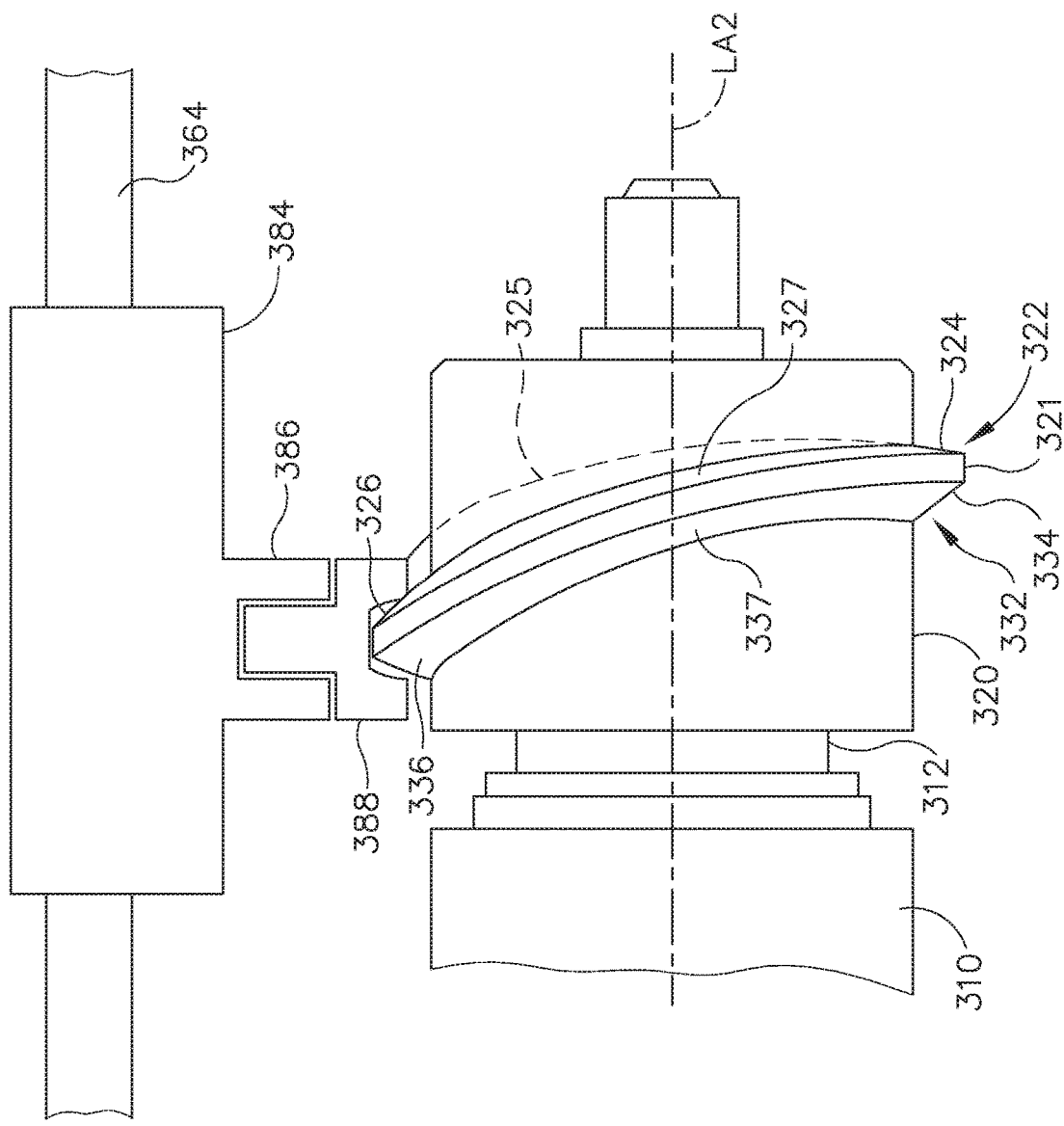
FIG. 12 depicts a side elevational view of an exemplary alternative barrel cam that may be incorporated into the instrument of FIG. 7.

FIG. 12 shows exemplary alternative components that may be incorporated into instrument (200) to actuate the staple driver and knife. In particular, FIG. 12 shows an exemplary alternative motor (310) and barrel cam (320) configured to operate substantially similar to motor (210) and barrel cam (220) discussed above except for the differences discussed below. Motor (310) and barrel cam (320) are configured to drive a staple driver (not shown) distally and proximally through one revolution of barrel cam (320) via translation of a cam follower body (384) and a driver actuator (364). Cam follower body (384) is coupled to driver actuator (364) (e.g. via a bayonet slot formed in cam follower body (384), etc.). Driver actuator (364) of the present example is configured to operate substantially similar to driver actuator (64) of instrument (10) discussed above. In particular, a distal end of driver actuator (364) is coupled to the staple driver such that driver actuator (364) actuates the staple driver when motor (310) longitudinally translates driver actuator (364).

Motor (310) is disposed within an actuator handle assembly (not shown) parallel to a proximal portion of driver actuator (364). Barrel cam (320) is coupled with motor (310) via a shaft (312). Actuation of motor (310) causes rotation of shaft (312) and barrel cam (320) about a longitudinal axis (LA2) defined by motor (310). As best seen in FIG. 12, barrel cam (320) comprises a lip (321) projecting from an exterior surface of barrel cam (320). Lip (321) comprises an annular sloped distal face (322). Sloped distal face (322) comprises a distal portion (324) and a proximal portion (326). Distal portion (324) and proximal portion (326) are disposed on radially opposite sides of barrel cam (320). Distal portion (324) presents a portion of sloped distal face (322) having a longitudinal position relative to longitudinal axis (LA2) more distal than that of proximal portion (326). Sloped distal face (322) further comprises intermediate portions (325, 327) disposed between distal portion (324) and proximal portion (326). Intermediate portions (325, 327) are contoured to provide a substantially smooth transition between distal portion (324) and proximal portion (326) along opposite sides of barrel cam (320). Thus, relative to a fixed point in space, the longitudinal position of sloped distal face (322) will change from the proximal position presented by proximal portion (326) to the distal position presented by distal portion (324); and back again as barrel cam (320) is rotated through one revolution.

Lip (321) further comprises an annular sloped proximal face (332). Sloped proximal face (332) and sloped distal face (322) have parallel contours. Sloped proximal face (332) comprises a distal portion (334) and a proximal portion (336). Distal portion (334) and proximal portion (336) are disposed on radially opposite sides of barrel cam (320). Distal portion (334) presents a portion of sloped proximal face (332) having a longitudinal position relative to longitudinal axis (LA2) more distal than that of proximal portion (336). Sloped proximal face (332) further comprises intermediate portions (335, 337) disposed between distal portion (334) and proximal portion (336). Intermediate portions (335, 337) are contoured to provide a substantially smooth transition between distal portion (334) and proximal portion (336) along opposite sides of barrel cam (320). Thus, relative to a fixed point in space, the longitudinal position of sloped proximal face (332) will change from the proximal position presented by proximal portion (336) to the distal position presented by distal portion (334); and back again as barrel cam (320) is rotated through one revolution.

Cam follower body (384) comprises an arm (386) and an engagement feature (388). Arm (386) is secured to and extends from a bottom of cam follower body (384) such that longitudinal translation of arm (386) causes longitudinal translation of cam follower body (384). Engagement feature (388) is coupled to arm (386). Engagement feature (388) straddles lip (321) and thus engagement feature (388) is configured to remain engaged with lip (321) as barrel cam (320) rotates. Engagement feature (388) and arm (386) may comprise different materials. For instance, engagement feature (388) may comprise a more durable material to prevent wear from contact with lip (321). Additionally, engagement feature (388) may comprise a material selected to reduce friction between engagement feature (388) and lip (321) of barrel cam (320). Various kinds of materials that may be used to provide reduced friction between engagement feature (388) and lip (321) will be apparent to those of ordinary skill in the art in view of the teachings herein.

As barrel cam (320) is rotated through one revolution, the longitudinal position of cam follower body (384) and driver actuator (364) will translate from a proximal position to a distal position as barrel cam (320) completes 270° of rotation, caused by contact between engagement feature (388) and distal portion (324) of lip (321); and back again to the proximal position, caused by contact between engagement feature (388) and proximal portion (326) of lip (321) as barrel cam (320) completes 360° of rotation. Thus it should be understood that cam follower body (384), driver actuator (364), and the staple driver will longitudinally translate from the proximal position to the distal position and back again in a single revolution of barrel cam (320). This translation of cam follower body (384) from the proximal position to the distal position and back again will cause the staple driver and knife to be driven distally and proximally as well via driver actuator (364). While the full 360° revolution of barrel cam (320) is allocated as 270° for distal motion of driver actuator (364) and the remaining 90° for proximal motion of driver actuator, it should be understood that the allocation may be made in any other suitable fashion (e.g., 180° for distal motion and 180° for proximal motion, etc.). It should also be understood that a full range of distal and proximal travel may be provided by less than 360° of rotation of barrel cam (320).

Some versions of instrument (10) contain a breakable washer that is broken by the knife when the knife completes a full distal range of motion, as discussed above with reference to FIG. 42. It will further be understood that the configuration of sloped distal face (322) may provide an increasing mechanical advantage as the knife reaches the end of its distal movement, thereby providing greater force by which to break the washer and form the staples. Again, though, the breakable washer may be omitted entirely in some versions.

C. Third Exemplary Motor and Cam Assembly

Figure 13:
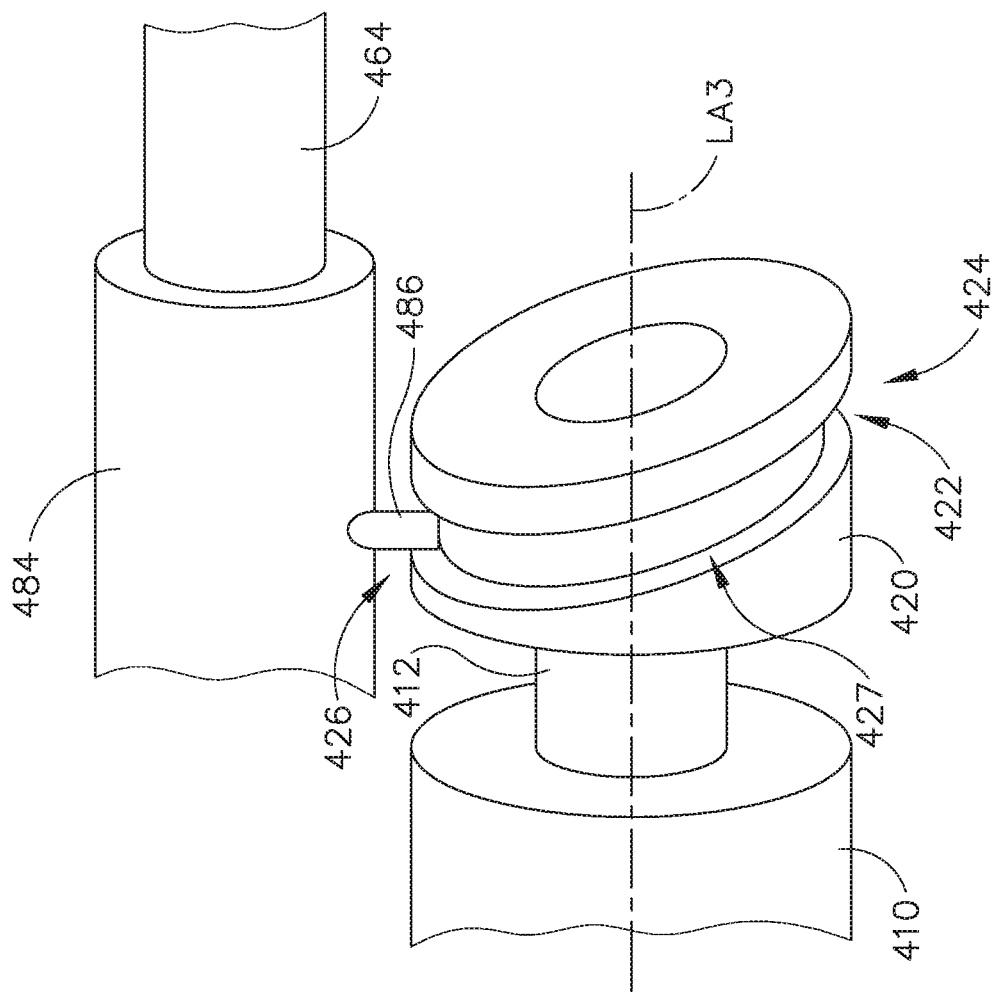
FIG. 13 depicts a perspective view of yet another exemplary alternative barrel cam that may be incorporated into the instrument of FIG. 7.

FIG. 13 shows other exemplary alternative components that may be incorporated into instrument (200) to actuate the staple driver and knife. In particular, FIG. 13 shows an exemplary alternative motor (410) and barrel cam (420) configured to operate substantially similar to motor (210) and barrel cam (220) discussed above except for the differences discussed below. In particular, motor (410) and barrel cam (420) are configured to drive a staple driver (not shown) distally and proximally through one revolution of barrel cam (420) via translation of a cam follower body (484) and a driver actuator (464). Cam follower body (484) is coupled to driver actuator (464) (e.g. via a bayonet slot formed in cam follower body (484), etc.). Driver actuator (464) of the present example is configured to operate substantially similar to driver actuator (64) of instrument (10) discussed above. In particular, a distal end of driver actuator (464) is coupled to the staple driver such that driver actuator (464) actuates the staple driver when motor (410) longitudinally translates driver actuator (464).

Motor (410) is disposed within an actuator handle assembly (not shown) parallel to a proximal portion of driver actuator (464). Barrel cam (420) is coupled with motor (410) via a shaft (412). Actuation of motor (410) causes rotation of shaft (412) and barrel cam (420) about a longitudinal axis (LA3) defined by motor (410). Barrel cam (420) defines an annular sloped channel (422) within an exterior of barrel cam (420). Sloped channel (422) comprises a distal portion (424) and a proximal portion (426). Distal portion (424) and proximal portion (426) are disposed on radially opposite sides of barrel cam (420). Distal portion (424) presents a portion of sloped channel (422) having a longitudinal position relative to longitudinal axis (LA3) more distal than that of proximal portion (426). Sloped channel (422) further comprises intermediate portions (425, 427) disposed between distal portion (424) and proximal portion (426). Intermediate portions (425, 427) are contoured to provide a substantially smooth transition between distal portion (424) and proximal portion (426) along opposite sides of barrel cam (420). Thus, relative to a fixed point in space, the longitudinal position of sloped channel (422) will change from the proximal position presented by proximal portion (426) to the distal position presented by distal portion (424); and back again as barrel cam (420) is rotated through one revolution.

Cam follower body (484) comprises an arm (486). Arm (486) is secured to cam follower body (484) such that longitudinal translation of arm (486) causes longitudinal translation of cam follower body (484). Arm (486) is slidably disposed within sloped channel (422) and is configured to remain within sloped channel (422) as barrel cam (420) rotates. Thus, it should be understood that as barrel cam (420) is rotated through one revolution, the longitudinal position of cam follower body (484) and driver actuator (464) will translate from a proximal position to a distal position as barrel cam (420) completes 270° of rotation, caused by contact between engagement feature (488) and distal portion (424) of sloped channel (422); and back again to the proximal position, caused by contact between engagement feature (488) and proximal portion (426) of sloped channel (422) as barrel cam (420) completes 360° of rotation. Cam follower body (484), driver actuator (464), and the staple driver will thus longitudinally translate from the proximal position to the distal position and back again in a single revolution of barrel cam (420). This translation of cam follower body (484) from a proximal position to a distal position and back again will cause the staple driver and knife to be driven distally and proximally as well via driver actuator (464). While the full 360° revolution of barrel cam (420) is allocated as 270° for distal motion of driver actuator (464) and the remaining 90° for proximal motion of driver actuator, it should be understood that the allocation may be made in any other suitable fashion (e.g., 180° for distal motion and 180° for proximal motion, etc.) It should also be understood that a full range of distal and proximal travel may be provided by less than 360° of rotation of barrel cam (420).

Some versions of instrument (10) contain a breakable washer that is broken by the knife when the knife completes a full distal range of motion, as discussed above with reference to FIG. 42. It will further be understood that the configuration of sloped channel (422) may provide an increasing mechanical advantage as the knife reaches the end of its distal movement, thereby providing greater force by which to break the washer and form the staples. Again, though, the breakable washer may be omitted entirely in some versions.

D. Fourth Exemplary Motor and Cam Assembly

Figure 14:
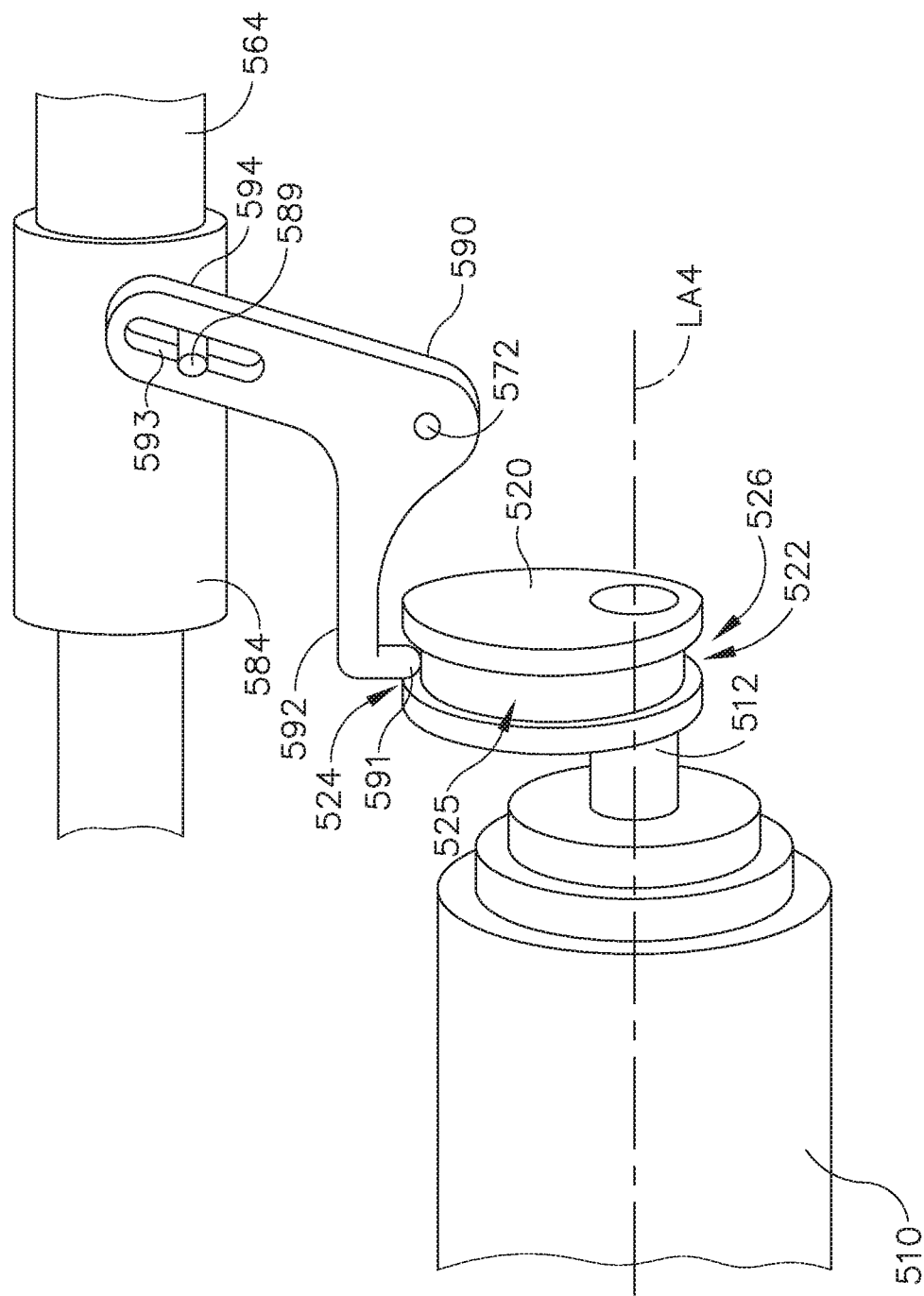
FIG. 14 depicts a perspective view of a motor and exemplary alternative cam that may be incorporated into the instrument of FIG. 7.
Figure 15:
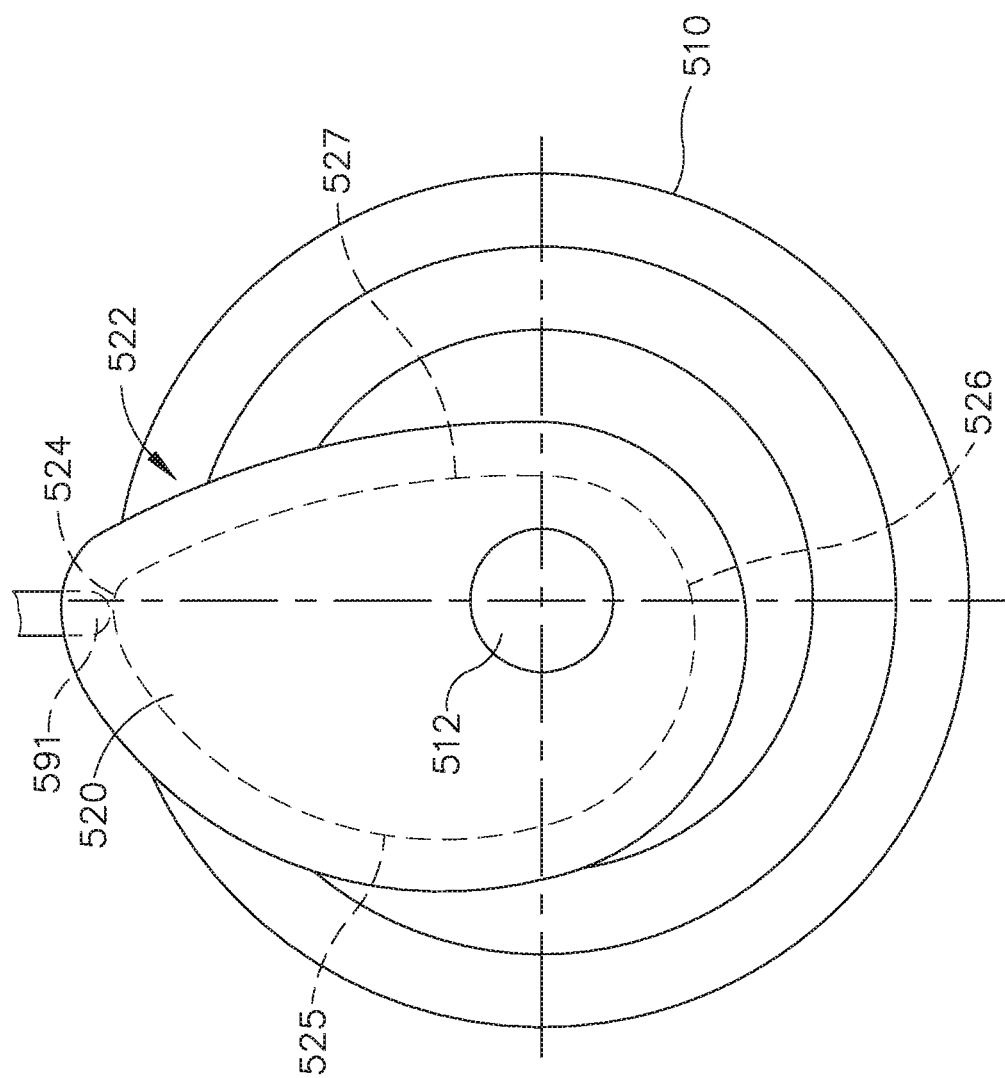
FIG. 15 depicts a front elevational view of the motor and cam of FIG. 14.

FIGS. 14-17 show additional exemplary alternative components that may be incorporated into instrument (200) to actuate the staple driver and knife. In particular, FIGS. 16A-16E show a motor (510) disposed within an actuator handle assembly (570) parallel to a proximal portion of a driver actuator (564). As best seen in FIGS. 14-15, a cam (520) is mounted eccentrically on a shaft (512) extending distally from motor (510). Actuation of motor (510) causes rotation of cam (520) about a longitudinal axis (LA4) defined by motor (510). As will be discussed in more detail below, cam (520) defines a channel (522) in an exterior surface of cam (520). As best seen in FIGS. 12-13, channel (522) comprises a first portion (524) and a second portion (526). First portion (524) and second portion (526) are disposed on radially opposite sides of cam (520). First portion (524) presents a portion of channel (522) having a radial distance from longitudinal axis (LA4) that is greater than a radial distance of second portion (526) from longitudinal axis (LA4).

Channel (522) further comprises intermediate portions (525, 527) disposed between first portion (524) and second portion (526). Intermediate portions (525, 527) are contoured to provide a substantially smooth transition between first portion (524) and second portion (526) along opposite sides of cam (520). Thus, it should be understood that, relative to a fixed point in space, a radial distance from a bottom of channel (522) to longitudinal axis (LA4) will change from the lesser radial distance presented by second portion (526) to the greater radial distance presented by first portion (524); and back again as cam (520) is rotated through one revolution.

As shown in FIGS. 14 and 16A-16E, a follower interface feature (584) is coupled with a pivoting cam follower (590). Handle assembly (570) comprises a pivot pin (572) to which cam follower (590) is rotatably coupled such that cam follower (590) is free to rotate about pivot pin (572). A first portion (592) of cam follower (590) is slidably disposed within channel (522). A free end of first portion (592) of cam follower (590) defines an engagement feature (591) configured to cause first portion (592) to remain within channel (522) as cam (520) rotates. FIG. 17 shows one exemplary version of engagement feature (591). In particular, FIG. 17 shows cam (520) comprising a first cam body portion (520A) and a second cam body portion (520B). Channel (522) is formed between cam body portions (520A, 520B). Engagement feature (591) may thus be captured within channel (522) as first and second cam body portions (520A, 520B) are assembled to form cam (520). The portion of channel (522) formed by first cam body portion (520A) defines a lip (523) projecting into channel (522) and thereby limiting an exterior opening (519) of channel (522). Engagement feature (591) is larger than exterior opening (519) of channel (522) and will therefore remain within channel (522) as cam (520) rotates.

Thus, as cam (520) is rotated through one revolution, a radial distance from engagement feature (591) to longitudinal axis (LA4) will change from the lesser radial distance caused by second portion (526) to the greater radial distance caused by first portion (524) and back again. This change of radial distance of engagement feature (591), and thus the free end of first portion (592) of cam follower (590), will cause cam follower (590) to rotate about pivot pin (572) from a first position to a second position and back again. As will be discussed in more detail below, lip (523) is further operable to drive engagement feature (591) within channel (522) such that cam follower (590) rotates counter-clockwise about pivot pin (572) to thereby retract follower interface feature (584), driver actuator (564), and the staple driver proximally.

A second portion (594) of cam follower (590) presents a slot (593). Follower interface feature (584) comprises a pin (589) extending laterally from follower interface feature (584). Pin (589) is slidably and rotatably disposed within slot (593) such that cam follower (590) is thereby coupled with follower interface feature (584) and further such that, as cam follower (590) rotates about pivot pin (572), follower interface feature (584) translates longitudinally. Follower interface feature (584) is coupled to driver actuator (564) (e.g. via a bayonet slot formed in follower interface feature (584), etc.). Driver actuator (564) is coupled to the staple driver and knife such that longitudinal translation of follower interface feature (584) actuates the staple driver and knife. It should therefore be understood that as cam (520) is rotated through a first part of a full revolution, cam follower (590) is rotated clockwise from a first position to a second position, thus translating follower interface feature (584) distally from a first longitudinal position to a second longitudinal position; and as cam (520) is rotated through the remaining part of the full revolution, cam follower (590) is rotated counterclockwise from the second position back to the first position, thus translating follower interface feature (584) proximally from the second longitudinal position back to the first longitudinal position. This translation of follower interface feature (584) from a first longitudinal position to a second longitudinal position and back again will cause the staple driver to be driven from a proximal position to a distal position and back again via driver actuator (564).

Figure 16A:
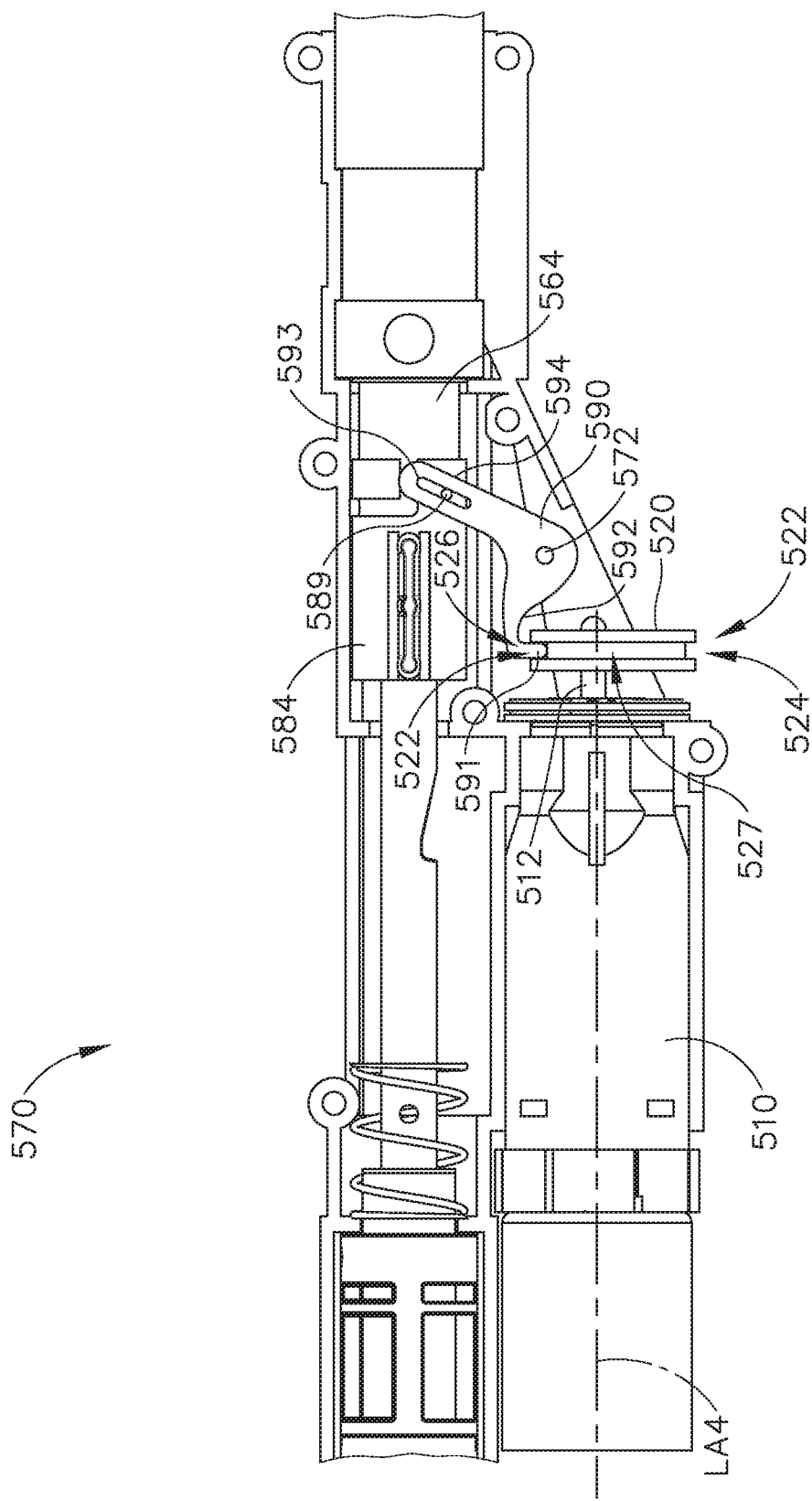
FIG. 16A depicts a side elevational view of an exemplary circular stapling surgical instrument with the motor and cam of FIG. 14 in a first rotational position.
Figure 16B:
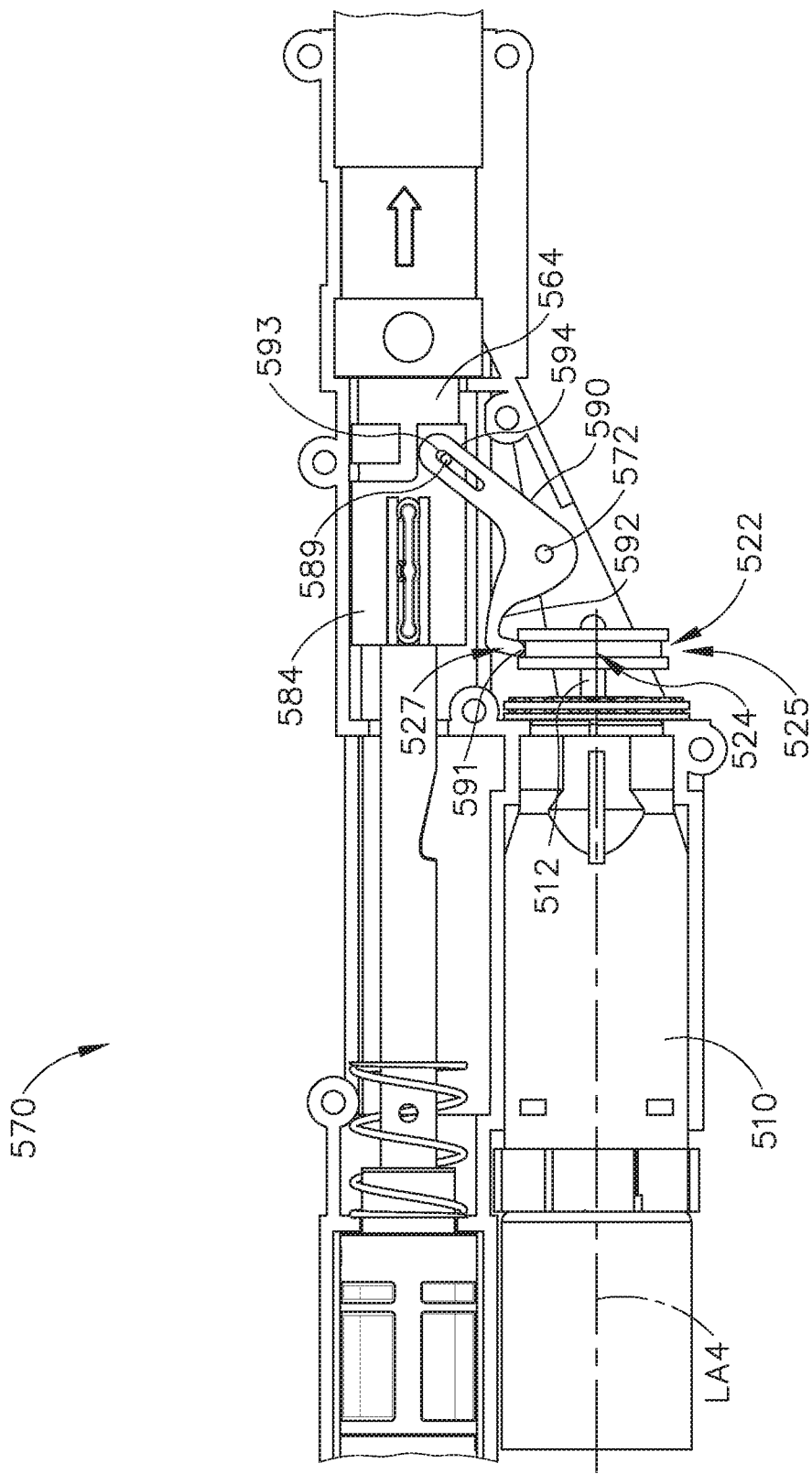
FIG. 16B depicts a side elevational view of the instrument of FIG. 16A with the motor and cam of FIG. 14 a second rotational position.

FIG. 16A shows engagement feature (591) of cam follower (590) engaged with second portion (526) of channel (522) of cam (520). In this position, cam follower (590) is in the first position and follower interface feature (584) is in a proximal position, and thus the staple driver remains in a proximal position. As shown in FIG. 16B, as motor (510) rotates cam (520), engagement feature (591) remains engaged with channel (522), and engagement feature (591) is transitioned via intermediate portion (525) from engaging second portion (526) of channel (522) to engaging first portion (524) of channel (522). As engagement feature (591) is transitioned from second portion (526) to first portion (524), cam follower (590) is rotated clockwise about pivot pin (572) from the first position toward the second position due to contact between engagement feature (591) and intermediate portion (527). As cam follower (590) is rotated clockwise toward the second position, follower interface feature (584) and driver actuator (564) are driven distally.

Figure 16C:
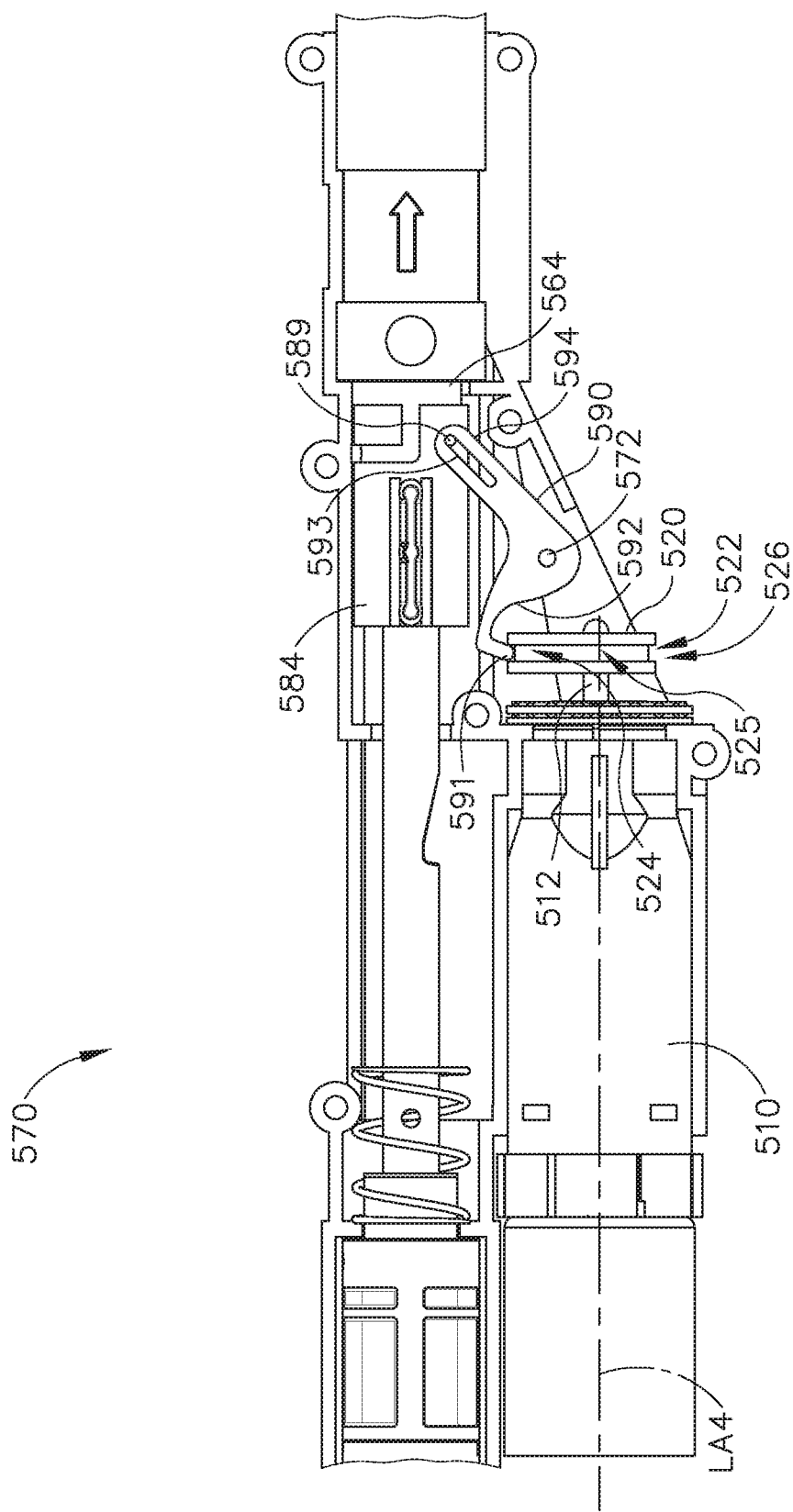
FIG. 16C depicts a side elevational view of the instrument of FIG. 16A with the motor and cam of FIG. 14 a third rotational position.
Figure 16D:
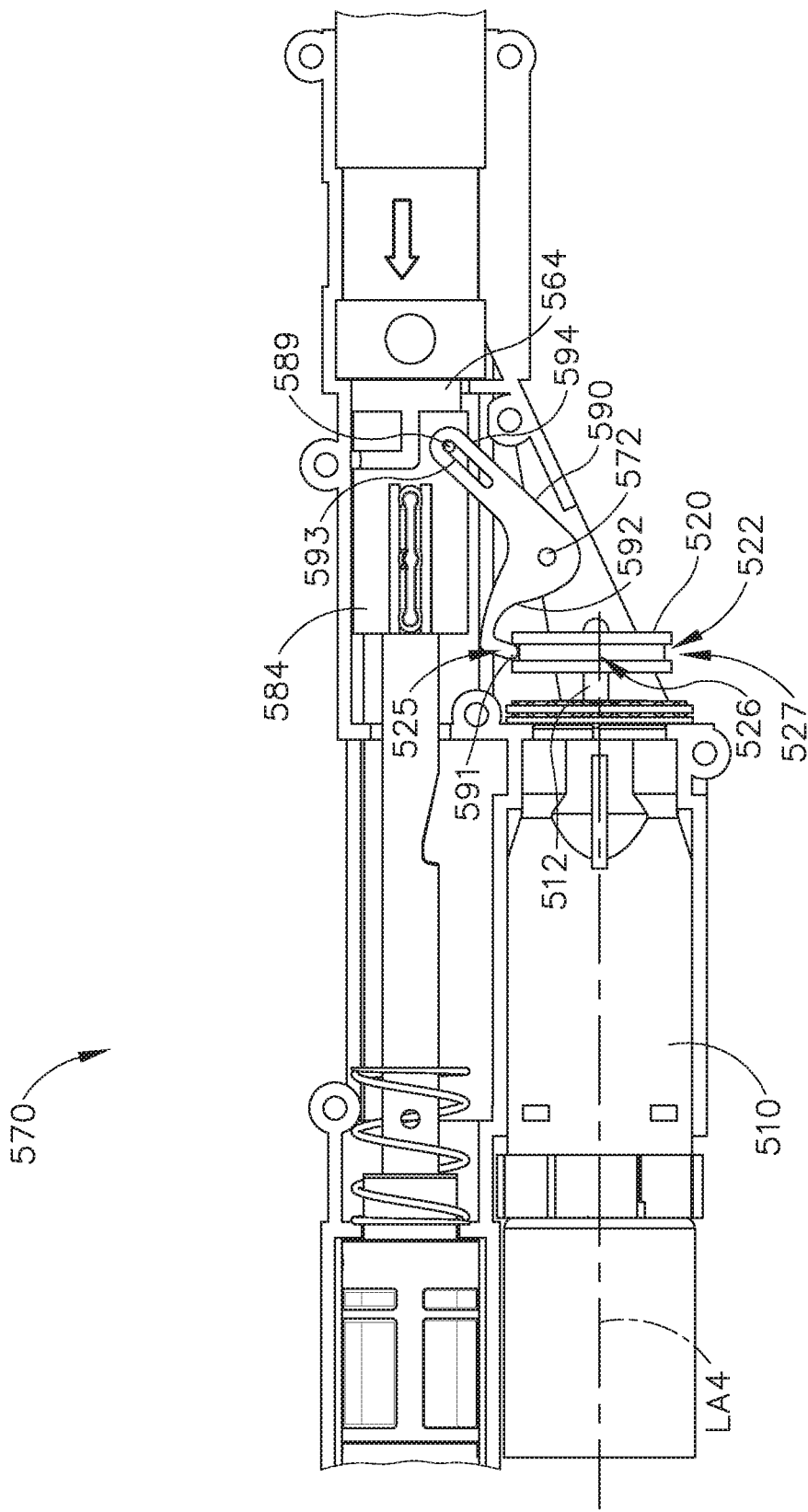
FIG. 16D depicts a side elevational view of the instrument of FIG. 16A with the motor and cam of FIG. 14 a fourth rotational position.

As shown in FIG. 16C, after cam (520) completes 180° of rotation, engagement feature (591) is engaged with first portion (524) of channel (522) of cam (520). In this position, cam follower (590) has been rotated completely into the second position and follower interface feature (584) and driver actuator (564) are in the distal position; and thus the staple driver is driven into a distal position such that the plurality of staple driving features, the annular array of staples, and the knife are driven distally. As shown in FIG. 16D, as motor (510) continues to rotate cam (520) further in the same direction, engagement feature (591) remains engaged with channel (522) due to lip (523). As cam (520) is further rotated, engagement feature (591) is transitioned via intermediate portion (525) from first portion (524) to second portion (526). As engagement feature (591) is transitioned from first portion (524) to second portion (526), cam follower (590) is rotated counterclockwise about pivot pin (572) from the second position back toward the first position due to contact between engagement feature (591) and lip (523). As cam follower (590) is rotated counterclockwise back toward the first position, cam follower (590) pulls follower interface feature (584) and driver actuator (564) proximally. As cam (520) is further rotated such that cam (520) completes 360° of rotation, engagement feature (591) is transitioned via intermediate portion (525) from first portion (524) back to second portion (526) such that follower interface feature (584) and driver actuator (564) are returned to the proximal position as shown in FIG. 16E.

As best seen in FIG. 15, intermediate portion (525) and intermediate portion (527) have different contours. These different contours represent different rates of change of the radial distance from the outwardly facing caroming surface of channel (522) to longitudinal axis (LA4) presented by first portion (524) to second portion (526) and vice versa. In particular, intermediate portion (525) represents a more gradual rate of change from the radial distance presented by second portion (526) to the radial distance presented by first portion (524) whereas intermediate portion (527) represents a more rapid rate of change from the radial distance presented by first portion (524) to the radial distance presented by second portion (526) or vice versa depending on the direction in which cam (520) is rotated. It should be understood that these differing rates of change will be communicated to follower interface feature (584), driver actuator (564), and the staple driver via cam follower (590) thus causing differing rates of longitudinal translation of follower interface feature (584), driver actuator (564), and the staple driver. For instance, intermediate portion (525) may provide a relatively slow rate of distal advancement of driver actuator (564) while intermediate portion (527) provides a relatively rapid rate of proximal retraction of driver actuator (564). Of course, these rates may be further varied in any suitable way.

While the full 360° revolution of cam (520) is allocated as 180° for distal motion of driver actuator (564) and the remaining 180° for proximal motion of driver actuator, it should be understood that the allocation may be made in any other suitable fashion (e.g., 270° for distal motion and 90° for proximal motion, etc.). It should also be understood that a full range of distal and proximal travel may be provided by less than 360° of rotation of cam (520).

Some versions of instrument (10) contain a breakable washer that is broken by the knife when the knife completes a full distal range of motion, as discussed above with reference to FIG. 42. It will further be understood that the configuration of channel (522) may provide an increasing mechanical advantage as the knife reaches the end of its distal movement, thereby providing greater force by which to break the washer and form the staples. Again, though, the breakable washer may be omitted entirely in some versions.

E. Fifth Exemplary Alternative Motor and Cam Assembly

Figure 18:
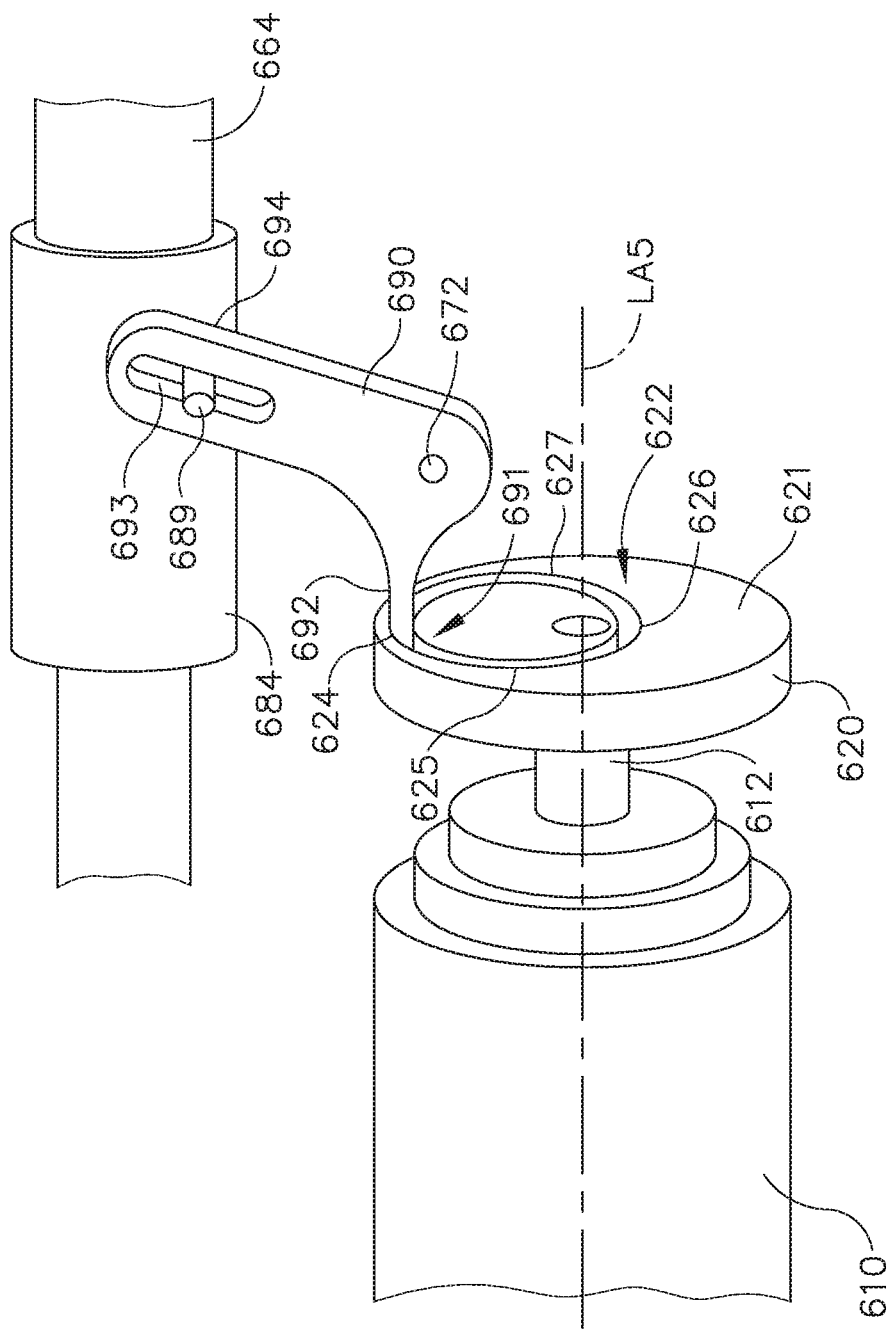
FIG. 18 depicts a perspective view of a motor and an exemplary alternative cam that may be incorporated into the instrument of FIG. 7.
Figure 19:
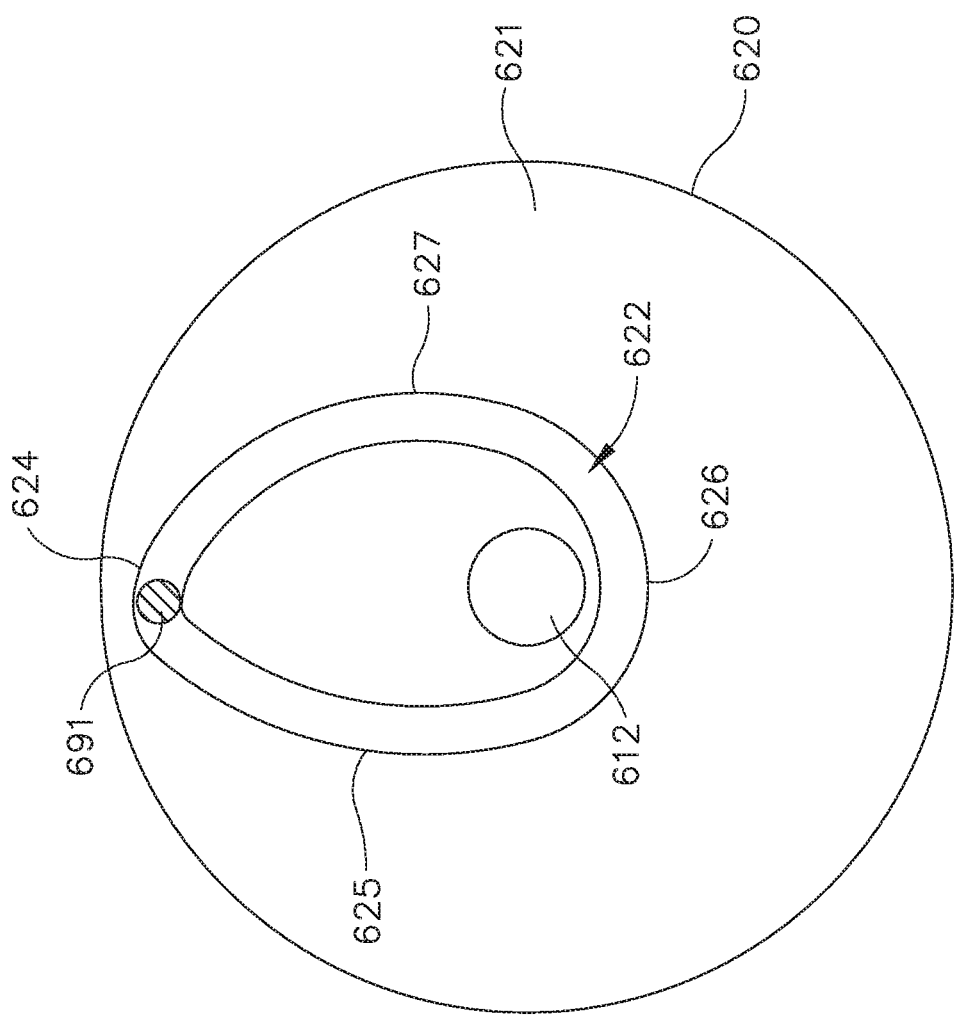
FIG. 19 depicts a front elevational view of the motor and cam of FIG. 18.
Figure 20:
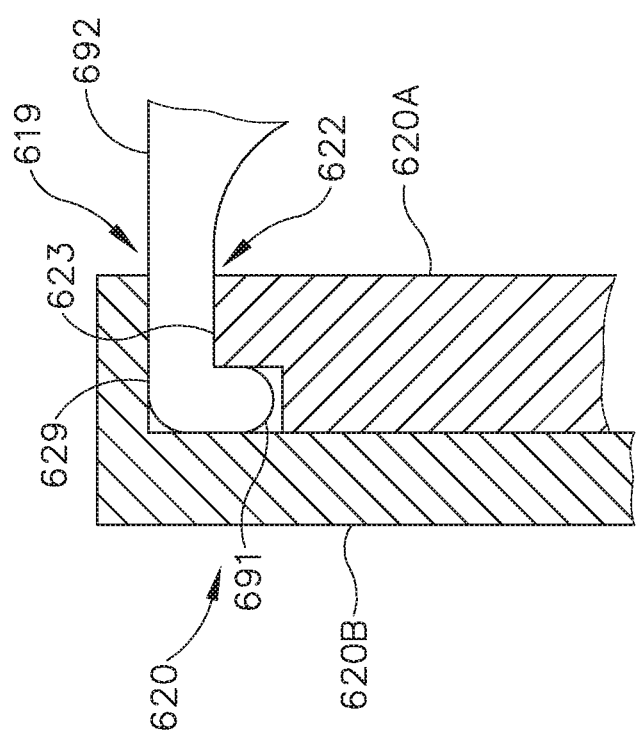
FIG. 20 depicts a side cross-sectional view of an exemplary alternative cam locking feature.

FIGS. 18-20 show further exemplary alternative components that may be incorporated into instrument (200) to actuate the staple driver and knife. In particular, FIGS. 18-20 show an exemplary alternative motor (610) and cam (620) configured to operate substantially similar to motor (510) and cam (520) discussed above except for the differences discussed below. Motor (610) and cam (620) are configured to drive a staple driver (not shown) distally and proximally through one revolution of cam (620) via translation of a driver actuator (664) and a follower interface feature (684).

As shown in FIG. 18, motor (610) is disposed within an actuator handle assembly (not shown) parallel to a proximal portion of driver actuator (664). Cam (620) is coupled with a distal end of motor (610) via a shaft (612). Actuation of motor (610) causes rotation of cam (620) about a longitudinal axis (LA5) defined by motor (610). As best seen in FIG. 17, a cam channel (622) is defined within a distal face (621) of cam (620). Cam channel (622) is eccentrically positioned about longitudinal axis (LA5). Cam channel (622) comprises a first portion (624) and a second portion (626). First portion (624) and second portion (626) are disposed on radially opposite sides of cam channel (622). First portion (624) presents a portion of cam channel (622) having a radial distance from longitudinal axis (LA5) that is greater than a radial distance of second portion (626) from longitudinal axis (LA5).

Cam channel (622) further comprises intermediate portions (625, 627) disposed between first portion (624) and second portion (626). Intermediate portions (625, 627) are contoured to provide a substantially smooth transition between first portion (624) and second portion (626) along opposite sides of cam channel (622). Thus, relative to a fixed point in space, a radial distance from a bottom of channel (622) to longitudinal axis (LA5) will change from the lesser radial distance presented by second portion (626) to the greater radial distance presented by first portion (624); and back again as cam (620) is rotated through one full revolution.

As shown in FIG. 18, follower interface feature (684) comprises a pivoting cam follower (690). The handle assembly comprises a pivot pin (672) to which cam follower (690) is rotatably coupled such that cam follower (690) is free to rotate about pivot pin (672). A first portion (692) of cam follower (690) is slidably disposed within earn channel (622). A free end of first portion (692) of cam follower (690) defines an engagement feature (691) configured to cause first portion (692) to remain within cam Channel (622) as cam (620) rotates. FIG. 20 shows one exemplary version of engagement feature (691). In particular, FIG. 20 shows cam (620) comprising a first cam body portion (620A) and a second cam body portion (620B). Cam channel (622) is formed between first cam body portion (620A) and a second cam body portion (620B). Engagement feature (691) may thus be captured within cam channel (622) as first cam body portion (620A) and a second cam body portion (620B) are assembled to form cam (620). The portion of cam channel (622) formed by first cam body portion. (620A) defines a lip (623) projecting into cam channel (622) and thereby limiting an exterior opening (619) of cam channel (622). Engagement feature (691) is larger than exterior opening (619) of cam channel (622) and will therefore remain within cam channel (622) as cam (620) rotates.

Thus, as cam (620) is rotated through one revolution, a radial distance from engagement feature (691) to longitudinal axis (LA5) will change from the lesser radial distance caused by second portion (626) to the greater radial distance caused by first portion (624) and back again. This change of radial distance of engagement feature (691), and thus proximal end of first portion (692) of cam follower (690), will cause cam follower (690) to rotate about pivot pin (672) from a first position to a second position and back again. As will be discussed in more detail below, lip (623) is further operable to drive engagement feature (691) within cam channel (622) such that cam follower (690) rotates clockwise about pivot pin (672) to thereby drive follower interface feature (684), driver actuator (664), and the staple driver distally. As will also be discussed in more detail below, an inwardly presented surface (629) of cam channel (622) is operable to drive engagement feature (691) within cam channel (622) such that cam follower (690) rotates counter-clockwise about pivot pin (672) to thereby retract follower interface feature (684), driver actuator (664), and the staple driver proximally.

A second portion (694) of cam follower (690) presents a slot (693). Follower interface feature (684) comprises a pin (689) extending laterally from follower interface feature (684). Pin (689) is slidably and rotatably disposed within slot (693) such that cam follower (690) is thereby coupled with follower interface feature (684) and further such that, as cam follower (690) rotates about pivot pin (672), follower interface feature (684) translates longitudinally. As cam (620) is rotated through one revolution, the longitudinal position of follower interface feature (684) and driver actuator (664) will translate from a proximal position to a distal position as cam (620) completes 180° of rotation, caused by contact between engagement feature (691) and lip (623) at first portion (624); and back again to the proximal position, caused by contact between engagement feature (691) and inwardly presented surface (629) of cam channel (622) at second portion (626) as cam (620) completes 360° of rotation. It should therefore be understood that as cam (620) is rotated through a first part of a full revolution, cam follower (690) is rotated clockwise from a first position to a second position, thus translating follower interface feature (684) distally from a first longitudinal position to a second longitudinal position; and as cam (620) is rotated through the remaining part of the full revolution, cam follower (690) is rotated counterclockwise from the second position back to the first position, thus translating follower interface feature (684) proximally from the second longitudinal position back to the second longitudinal position. This translation of follower interface feature (684) from a first longitudinal position to a second longitudinal position and back again will cause the staple driver to be driven from a proximal position to a distal position and back again via driver actuator (664).

As best seen in FIG. 19, intermediate portion (625) and intermediate portion (627) have different contours. These different contours represent different rates of change of the radial distance from channel (622) to longitudinal axis (LA5) presented by first portion (624) to second portion (626) and vice versa. In particular, intermediate portion (625) represents a more gradual rate of change from the radial distance presented by second portion (626) to the radial distance presented by first portion (624); whereas intermediate portion (627) represents a more rapid rate of change from the radial distance presented by first portion (624) to the radial distance presented by second portion (626) or vice versa depending upon which direction in which cam (620) is rotated. It should be understood that these differing rates of change will be communicated to follower interface feature (684), driver actuator (664), and the staple driver via cam follower (690) thus causing differing rates of longitudinal translation of follower interface feature (684), driver actuator (664), and the staple driver. For instance, intermediate portion (625) may provide a relatively slow rate of distal advancement of driver actuator (664) while intermediate portion (627) provides a relatively rapid rate of proximal retraction of driver actuator (664). Of course, these rates may be further varied in any suitable way.

While the full 360° revolution of cam (620) is allocated as 180° for distal motion of driver actuator (664) and the remaining 180° for proximal motion of driver actuator, it should be understood that the allocation may be made in any other suitable fashion (e.g., 270° for distal motion and 90° for proximal motion, etc.). It should also be understood that a full range of distal and proximal travel may be provided by less than 360° of rotation of barrel cam (620).

Some versions of instrument (10) contain a breakable washer that is broken by the knife when the knife completes a full distal range of motion, as discussed above with reference to FIG. 42. It will further be understood that the configuration of channel (622) may provide an increasing mechanical advantage as the knife reaches the end of its distal movement, thereby providing greater force by which to break the washer and form the staples. Again, though, the breakable washer may be omitted entirely in some versions.

F. Sixth Exemplary Alternative Motor and Cam Assembly

Figure 23:
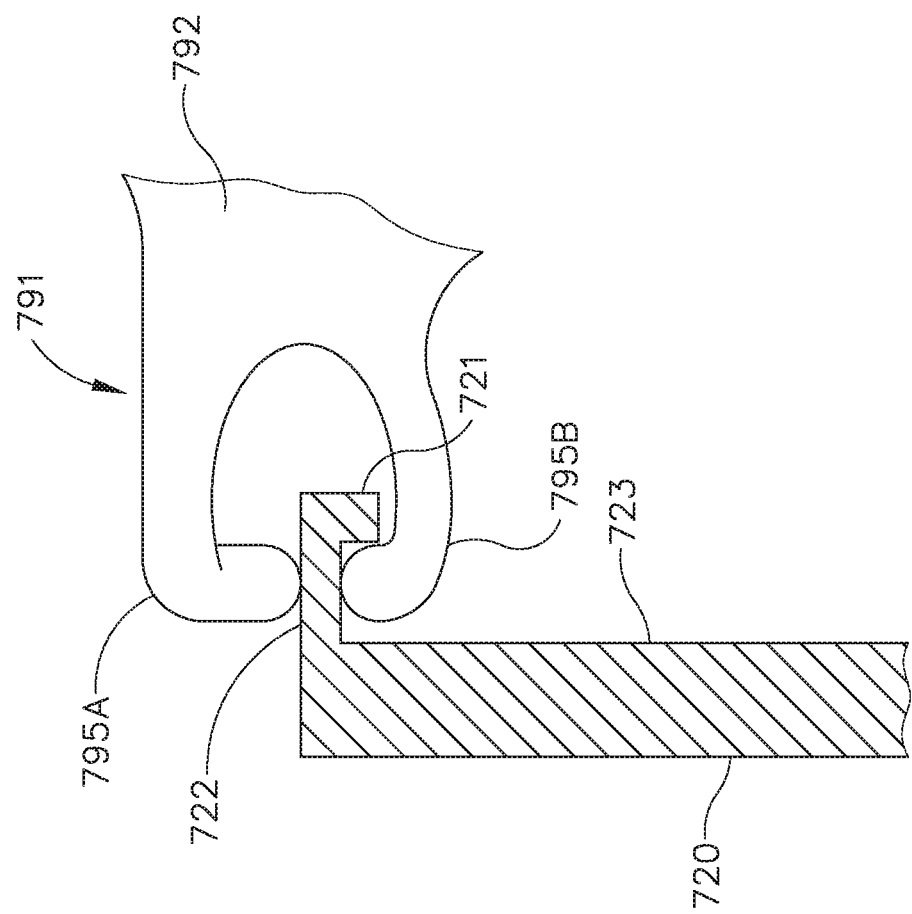
FIG. 23 depicts a side cross-sectional view of yet another exemplary alternative cam locking feature.

FIGS. 21-23 show still further exemplary alternative components that may be incorporated into instrument (200) to actuate the staple driver and knife. In particular, FIGS. 21-23 show an exemplary alternative motor (710) and cam (720) configured to operate substantially similar to motor (510) and cam (520) discussed above except for the differences discussed below. Motor (710) and cam (720) are configured to drive a staple driver (not shown) distally and proximally through one revolution of cam (720) via translation of a driver actuator (764) and a follower interface feature (784).

As shown in FIG. 21, motor (710) is disposed within an actuator handle assembly (not shown) parallel to a proximal portion of driver actuator (764). Cam (720) is mounted eccentrically on a shaft (712) extending distally from motor (710). Actuation of motor (710) causes rotation of cam (720) about a longitudinal axis (LA6) defined by motor (710). As best seen in FIG. 19, a cam projection (722) is extends from a distal face (723) of cam (720).

Cam projection (722) comprises a first portion (724) and a second portion (726). First portion (724) and second portion (726) are disposed on opposite sides of cam projection (722). First portion (724) presents a portion of cam projection (722) having a radial distance from longitudinal axis (LA6) that is greater than a radial distance of second portion (726) from longitudinal axis (LA6). Cam projection (722) further comprises intermediate portions (725, 727) disposed between first portion (724) and second portion (726), Intermediate portions (725, 727) are contoured to provide a substantially smooth transition between first portion (724) and second portion (726) along opposite sides of cam projection (722). Thus, it should be understood that, relative to a fixed point in space, a radial distance from extrusion (722) to longitudinal axis (LA6) will change from the lesser radial distance presented by second portion (726) to the greater radial distance presented by first portion (724); and back again as cam (720) is rotated through one revolution.

As shown in FIG. 21, follower interface feature (784) comprises a pivoting cam follower (790). The handle assembly comprises a pivot pin (772) to which cam follower (790) is rotatably coupled such that cam follower (790) is free to rotate about pivot pin (772). A first portion (792) of cam follower (790) is slidably engaged with cam projection (722). A free end of first portion (792) of cam follower (790) defines an engagement feature (791) configured to cause first portion (792) to remain engaged with cam projection (722) as cam (720) rotates. FIG. 23 shows one exemplary version of engagement feature (791). In particular, FIG. 23 shows cam projection (722) comprising a lip (721) projecting inwardly from cam projection (722). Engagement feature (791) is configured to couple about lip (721) and an exterior surface of cam projection (722) such that engagement feature (791) will remain coupled with cam projection (722) as cam (720) rotates. In particular, engagement feature (791) comprises a first finger (795A) disposed outside of cam projection (722) and a second finger (795B) disposed inside of cam projection (722). It should therefore be understood that as cam (720) is rotated through one revolution, a radial distance from engagement feature (791) to longitudinal axis (LA6) will change from the lesser radial distance caused by second portion (726) to the greater radial distance caused by first portion (724) and back again. This change of radial distance of engagement feature (791), and thus proximal end of first portion (792) of cam follower (790), will cause cam follower (790) to rotate about pivot pin (772) from a first position to a second position and back again.

As will be discussed in more detail below, first finger (795A) is operable to drive engagement feature (791) such that cam follower (790) rotates clockwise about pivot pin (772) to thereby drive follower interface feature (784), driver actuator (764), and the staple driver distally. As will also be discussed in more detail below, second finger (795B) is operable to drive engagement feature (791) such that cam follower (790) rotates counter-clockwise about pivot pin (772) to thereby retract follower interface feature (784), driver actuator (764), and the staple driver proximally.

A second portion (794) of cam follower (790) defines a slot (793). Follower interface feature (784) comprises a pin (789) extending laterally from follower interface feature (784). Pin (789) is slidably and rotatably disposed within slot (793) such that cam follower (790) is coupled with follower interface feature (784) and further such that, as cam follower (790) rotates about pivot pin (772), follower interface feature (784) translates longitudinally. As cam (720) is rotated through one revolution, the longitudinal position of follower interface feature (784) and driver actuator (764) will translate from a proximal position to a distal position as cam (720) completes 180° of rotation, caused by contact between first finger (795A) of engagement feature (791) and an exterior surface of cam projection (772) at first portion (724); and back again to the proximal position, caused by contact between second finger (795B) of engagement feature (791) and an interior surface of cam projection (772) at second portion (726) as cam (720) completes 360° of rotation. It should therefore be understood that as cam (720) is rotated through one revolution, cam follower (790) is rotated clockwise from a first position to a second position then rotated counter-clockwise from the second position to the first position; thus translating follower interface feature (784) from a first longitudinal position to a second longitudinal position and back again. This translation of follower interface feature (784) from a first longitudinal position to a second longitudinal position and back again will cause the staple driver and knife to be driven from a proximal position to a distal position and back again via driver actuator (764). Follower interface feature (784), driver actuator (764), and the staple driver will thus longitudinally translate from the proximal position to the distal position and back again in a single revolution of barrel cam (720). This translation of follower interface feature (784) from the proximal position to the distal position and back again will cause the staple driver and knife to be driven distally and proximally via driver actuator (764).

As best seen in FIG. 22, intermediate portion (725) and intermediate portion (727) have different contours. These different contours represent different rates of change of the radial distance from cam projection (722) to longitudinal axis (LA6) presented by first portion (724) to second portion (726) and vice versa. In particular, intermediate portion (725) represents a more gradual rate of change from the radial distance presented by second portion (726) to the radial distance presented by first portion (724) whereas intermediate portion (727) represents a more rapid rate of change from the radial distance presented by first portion (724) to the radial distance presented by second portion (726) or vice versa depending upon which direction in which cam (720) is rotated. It should be understood that these differing rates of change will be communicated to follower interface feature (784), driver actuator (764), and the staple driver via cam follower (790) thus causing differing rates of longitudinal translation of follower interface feature (784), driver actuator (764), and the staple driver. For instance, intermediate portion (725) may provide a relatively slow rate of distal advancement of driver actuator (764) while intermediate portion (727) provides a relatively rapid rate of proximal retraction of driver actuator (764). Of course, these rates may be further varied in any suitable way.

While the full 360° revolution of cam (720) is allocated as 180° for distal motion of driver actuator (764) and the remaining 180° for proximal motion of driver actuator, it should be understood that the allocation may be made in any other suitable fashion (e.g., 270° for distal motion and 90° for proximal motion, etc.). It should also be understood that a full range of distal and proximal travel may be provided by less than 360° of rotation of barrel cam (720).

Some versions of instrument (10) contain a breakable washer that is broken by the knife when the knife completes a full distal range of motion, as discussed above with reference to FIG. 42. It will further be understood that the configuration of cam projection (722) may provide an increasing mechanical advantage as the knife reaches the end of its distal movement, thereby providing greater force by which to break the washer and form the staples. Again, though, the breakable washer may be omitted entirely in some versions.

G. Seventh Exemplary Alternative Motor and Cam Assembly

Figure 24A:
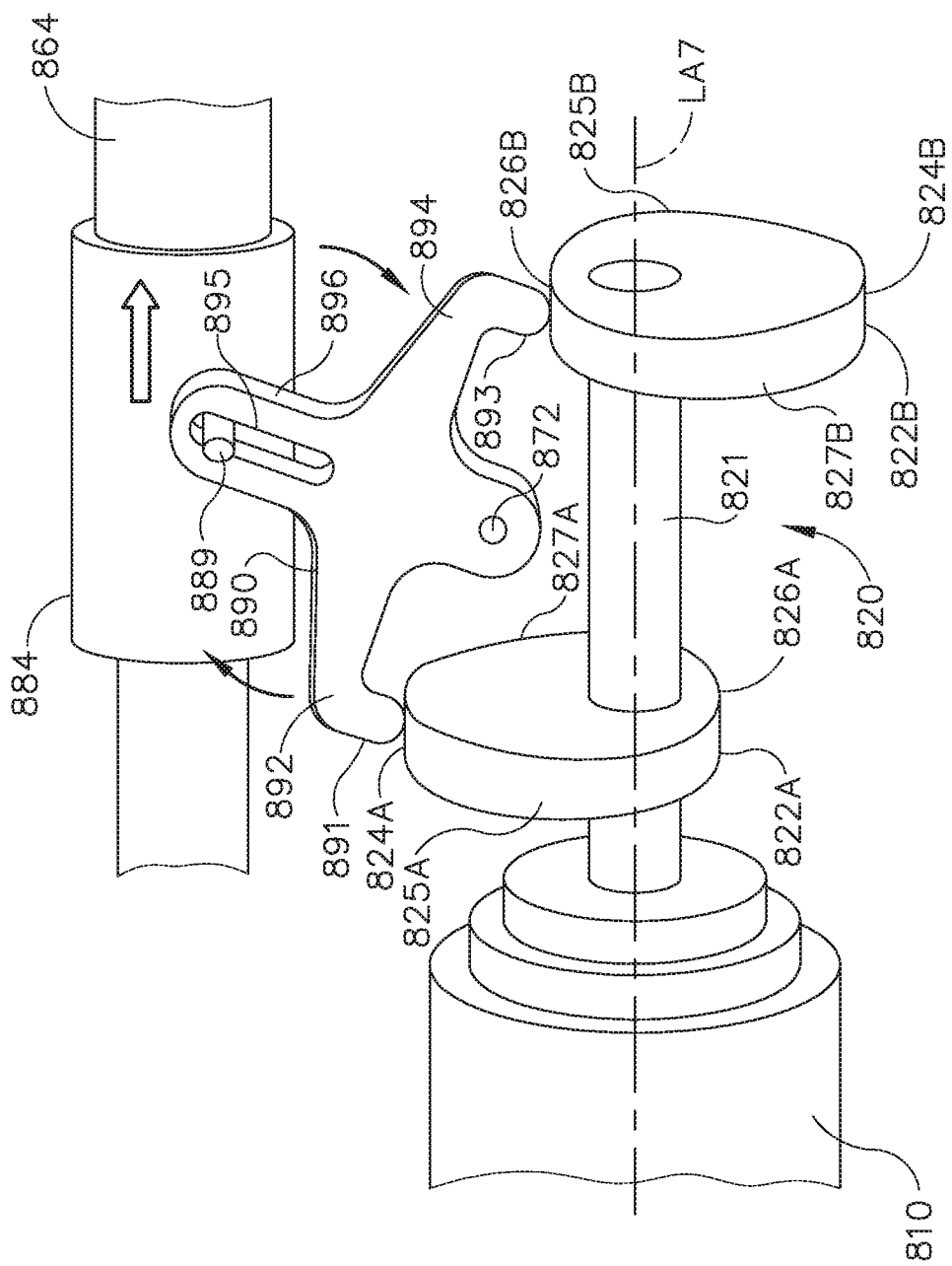
FIG. 24A depicts a perspective view of a motor and an exemplary multi-cam shaft that may be incorporated into the instrument of FIG. 7, in a first rotational position.
Figure 24B:
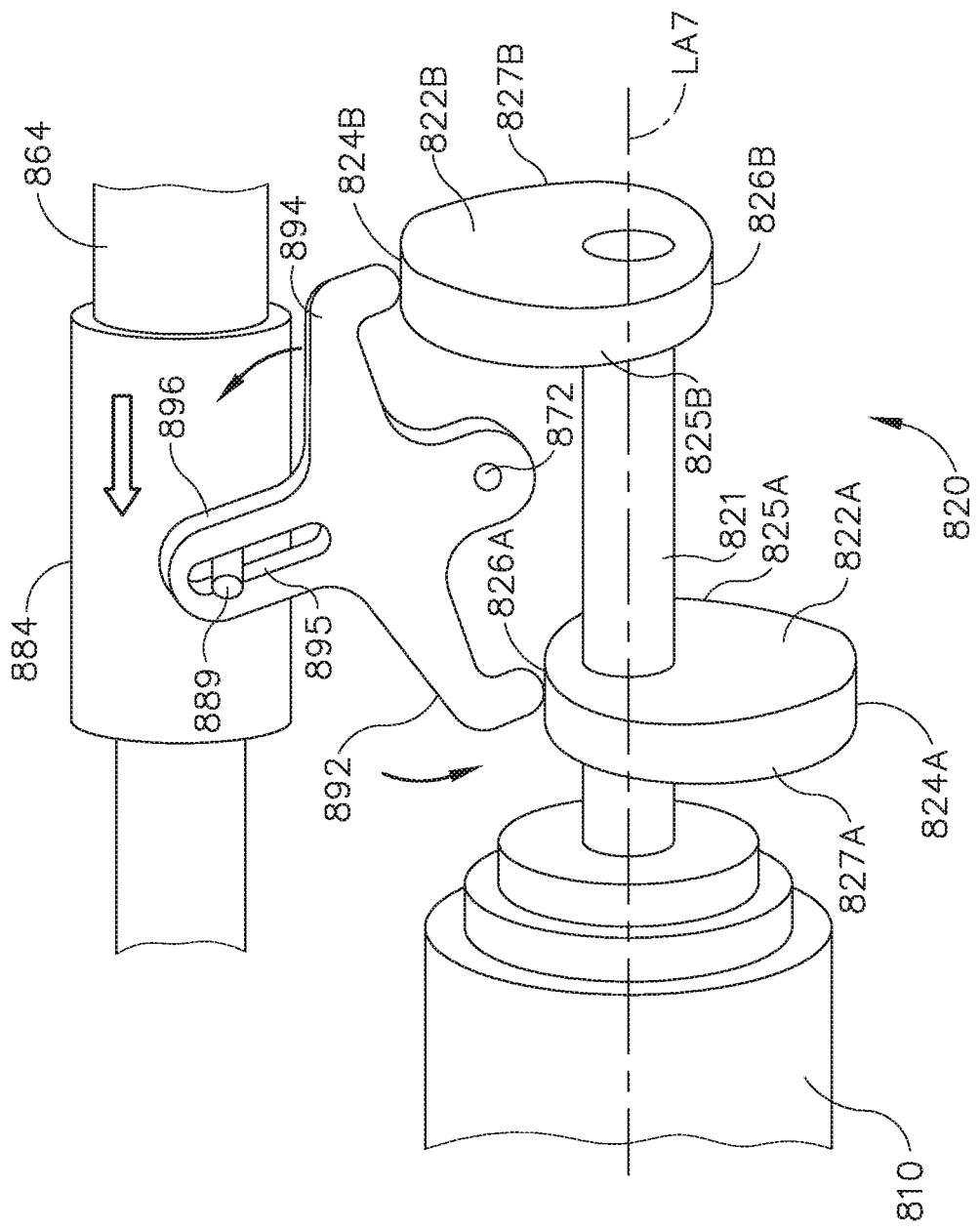
FIG. 24B depicts a perspective view of the motor and multi-cam shaft of FIG. 24A in a second rotational position.

FIGS. 24A-24B show yet additional exemplary alternative components that may be incorporated into instrument (200) to actuate the staple driver and knife. In particular, FIGS. 24A-24B show an exemplary alternative motor (810) and multi-cam assembly (820) configured to drive a staple driver (not shown) distally and proximally through one revolution of multi-cam assembly (820) via translation of a driver actuator (864) and a follower interface feature (884). Motor (810) is disposed within an actuator handle assembly (not shown) parallel to a proximal portion of a driver actuator (864). Multi-cam assembly (820) is coupled with a distal end of motor (810). Actuation of motor (810) causes rotation of multi-cam assembly (820) about a longitudinal axis (LA7) defined by motor (810). Multi-cam assembly (820) comprises a shaft (821) and a pair of cams (822A, 822B) secured to shaft (821) at different longitudinal positions along longitudinal axis (LA7). While cams (822A, 822B) are shown in FIGS. 24A-24B as being longitudinally spaced apart from each other along shaft (821), it should be understood that cams (822A, 822B) may instead be longitudinally adjacent to each other (e.g., such that there is no longitudinal gap between cams (822A, 822B)).

First cam (822A) comprises a first portion (824A) and a second portion (826A). First portion (824A) and second portion (826A) are disposed on radially opposite sides of first cam (822A). First portion (824A) presents a portion of first cam (822A) having a radial distance from longitudinal axis (LA7) that is greater than a radial distance of second portion (826A) from longitudinal axis (LA7). First cam (822A) further comprises intermediate portions (825A, 827A) disposed between first portion (824A) and second portion (826A). Intermediate portions (825A, 827A) are contoured to provide a substantially smooth transition between first portion (824A) and second portion (826A) along opposite sides of cam (822B). Thus, relative to a fixed point in space, a radial distance from first cam (822A) to longitudinal axis (LA7) will change from the greater radial distance presented by first portion (824A) to the lesser radial distance presented by second portion (826A); and back again as first cam (822A) is rotated through one revolution.

Second cam (822B) comprises a first portion (824B) and a second portion (826B). First portion (824B) and second portion (826B) are disposed on radially opposite sides of second cam (822B). First portion (824B) presents a portion of second cam (822B) having a radial distance from longitudinal axis (LA7) that is greater than a radial distance of second portion (826B) from longitudinal axis (LA7). Second cam (822B) further comprises intermediate portions (825B, 827B) disposed between first portion (824B) and second portion (826B). Intermediate portions (825B, 827B) are contoured to provide a substantially smooth transition between first portion (824B) and second portion (826B) along opposite sides of cam (822B). Thus, relative to a fixed point in space, a radial distance from second cam (822B) to longitudinal axis (LA7) will change from the greater radial distance presented by first portion (824B) to the lesser radial distance presented by second portion (826B); and back again as second cam (822B) is rotated through one revolution. While second cam (822B) has a 360° working profile in this example, it should be understood that the working profile of second cam (822B) need not necessarily be 360°.

As shown in FIGS. 24A-24B, first cam (822A) and second cam (822B) are oriented such that first portion (824A) of first cam (822A) and first portion (824B) of second cam (822B) are at different angular positions relative to shaft (821) of multi-cam assembly (820). In particular, in the present example, first cam (822A) and second cam (822B) are oriented such that first portion (824A) of first cam (822A) and first portion (824B) of second cam (822B) are at angular positions 180° from one another about shaft (821). Further, first cam (822A) and second cam (822B) are oriented such that second portion (826A) of first cam (822A) and second portion (826B) of second cam (822B) are at opposing angular positions about shaft (821). In particular, in the present example, first cam (822A) and second cam (822B) are oriented such that second portion (826A) of first cam (822A) and first portion (826B) of second cam (822B) are at angular positions 180° from one another about shaft (821). Of course, any other suitable relationships may be used.

As shown in FIGS. 24A-24B, follower interface feature (884) comprises a pivoting cam follower (890). The handle assembly comprises a pivot pin (872) to which cam follower (890) is rotatably coupled such that cam follower (890) is free to rotate about pivot pin (872). A proximal end of a first portion (892) comprises a downwardly extending projection (891). Projection (891) of first portion (892) is in contact with first cam (822A) at a top of first cam (822A) directly vertical of longitudinal axis (LA7). A distal end of a second portion (894) comprises a downwardly extending projection (893). Projection (893) of second portion (894) is in contact with second cam (822B) at a top of second cam (822B) directly vertical of longitudinal axis (LA7). Thus, it should be understood that as multi-cam assembly (820) is rotated through one revolution, a radial distance from the proximal end of first portion (892) of cam follower (890) to longitudinal axis (LA7) will change from the greater radial distance caused by first portion (824A) to the lesser radial distance caused by second portion (826B) and back again; while at the same time, a radial distance from the distal end of second portion (894) of cam follower (890) to longitudinal axis (LA7) will change from the lesser radial distance caused by first portion (826B) to the greater radial distance caused by first portion (826A) and back again This change of radial distances of first portion (892) and second portion (894) of cam follower (890), will cause cam follower (890) to rotate about pivot pin (872) from a first position to a second position and back again as shaft (821) rotates through a full revolution.

A third portion (896) of cam follower (890) presents a slot (895). Follower interface feature (884) comprises a pin (889) extending laterally from follower interface feature (884). Pin (889) is slidably and rotatably disposed within slot (895) such that cam follower (890) is coupled with follower interface feature (884) and further such that, as cam follower (890) rotates about pivot pin (872), follower interface feature (884) translates longitudinally. It should therefore be understood that, as multi-cam assembly (820) is rotated through one revolution, cam follower (890) is rotated from a first position to a second position then back to the first position; thus translating follower interface feature (884) from a first longitudinal position to a second longitudinal position and back again. This translation of follower interface feature (884) from a first longitudinal position to a second longitudinal position and back again will cause the staple driver to be driven from a proximal position to a distal position and back again via driver actuator (864).

Intermediate portions (825A, 825B) and intermediate portions (827A, 827B) may have different contours. For instance, these different contours may represent different rates of change of the radial distance from the exterior surfaces of cams (822A, 822B) to longitudinal axis (LA7) presented by first portions (824A, 824B) to second portions (826A, 826B) and vice versa. In particular, intermediate portions (825A, 825B) may represent a more gradual rate of change from the radial distance presented by second portions (826A, 826B) to the radial distance presented by first portions (824A, 824B) whereas intermediate portions (827A, 827B) may represent a more rapid rate of change from the radial distance presented by first portions (824A, 824B) to the radial distance presented by second portions (826A, 826B) or vice versa depending upon which direction in which cams (822A, 822B) are rotated. These differing rates of change will be communicated to follower interface feature (884), driver actuator (864), and the staple driver via cam follower (890), thus causing differing rates of longitudinal translation of follower interface feature (884), driver actuator (864), and the staple driver. For instance, intermediate portions (825A, 825B) may provide a relatively slow rate of distal advancement of driver actuator (864) while intermediate portion (827A, 827B) provides a relatively rapid rate of proximal retraction of driver actuator (864). Of course, these rates may be further varied in any suitable way.

While the full 360° revolution of multi-cam assembly (820) is allocated as 180° for distal motion of driver actuator (864) and the remaining 180° for proximal motion of driver actuator, it should be understood that the allocation may be made in any other suitable fashion (e.g., 270° for distal motion and 90° for proximal motion, etc.). It should also be understood that a full range of distal and proximal travel may be provided by less than 360° of rotation of multi-cam assembly (820).

Some versions of instrument (10) contain a breakable washer that is broken by the knife when the knife completes a full distal range of motion, as discussed above with reference to FIG. 42. It will further be understood that the configuration of first portion (824A) of first cam (822A) may provide an increasing mechanical advantage as the knife reaches the end of its distal movement, thereby providing greater force by which to break the washer and form the staples. Again, though, the breakable washer may be omitted entirely in some versions.

H. Eighth Exemplary Alternative Motor and Cam Assembly

Figure 25A:
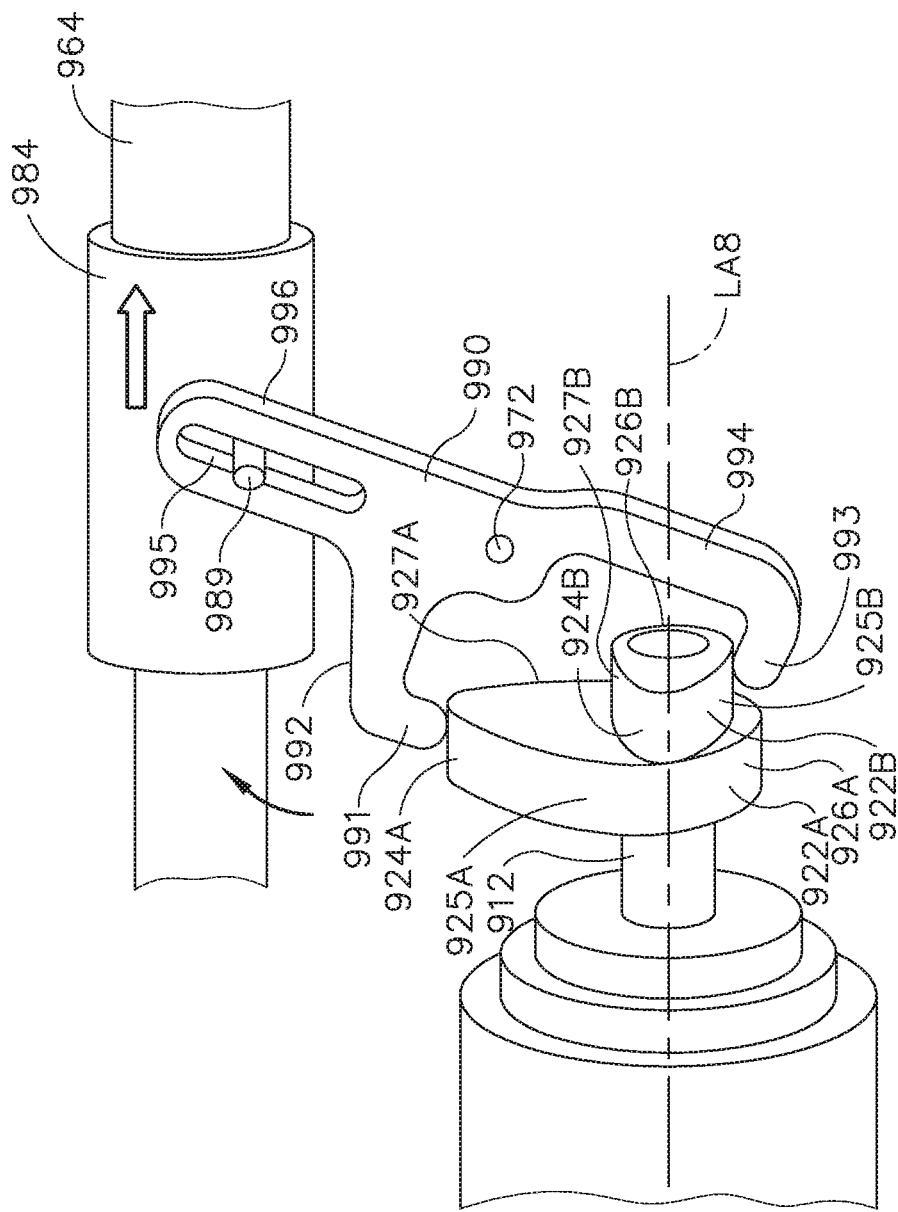
FIG. 25A depicts a perspective view of a motor and an exemplary alternative multi-cam shaft that may be incorporated into the instrument of FIG. 7, in a first rotational position.
Figure 25B:
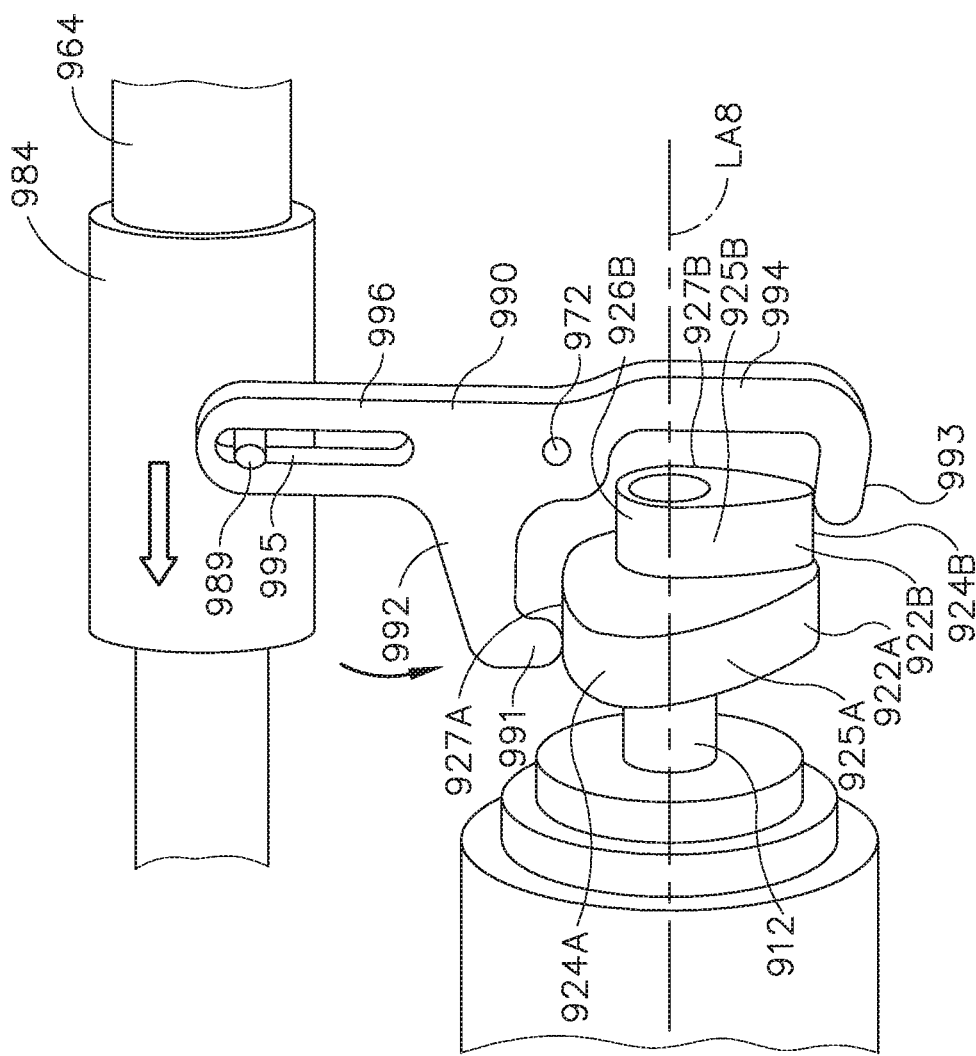
FIG. 25B depicts a perspective view of the motor and multi-cam shaft of FIG. 25A in a second rotational position.

FIGS. 25A-26B show additional exemplary alternative components that may be incorporated into instrument (200) to actuate the staple driver and knife. In particular, FIGS. 25A-25B show an exemplary alternative motor (910) and multi-cam assembly (920) configured to operate substantially similar to motor (810) and multi-cam assembly (820) discussed above except for the differences discussed below. Motor (910) and multi-cam assembly (920) are configured to drive a staple driver (not shown) distally and proximally through one revolution of multi-cam assembly (920) via translation of a driver actuator (964) and a follower interface feature (984). Motor (910) is disposed within an actuator handle assembly (not shown) parallel to a proximal portion of a driver actuator (964). Multi-cam assembly (920) is coupled with a shaft (912) projecting from a distal end of motor (910). Actuation of motor (910) causes rotation of multi-cam assembly (920) about a longitudinal axis (LA8) defined by motor (910).

Multi-cam assembly (920) comprises a pair of cams (922A, 922B) secured to shaft (912) at different longitudinal positions along longitudinal axis (LA8). First cam (922A) comprises a first portion (924A) and a second portion (926A). First portion (924A) and second portion (926A) are disposed on radially opposite sides of first cam (922A). First portion (924A) presents a portion of first cam (922A) having a radial distance from longitudinal axis (LA8) that is greater than a radial distance of second portion (926A) from longitudinal axis (LA8). First cam (922A) further comprises intermediate portions (925A, 927A) disposed between first portion (924A) and second portion (926A). Intermediate portions (925A, 927A) are contoured to provide a substantially smooth transition between first portion (924A) and second portion (926A) along opposite sides of cam (922B). Thus, relative to a fixed point in space, a radial distance from first cam (922A) to longitudinal axis (LA7) will change from the greater radial distance presented by first portion (924A) to the lesser radial distance presented by second portion (926A); and back again as first cam (922A) is rotated through one revolution.

Second cam (922B) comprises a first portion (924B) and a second portion (926B). First portion (924B) and second portion (926B) are disposed on radially opposite sides of second cam (922B). First portion (924B) presents a portion of second cam (922B) having a radial distance from longitudinal axis (LA8) that is greater than a radial distance of second portion (926B) from longitudinal axis (LA8), Second cam (922B) further comprises intermediate portions (925B, 927B) disposed between first portion (924B) and second portion (926B). Intermediate portions (925B, 927B) are contoured to provide a substantially smooth transition between first portion (924B) and second portion (926B) along opposite sides of cam (922B). Thus, relative to a fixed point in space, a radial distance from second cam (922B) to longitudinal axis (LA8) will change from the greater radial distance presented by first portion (924B) to the lesser radial distance presented by second portion (926B); and back again as second cam (922B) is rotated through one revolution.

As best seen in FIGS. 26A-26B, first cam (922A) and second cam (922B) are oriented such that first portion (924A) of first cam (922A) and first portion (924B) of second cam (922B) are at different angular positions relative to shaft (912) of multi-cam assembly (920). In particular, in the present example, first cam (922A) and second cam (922B) are oriented such that first portion (924A) of first cam (922A) and first portion (924B) of second cam (922B) are at angular positions 90° from one another about shaft (912). Also, first cam (922A) and second cam (922B) are oriented such that second portion (926A) of first cam (922A) and first portion (926B) of second cam (922B) are at angular positions 90° from one another about to shaft (912). First cam (922A) and second cam (922B) are also differently sized.

As shown in FIGS. 26A-26B, follower interface feature (984) comprises a pivoting cam follower (990). The handle assembly comprises a pivot pin (972) to which cam follower (990) is rotatably coupled such that cam follower (990) is free to rotate about pivot pin (972). A proximal end of a first portion (992) comprises a downwardly extending projection (991). Projection (991) of first portion (992) is in contact with first cam (922A) at a top of first cam (922A) directly vertical of longitudinal axis (LA8). A distal end of a second portion (993) comprises a downwardly extending projection (993). Projection (993) of second portion (994) is in contact with second cam (922B) at a bottom of second cam (922B) directly vertical of longitudinal axis (LA8). Thus, it should be understood that as multi-cam assembly (920) is rotated through one revolution, a radial distance from projection (991) of cam follower (990) to longitudinal axis (LA8) will change from the greater radial distance caused by first portion (924A) to the lesser radial distance caused by second portion (926B) and back again; while at the same time, a radial distance from projection (993) of cam follower (990) to longitudinal axis (LA8) will change from the lesser radial distance caused by first portion (926B) to the greater radial distance caused by first portion (926A) and back again. This change of radial distances of first portion (992) and second portion (994) of cam follower (990), will cause cam follower (990) to rock about pivot pin (972) from a first position to a second position and back again as shaft (912) completes on full revolution.

A third portion (996) of cam follower (990) defines a slot (995). Follower interface feature (984) comprises a pin (989) extending laterally from follower interface feature (984). Pin (989) is slidably and rotatably disposed within slot (995) such that cam follower (990) is coupled with follower interface feature (984) and further such that, as cam follower (990) rotates about pivot pin (972), follower interface feature (984) translates longitudinally. It should therefore be understood that as multi-cam assembly (920) is rotated through one revolution, cam follower (990) is rotated from a first position to a second position and then back to the first position; thus translating follower interface feature (984) from a first longitudinal position to a second longitudinal position and back again. This translation of follower interface feature (984) from a first longitudinal position to a second longitudinal position and back again will cause the staple driver to be driven from a proximal position to a distal position and back again via driver actuator (964).

As shown in FIGS. 26A-26B, intermediate portions (925A, 925B) and intermediate portions (927A, 927B) may have different contours. These different contours represent different rates of change of the radial distance from the exterior surfaces of cams (922A, 922B) to longitudinal axis (LA7) presented by first portions (924A, 924B) to second portions (926A, 926B) and vice versa. In particular, intermediate portions (925A, 925B) represent a more gradual rate of change from the radial distance presented by second portions (926A, 926B) to the radial distance presented by first portions (924A, 924B) whereas intermediate portions (927A, 927B) represent a more rapid rate of change from the radial distance presented by first portions (924A, 924B) to the radial distance presented by second portions (926A, 926B) or vice versa depending upon which direction in which cams (922A, 922B) are rotated. It should be understood that, these differing rates of change will be communicated to follower interface feature (984), driver actuator (964), and the staple driver via cam follower (990) thus causing differing rates of longitudinal translation of follower interface feature (984), driver actuator (964), and the staple driver. For instance, intermediate portions (925A, 925B) may provide a relatively slow rate of distal advancement of driver actuator (964) while intermediate portion (927A, 927B) provides a relatively rapid rate of proximal retraction of driver actuator (964). Of course, these rates may be further varied in any suitable way.

While the full 360° revolution of multi-cam assembly (920) is allocated as 180° for distal motion of driver actuator (964) and the remaining 180° for proximal motion of driver actuator, it should be understood that the allocation may be made in any other suitable fashion (e.g., 270° for distal motion and 90° for proximal motion, etc.). It should also be understood that a full range of distal and proximal travel may be provided by less than 360° of rotation of multi-cam assembly (920).

Some versions of instrument (10) contain a breakable washer that is broken by the knife when the knife completes a full distal range of motion, as discussed above with reference to FIG. 42. It will further be understood that the configuration of first portion (924A) of first cam (922A) may provide an increasing mechanical advantage as the knife reaches the end of its distal movement, thereby providing greater force by which to break the washer and form the staples. Again, though, the breakable washer may be omitted entirely in some versions.

III. Exemplary Motorized Circular Surgical Stapling Instrument with Oblique Pistol Grip Although the examples discussed above comprise a motor disposed within an actuator handle assembly at an orientation that is parallel to a proximal portion of a driver actuator, it should be understood that the motor may be disposed at various other orientations. The examples described below include motors being oriented obliquely relative to a proximal portion of a driver actuator. It should be understood that the following examples are merely illustrative. Various other suitable ways in which a motor may be oriented obliquely (or otherwise non-parallel) relative to the proximal portion of a driver actuator will be apparent to those of ordinary skill in the art in view of the teachings herein.

A. Bevel Gear Drive Train Adapter for Oblique Motor

Figure 27:
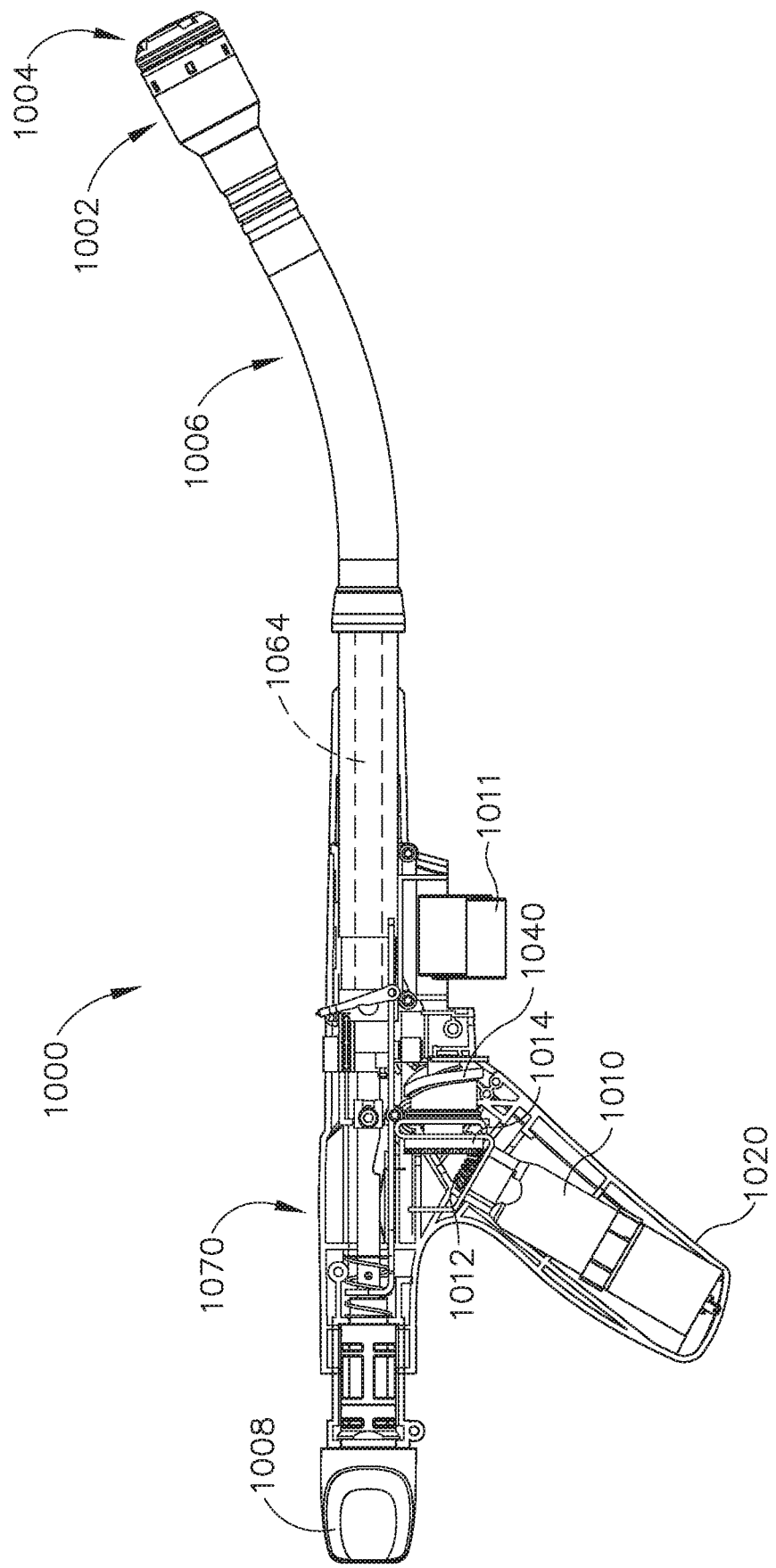
FIG. 27 depicts a side elevational view of yet another exemplary alternative circular stapling surgical instrument having an obliquely oriented motor.

FIG. 27 shows an exemplary alternative circular surgical stapling instrument (1000). Instrument (1000) of this example is substantially similar to instrument (10) described above, in that instrument (1000) includes a stapling head assembly (1002) similar to stapling head assembly (20), an anvil (1004) similar to anvil (40), and a knob (1008) similar to knob (98). Instrument (1000) also includes a curved shaft assembly (1006), which is substantially similar to shaft assembly (60) except that shaft assembly (1006) is curved while shaft assembly (60) is straight. Unlike instrument (10), instrument (1000) of this example includes a handle assembly (1070) that defines an obliquely oriented pistol grip (1020). Also unlike instrument (10), instrument (1000) of this example includes a motor (1010) disposed within pistol grip (1020). Motor (1010) and pistol grip (1020) are both oriented obliquely, relative to a longitudinal axis defined by a driver actuator (1064). Driver actuator (1064) translates within shaft assembly (1006) to actuate stapling head assembly (1002), such that driver actuator (1064) operates similar to driver actuator (64) discussed above. A battery pack (1011) is integral with handle assembly (1070) to provide power to motor (1010), though it should be understood that motor (1010) may instead be powered by a remote source in some other versions.

A first bevel gear (1012) is secured to an integral drive shaft of motor (1010) such that rotation of motor (1010) causes rotation of bevel gear (1012). A second bevel gear (1014) is secured to a proximal end of a cam (1040). Cam (1040) is further coupled with driver actuator (1064) such that rotation of cam (1040) causes longitudinal translation of driver actuator (1064). Bevel gears (1012, 1014) are oriented on axes of rotation that are oblique relative to each other. First bevel gear (1012) and second bevel gear (1014) engage such that rotation of first bevel gear (1012) causes rotation of second bevel gear (1014). It should therefore be understood that activation of motor (1010) causes rotation of cam (1040), and thereby translation of driver actuator (1064), via oblique meshing of bevel gears (1012, 1014). Cam (1040) of the present example may be configured in accordance with any of the cams (220, 320, 420, 520, 620, 720) and/or cam assemblies (820, 920) discussed above. Bevel gears (1012, 1014) may thus be viewed as serving as a drive adapter between obliquely oriented motor (1010) and cams (220, 320, 420, 520, 620, 720) and/or cam assemblies (820, 920) discussed above. It should be understood that the orientation shown in FIG. 27 is merely exemplary. Motor (1010) and/or pistol grip (1020) may have any other suitable orientation as will be apparent to those of ordinary skill in the art in view of the teachings herein.

B. Multi-Cam Assembly for Oblique Motor

Figure 28:
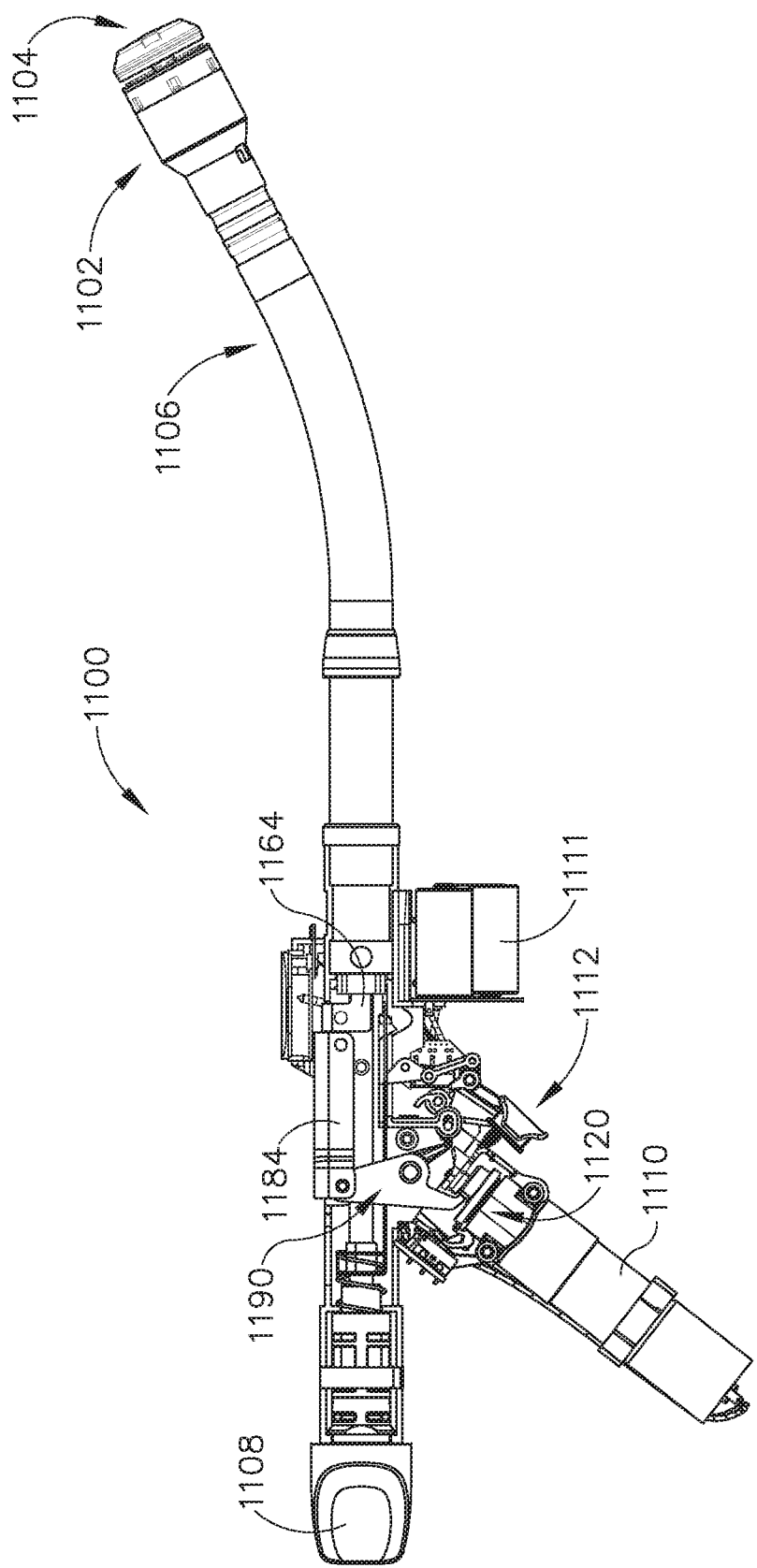
FIG. 28 depicts a side elevational view of yet another exemplary alternative circular stapling surgical instrument having an obliquely oriented motor.

FIG. 28 shows another alternative circular surgical stapling instrument (1100). Instrument (1100) of this example is substantially similar to instrument (10) described above, in that instrument (1100) includes a stapling head assembly (1102) similar to stapling head assembly (20), an anvil (1104) similar to anvil (40), and a knob (1108) similar to knob (98). Instrument (1100) also includes a curved shaft assembly (1106), which is substantially similar to shaft assembly (60) except that shaft assembly (1106) is curved while shaft assembly (60) is straight. Unlike instrument (10), instrument (11100) of this example includes handle assembly (not shown) that defines an obliquely oriented pistol grip (not shown). Such a handle assembly and pistol grip may be configured just like handle assembly 1070) and pistol grip (1020) described above. Also unlike instrument (10), instrument (1100) of this example includes a motor (1110) disposed within the pistol grip. Motor (1110) and the pistol grip are both oriented obliquely, relative to a longitudinal axis defined by a driver actuator (1164), Driver actuator (1164) translates within shaft assembly (1106) to actuate stapling head assembly (1102), such that driver actuator (1164) operates similar to driver actuator (64) discussed above. A battery pack (1111) is integral with the handle assembly to provide power to motor (1110), though it should be understood that motor (1110) may instead be powered by a remote source in some other versions.

A firing trigger and safety trigger assembly (1112) is coupled with the handle assembly, and is operable to selectively activate motor (1110). By way of example only, firing trigger and safety trigger assembly (1112) may be configured in accordance with at least some of the teachings of U.S. patent application Ser. No. 14/033,751, entitled CONTROL FEATURES FOR MOTORIZED SURGICAL STAPLING INSTRUMENT, filed on Sep. 23, 2013, now U.S. Pat. No. 9,907,552, issued Mar. 6, 2018, the disclosure of which is incorporated by reference herein. Instrument (1100) may also include a start switch and stop switch configured in accordance with at least some of the teachings of U.S. patent application Ser. No. 14/033,751, entitled CONTROL FEATURES FOR MOTORIZED SURGICAL STAPLING INSTRUMENT, filed on Sep. 23, 2013, now U.S. Pat. No. 9,907,552, issued Mar. 6, 2018, the disclosure of which is incorporated by reference herein. Other suitable variations of a firing trigger and safety trigger assembly (1112), as well as a start and stop switch, will be apparent to those of ordinary skill in the art in view of the teachings herein. It should also be understood that any of the other stapling instruments described herein may include a firing trigger and safety trigger assembly (1112) and/or start and stop switches configured in accordance with at least some of the teachings of U.S. patent application Ser. No. 14/033,751, entitled CONTROL FEATURES FOR MOTORIZED SURGICAL STAPLING INSTRUMENT, filed on Sep. 23, 2013, now U.S. Pat. No. 9,907,552, issued Mar. 6, 2018, the disclosure of which is incorporated by reference herein.

Figure 29:
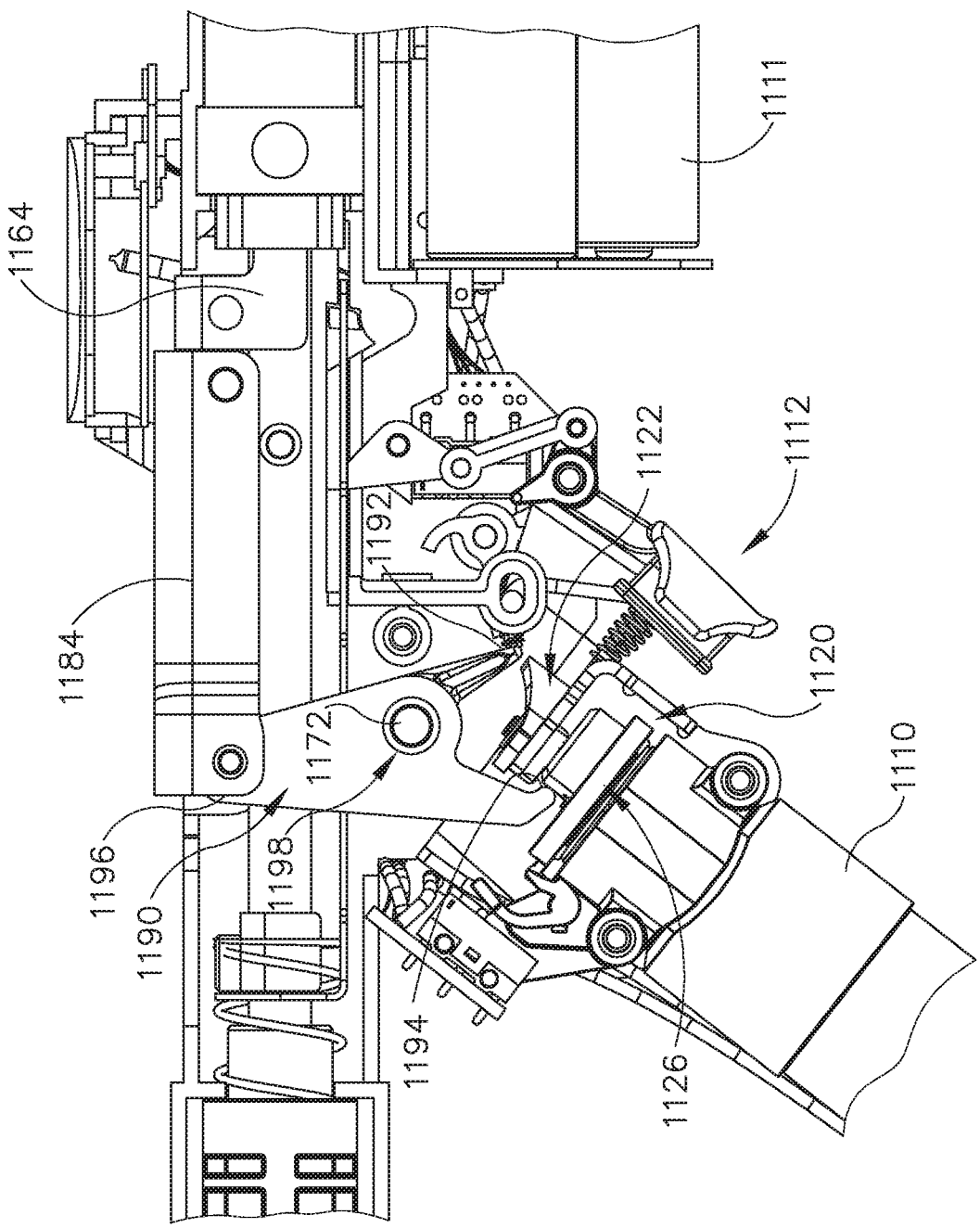
FIG. 29 depicts an enlarged side elevational view of a multi-cam drive assembly of the instrument of FIG. 28.
Figure 30:
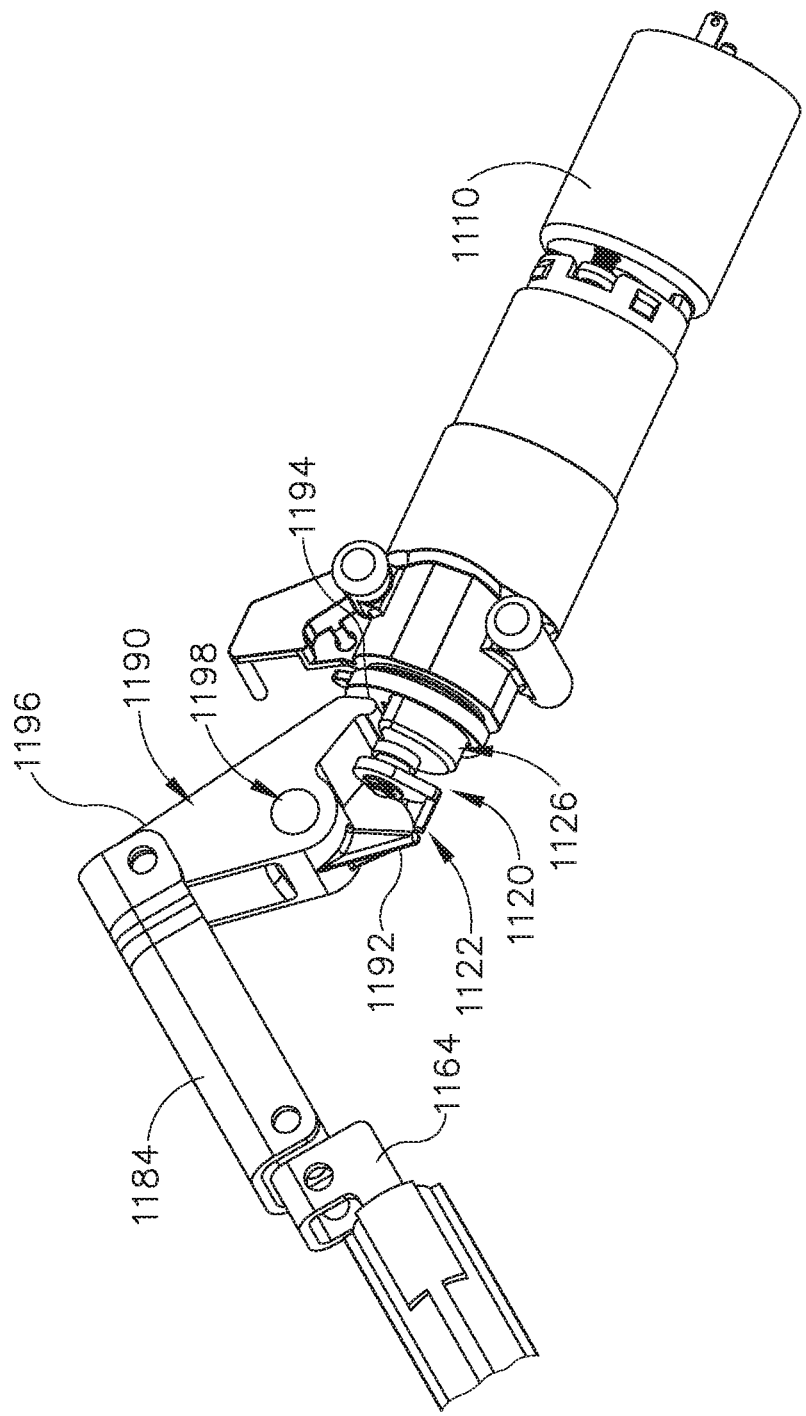
FIG. 30 depicts a perspective view of the multi-cam drive assembly of FIG. 29.
Figure 31:
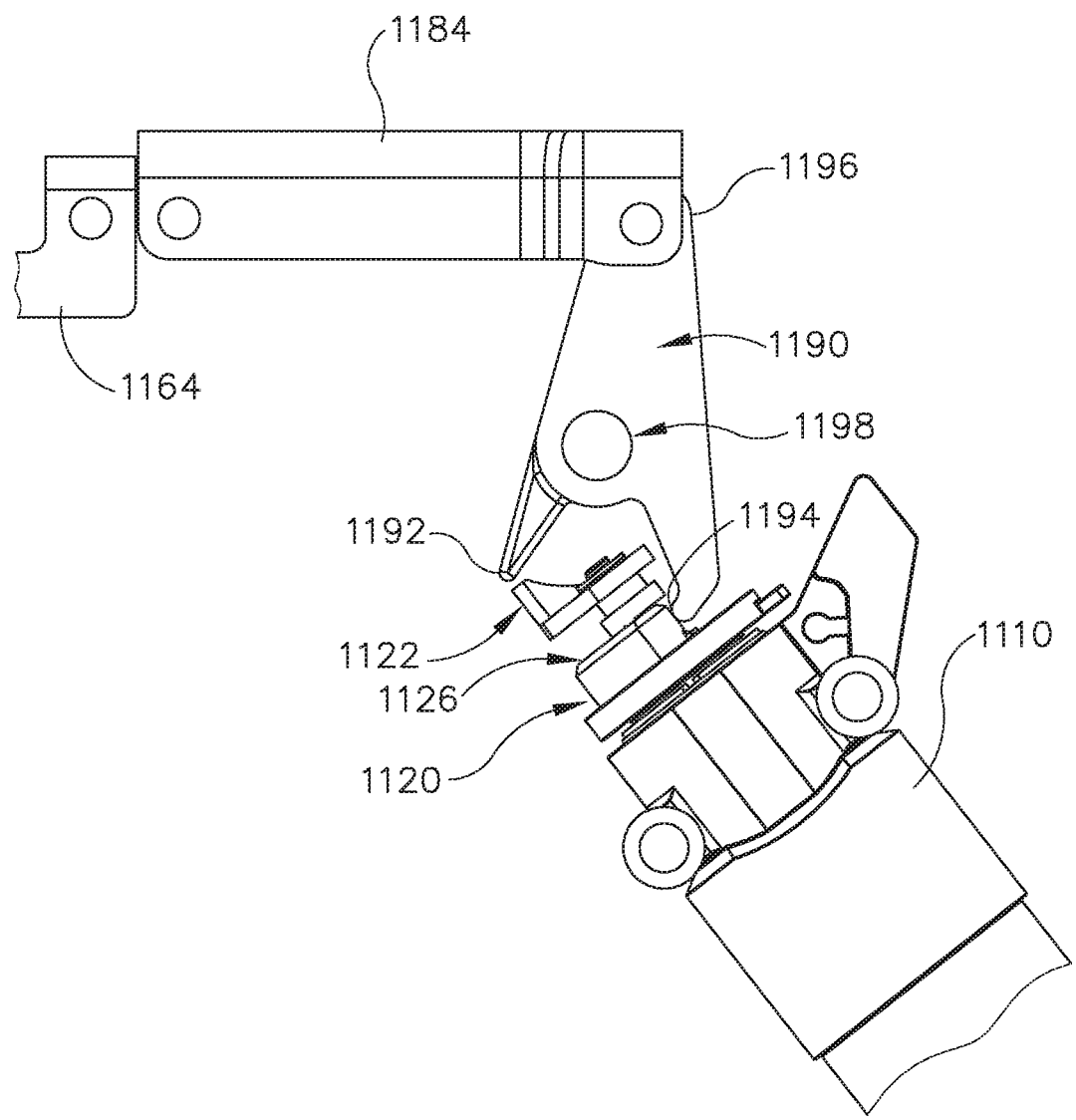
FIG. 31 depicts another enlarged side elevational view of the multi-cam drive assembly of FIG. 29.

As best seen in FIGS. 29-31, motor (1110) is coupled with a multi-cam assembly (1120), such that activation of motor (1110) will rotate multi-cam assembly (1120) about an axis that extends longitudinally through the center of motor (1110) and through the center of multi-cam assembly (1120). Multi-cam assembly (1120) is engaged with a pivoting cam follower (1190), which is pivotally coupled with the handle assembly. In particular, cam follower (1190) includes a pivot opening (1198), in which a pivot pin (1172) is disposed. Cam follower (1190) is thus pivotable about a longitudinal axis defined by pivot pin (1172). Cam follower (1190) is also pivotally coupled with a follower interface feature (1184), which is further coupled with driver actuator (1164). As will be described in further detail below, as multi-cam assembly (1120) is rotated by motor (1110) through a first range of angular motion, cam follower (1190) will pivot in a first direction (clockwise in the view shown in FIG. 29; counterclockwise in the view shown in FIG. 31), thereby driving follower interface feature (1184) and driver actuator (1164) distally. This distal motion will drive a knife and staples through tissue that is captured between stapling head assembly (1102) and anvil (1104), as described above. As multi-cam assembly (1120) is rotated by motor (1110) through a second range of angular motion, cam follower (1190) will pivot in a second direction (counterclockwise in the view shown in FIG. 29; clockwise in the view shown in FIG. 31), thereby driving follower interface feature (1184) and driver actuator (1164) proximally. This proximal motion will retract the knife back into stapling head assembly (1102).

Figure 32:
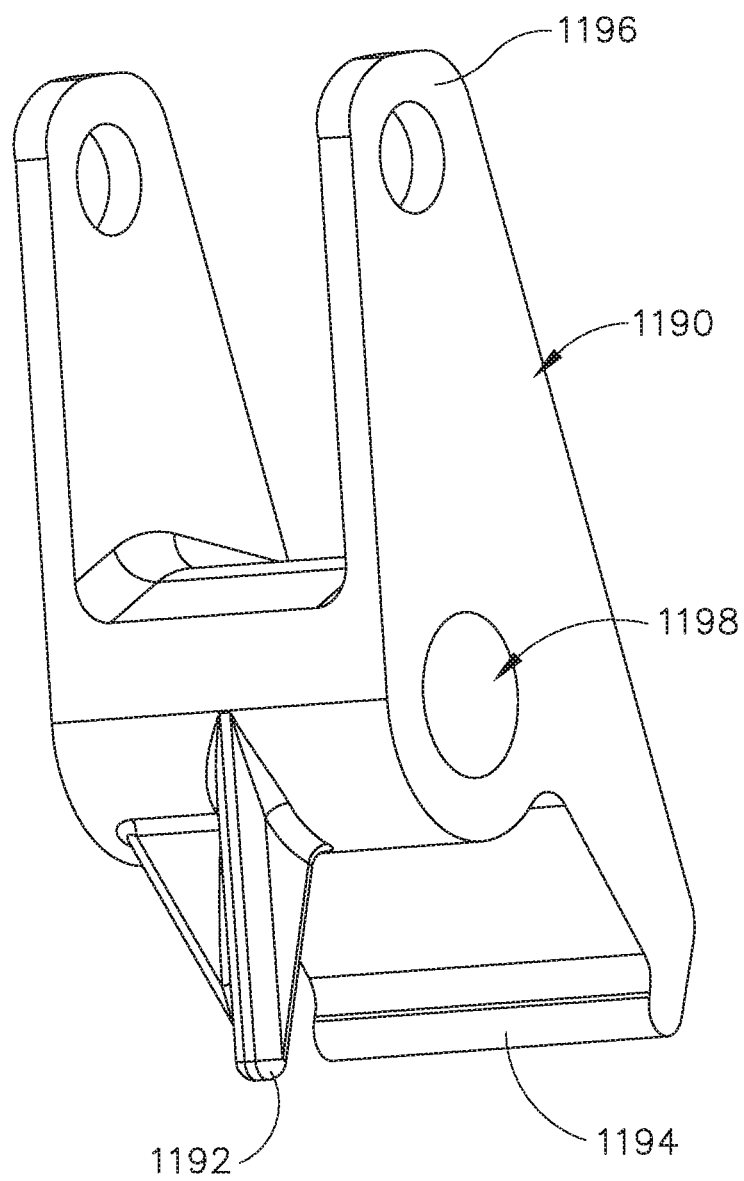
FIG. 32 depicts a perspective view of a cant follower of the multi-cam drive assembly of FIG. 29.

FIG. 32 shows cam follower (1190) in greater detail, Cam follower (1190) includes a first projection (1192), a second projection (1194), and a coupling end (1196). Projections (1192, 1194) are engaged with multi-cam assembly (1120) as will be described in greater detail below. Coupling end (1196) is pivotally coupled with follower interface feature (1184).

Figure 33:
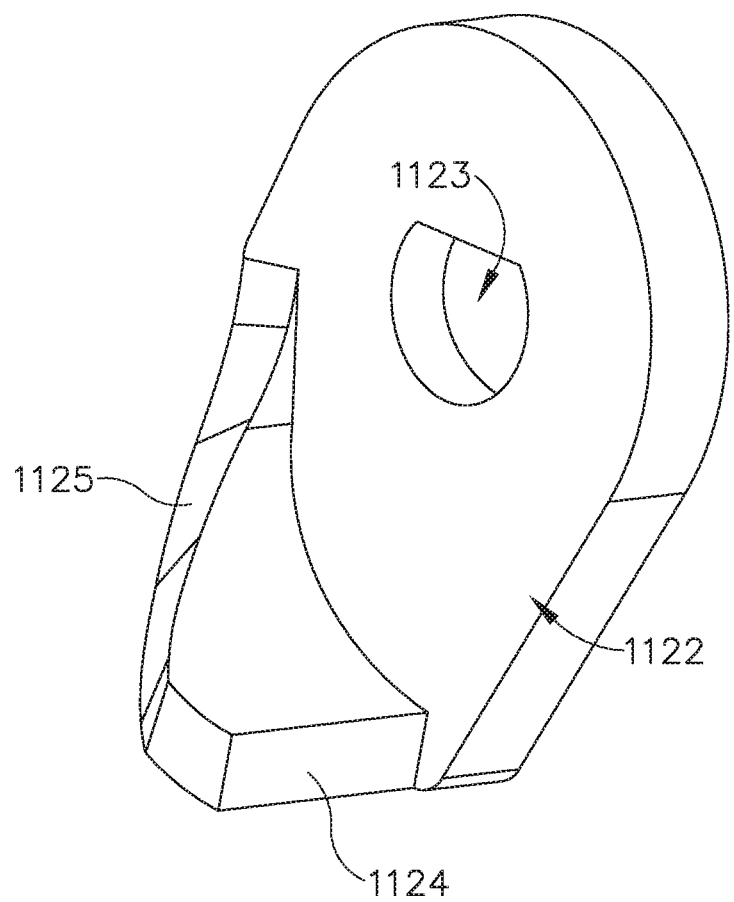
FIG. 33 depicts a perspective view of a first cam of the multi-cam drive assembly of FIG. 29.

Multi-cam assembly (1120) includes a first cam member (1122) and a second cam member (1126). As best seen in FIG. 33, first cam member (1122) defines an opening (1123) that is configured to receive a drive shaft (not shown) of motor (1110). First cam member (1122) also includes a distally projecting cam feature (1124) that includes a contoured ramp (1125). Cam feature (1124) is configured to engage first projection of cam follower (1190) while multi-cam assembly (1120) rotates through the second range of angular motion, thereby driving follower interface feature (1184) and driver actuator (1164) proximally from a distal position to a proximal position.

Figure 34:
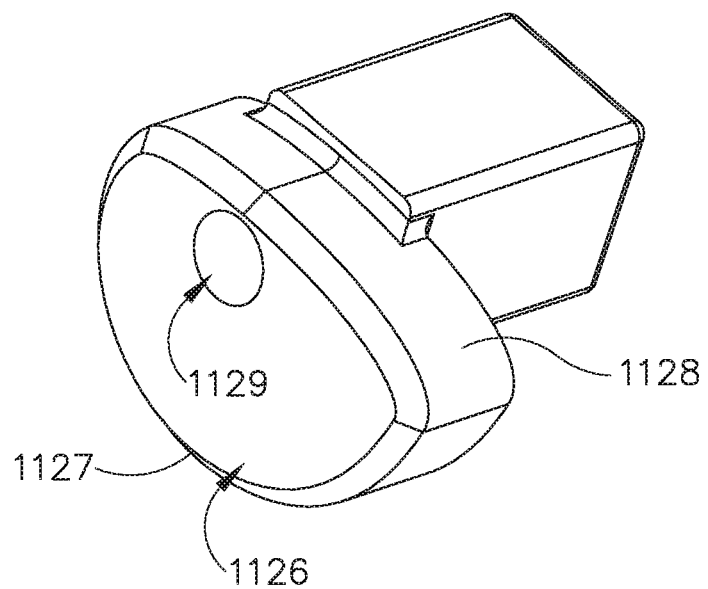
FIG. 34 depicts a perspective view of a second cam of the multi-cam drive assembly of FIG. 29.

As best seen in FIG. 34, second cam member (1126) defines an opening (1129) that is configured to receive the drive shaft of motor (1110). It should therefore be understood that openings (1123, 1129) of cam members (1122, 1126) are aligned with each other along the drive shaft of motor (1110). Second cam member (1126) also includes a laterally presented curved cam surface (1127) and a laterally presented substantially flat cam surface (1128). Curved cam surface (1127) is configured to engage second projection (1194) of cam follower (1190) while multi-cam assembly (1120) rotates through the first range of angular motion, thereby driving follower interface feature (1184) and driver actuator (1164) distally from a proximal position to a distal position. As multi-cam assembly (1120) rotates through the second range of angular motion, substantially flat cam surface (1128) provides clearance for second projection (1194), allowing cam follower (1190) to pivot as cam follower (1190) pulls follower interface feature (1184) and driver actuator (1164) proximally from a distal position to a proximal position.

In view of the foregoing, it should be understood that curved cam surface (1127) of second cam member (1126) drives driver actuator (1164) distally by bearing against second projection (1194) of cam follower (1190), thereby actuating stapling head assembly (1102); while cam feature (1124) of first cam member (1122) drives driver actuator (1164) proximally by bearing against first projection (1192) of cam follower (1190). Multi-cam assembly (1120) is thus operable to advance and retract driver actuator (1164) by rotating through a single revolution. In some other versions, multi-cam assembly (1120) is operable to advance and retract driver actuator (1164) by rotating through less than a single revolution. In the present example, the first angular range of motion of multi-cam assembly (1120), associated with advancement of driver actuator (1164), is a first 180°; while the second angular range of motion of multi-cam assembly (1120), associated with retraction of driver actuator (1164), is a second 180°. In some other versions, the first angular range of motion of multi-cam assembly (1120), associated with advancement of driver actuator (1164), is approximately 270°; while the second angular range of motion of multi-cam assembly (1120), associated with retraction of driver actuator (1164), is approximately 90°. Other suitable angular ranges of motion will be apparent to those of ordinary skill in the art in view of the teachings herein. In other words, the allocation of distal motion and proximal motion based on rotation of multi-cam assembly (1120) may be made in any other suitable fashion. It should also be understood that a full range of distal and proximal travel may be provided by less than 360° of rotation of multi-cam assembly (1120).

Some versions of anvil (1104) contain a breakable washer that is broken by the knife when the knife completes a full distal range of motion, as discussed above with reference to FIG. 42. It will further be understood that the configuration of curved cam surface (1127) may provide an increasing mechanical advantage as the knife reaches the end of its distal movement, thereby providing greater force by which to break the washer and form the staples. Again, though, the breakable washer may be omitted entirely in some versions.

C. Multi-Cam Member for Oblique Motor

Figure 35:
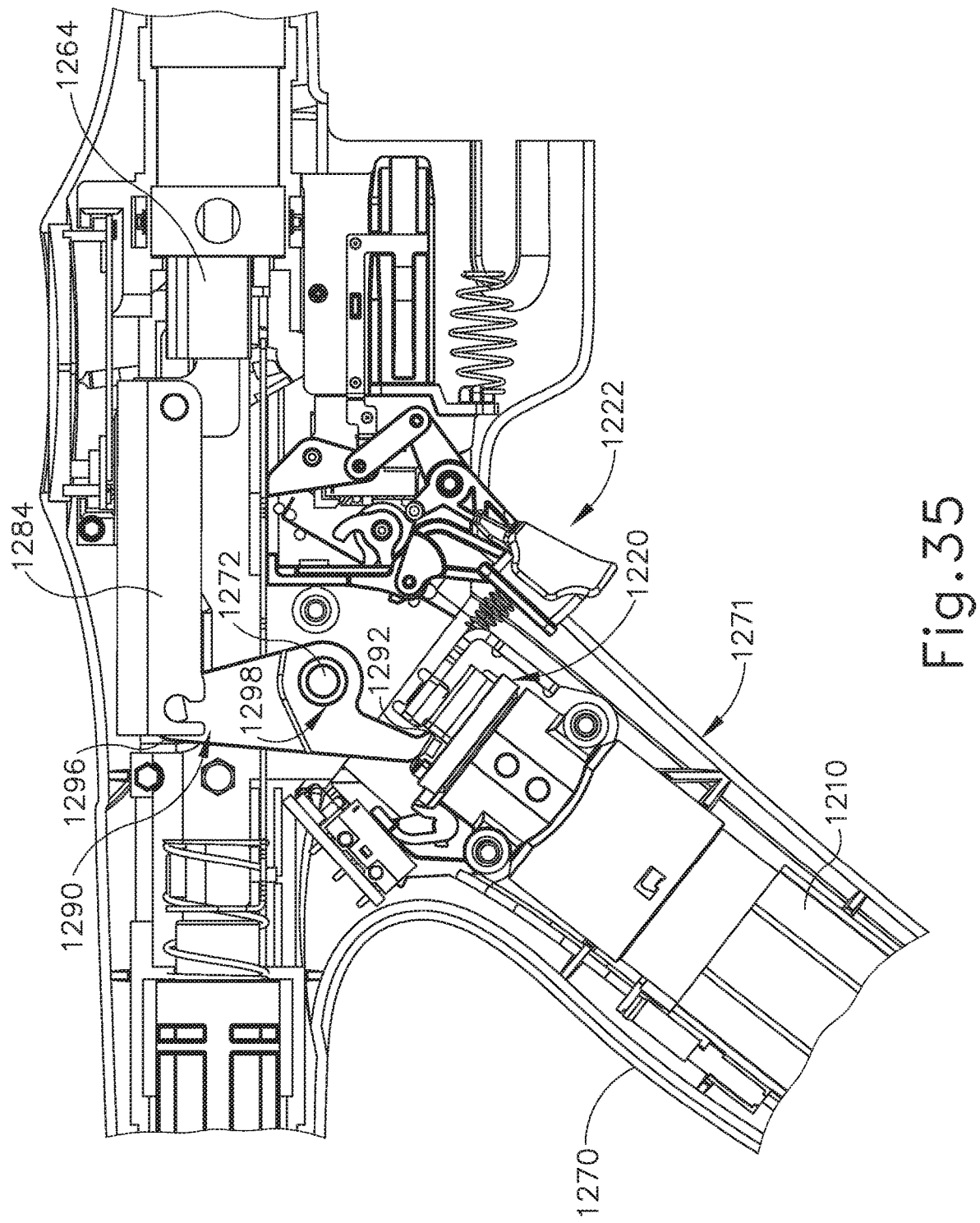
FIG. 35 depicts an enlarged side elevational view of another exemplary multi-cam drive assembly for use in a circular stapling surgical instrument having an obliquely oriented motor.
Figure 36:
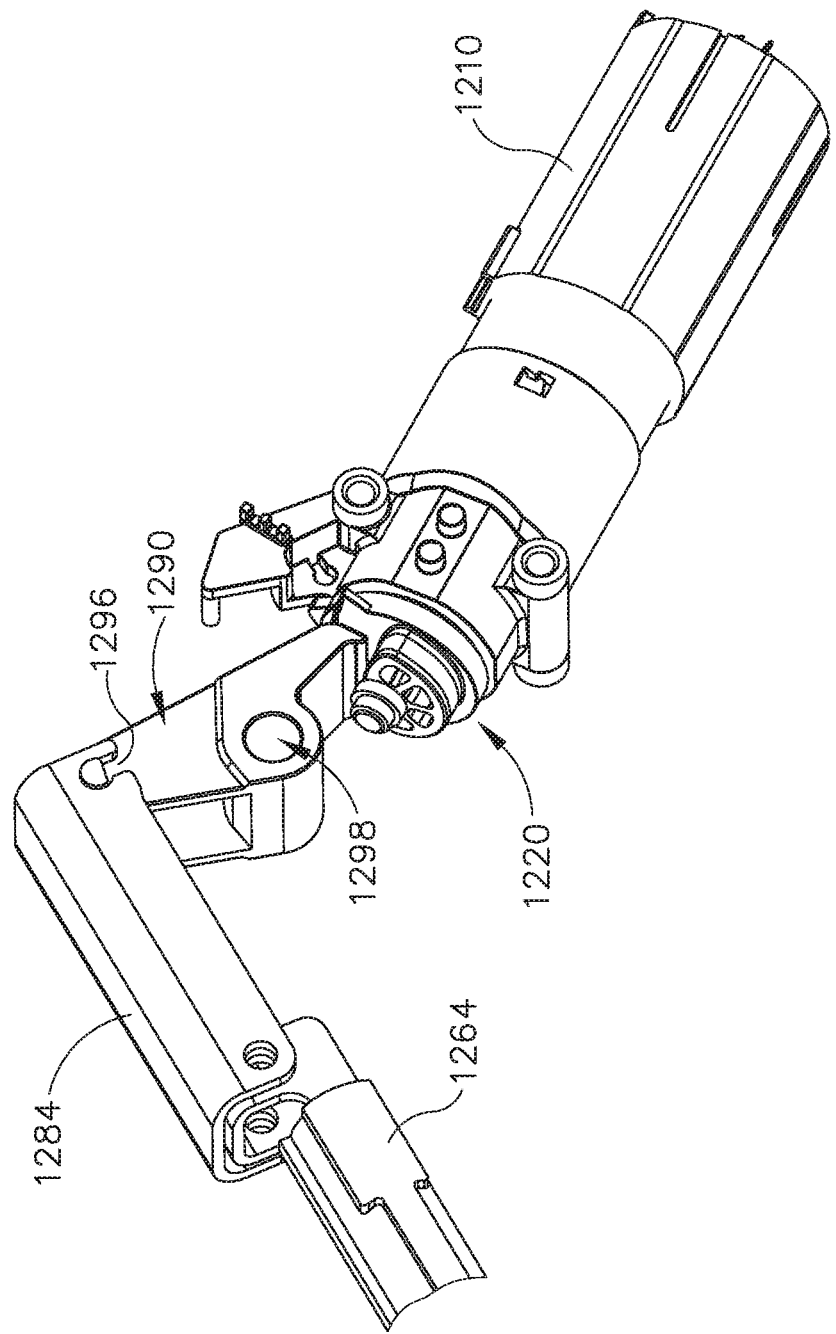
FIG. 36 depicts a perspective view of the multi-cam drive assembly of FIG. 35.

FIG. 35 shows features of yet another exemplary alternative circular surgical stapling instrument, which may also include features that are similar to stapling head assembly (20), anvil (40), knob (98), curved shaft assembly (1006), etc. The instrument of the present example also includes a handle assembly (1270) with an obliquely oriented pistol grip (1271) and a motor (1210) disposed within pistol grip (1271). Motor (1210) and pistol grip (1271) are both oriented obliquely, relative to a longitudinal axis defined by a driver actuator (1264). Driver actuator (1264) translates within the shaft assembly to actuate the stapling head assembly, such that driver actuator (1264) operates similar to driver actuator (64) discussed above. A battery pack (not shown) is integral with handle assembly (1270) to provide power to motor (1210), though it should be understood that motor (1210) may instead be powered by a remote source in some other versions.

A firing trigger and safety trigger assembly (1222) is coupled with the handle assembly, and is operable to selectively activate motor (1210). By way of example only, firing trigger and safety trigger assembly (1222) may be configured in accordance with at least some of the teachings of U.S. patent application Ser. No. 14/033,751, entitled CONTROL FEATURES FOR MOTORIZED SURGICAL STAPLING INSTRUMENT, filed on Sep. 23, 2013, now U.S. Pat. No. 9,907,552, issued on Mar. 6, 2018, the disclosure of which is incorporated by reference herein. The instrument of the present example may also include a start switch and stop switch configured in accordance with at least some of the teachings of U.S. patent application Ser. No. 14/033,751, entitled CONTROL FEATURES FOR MOTORIZED SURGICAL STAPLING INSTRUMENT, filed on Sep. 23, 2013, now U.S. Pat. No. 9,907,552, issued on Mar. 6, 2018, the disclosure of which is incorporated by reference herein. Other suitable variations of a firing trigger and safety trigger assembly (1222), as well as a start and stop switch, will be apparent to those of ordinary skill in the art in view of the teachings herein.

As best seen in FIGS. 35-36 and 41A-41B, motor (1210) is coupled with a multi-cam member (1220), such that activation of motor (1210) will rotate multi-cam member (1220) about an axis that extends longitudinally through the center of motor (1210) and through the center of multi-cam member (1220). Multi-cam member (1220) is engaged with a pivoting cam follower (1290), which is pivotally coupled with handle assembly (1270). In particular, cam follower (1290) includes a pivot opening (1298), in which a pivot pin (1272) is disposed. Cam follower (1290) is thus pivotable about a longitudinal axis defined by pivot pin (1272). Cam follower (1290) is also pivotally coupled with a follower interface feature (1284), which is further coupled with driver actuator (1264). As will be described in further detail below, as multi-cam member (1220) is rotated by motor (1210) through a first range of angular motion, cam follower (1290) will pivot in a first direction (clockwise in the view shown in FIG. 35; counterclockwise in the view shown in FIGS. 41A-41B), thereby driving follower interface feature (1284) and driver actuator (1264) distally. This distal motion will drive a knife and staples through tissue that is captured between the stapling head assembly and anvil, as described above. As multi-cam member (1220) is rotated by motor (1210) through a second range of angular motion, cam follower (1290) will pivot in a second direction (counterclockwise in the view shown in FIG. 35; clockwise in the view shown in FIGS. 41A-41B), thereby driving follower interface feature (1284) and driver actuator (1264) proximally. This proximal motion will retract the knife back into the stapling head assembly.

Figure 37:
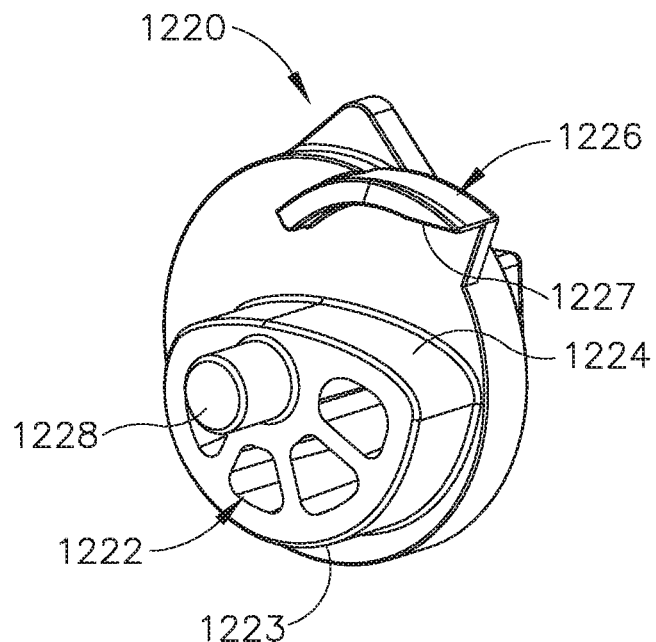
FIG. 37 depicts a perspective view of a cam member of the multi-cam drive assembly of FIG. 35.
Figure 38:
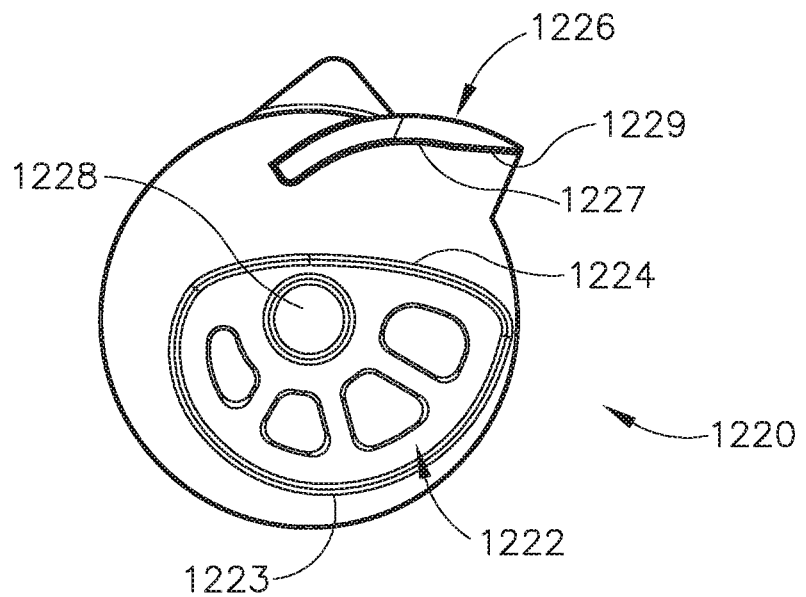
FIG. 38 depicts a front elevational view of the cam member of FIG. 37.

FIGS. 37-38 show multi-cam member (1220) in greater detail. Multi-cam member (1220) includes a first cam feature (1222), a second cam feature (1226), and a distally projecting post (1228). Post (1228) is coaxially aligned with the longitudinal axis of motor (1210). It should be understood that post (1228) may be omitted in some versions, First cam feature (1222) includes a curved cam surface (1223) and a substantially flat cam surface (1224). Curved cam surface (1223) is presented generally radially outwardly. Second cam feature (1226) includes a curved cam surface (1227) with an adjacent, substantially flat lead-in surface (1229). Surfaces (1227, 1229) are presented generally radially inwardly. Curved cam surfaces (1223, 1227) are defined by different radii of curvature extending from different origins. The origin of the radius of curvature for each curved cam surface (1223, 1227) is offset from post (1228).

Figure 39:
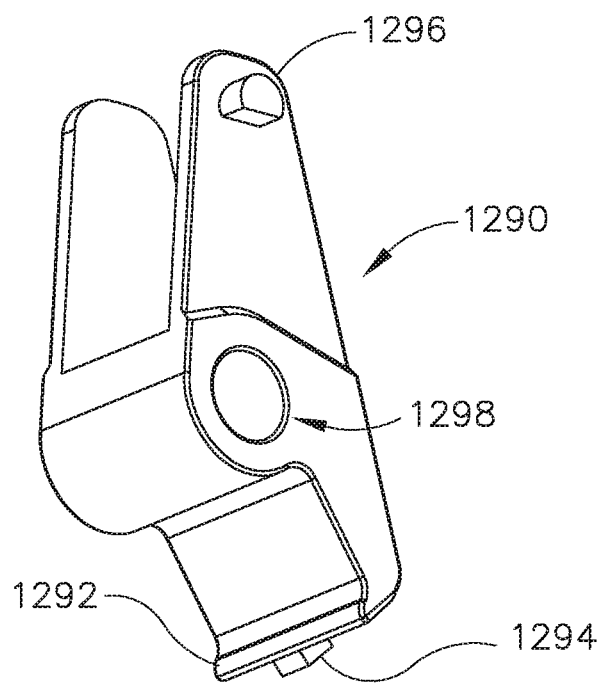
FIG. 39 depicts a perspective view of a cam follower of the multi-cam drive assembly of FIG. 35.
Figure 40:
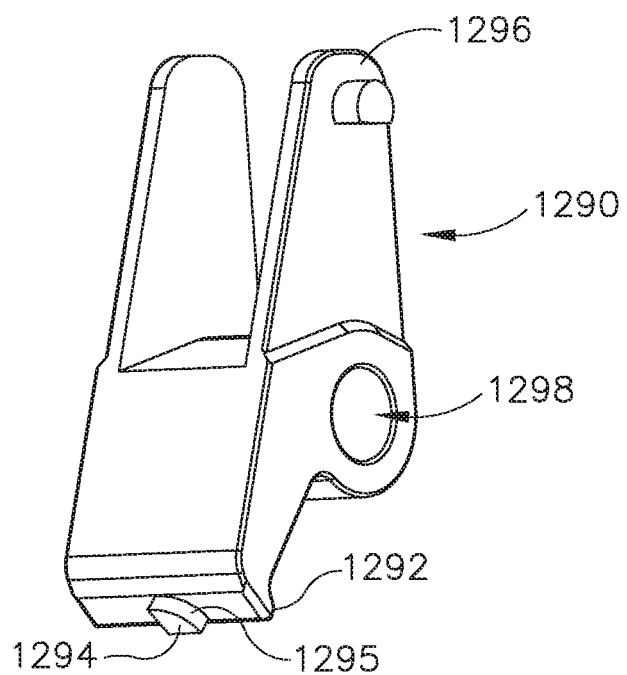
FIG. 40 depicts another perspective view of the cam follower of FIG. 39.

FIGS. 39-40 show cam follower (1290) in greater detail. Cam follower (1290) includes a first projection (1292), a second projection (1294), and a coupling end (1296). Coupling end (1296) is pivotally coupled with follower interface feature (1284). Projections (1292, 1294) are engaged with multi-cam member (1220). In particular, first projection (1292) is configured to engage first cam feature (1222) and second projection (1294) is configured to engage second cam feature (1226). The interaction between projections (1292, 1294) and the corresponding cam features (1222, 1226) provides advancement and retraction of driver actuator (1264), as shown in FIGS. 41A-41B.

Figure 41A:
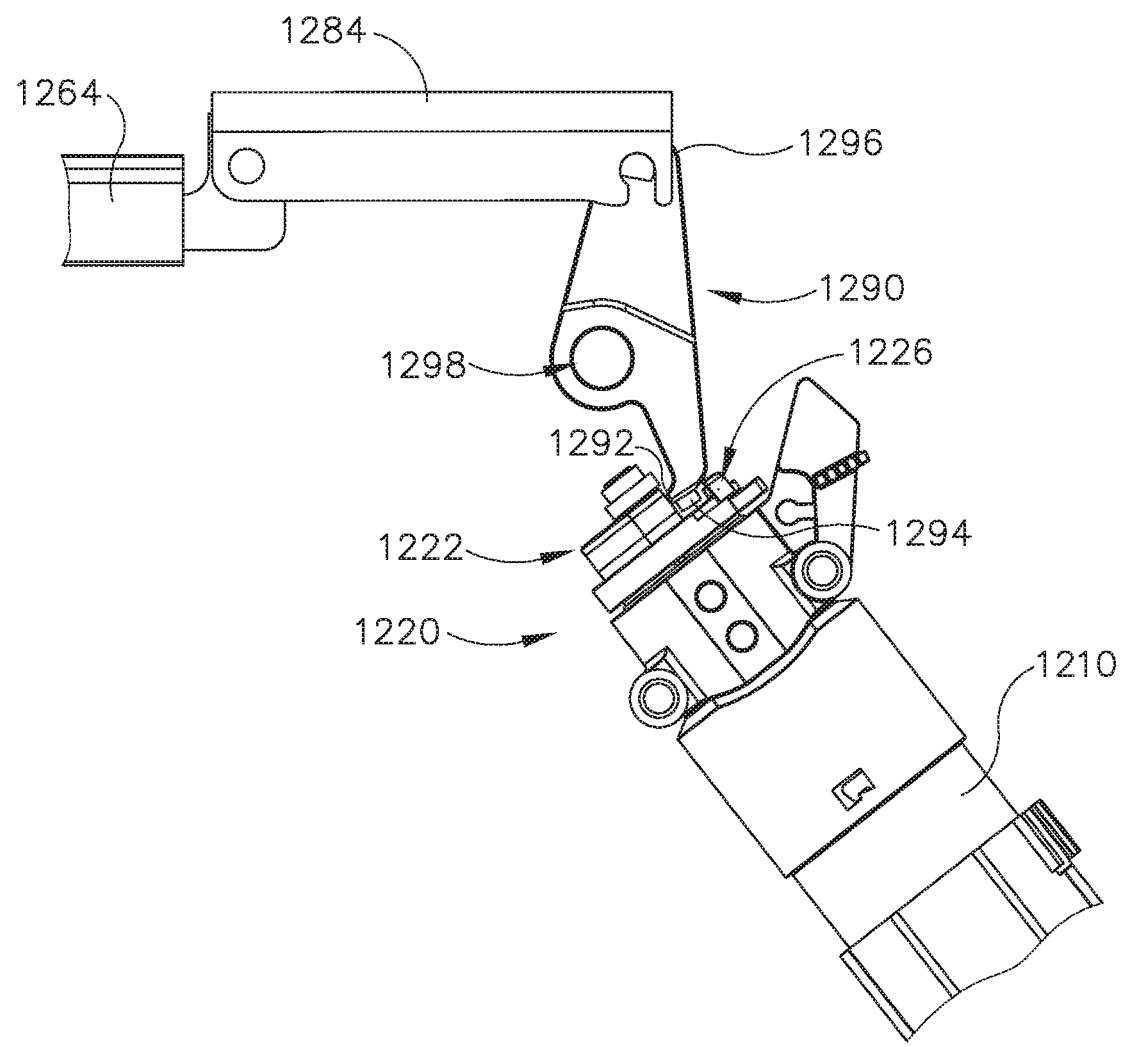
FIG. 41A depicts another enlarged side elevational view of the multi-cam drive assembly of FIG. 35, in a home position.
Figure 41B:
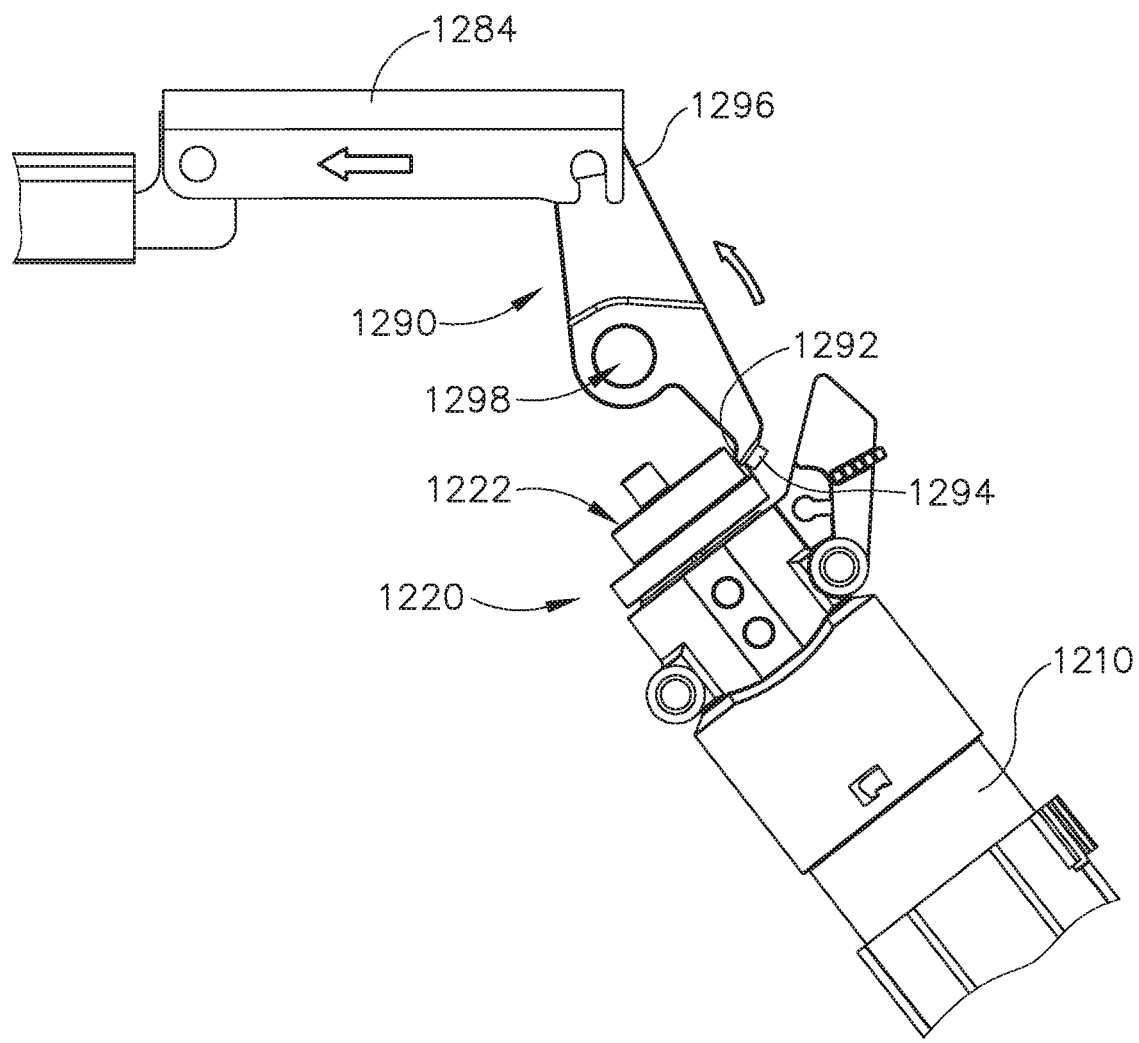
FIG. 41B depicts another enlarged side elevational view of the multi-cam drive assembly of FIG. 35, in a fired position.

FIG. 41A shows multi-cam member (1220) in a home position, with driver actuator (1264) in a proximal position. As motor (1210) is activated to rotate multi-cam member (1220) (e.g., clockwise in the view shown in FIG. 38) through a first range of angular motion, curved cam surface (1223) of first cam feature (1222) bears against first projection (1292). This causes cam follower (1290) to pivot in a first direction (counterclockwise in the view shown in FIGS. 41A-41B), thereby driving follower interface feature (1284) and driver actuator (1264) distally as shown in FIG. 41B. This distal motion will drive a knife and staples through tissue that is captured between the stapling head assembly and the anvil, as described above. As motor (1210) continues to rotate multi-cam member (1220) (e.g., clockwise in the view shown in FIG. 38) through a second range of angular motion, curved cam surface (1227) of second cam feature (1226) bears against second projection (1292). This causes cam follower (1290) to pivot in a second direction (clockwise in the view shown in FIGS. 41A-41B), thereby driving follower interface feature (1284) and driver actuator (1264) proximally back to the home position shown in FIG. 41A. In some other versions, follower interface feature (1284) and driver actuator (1264) are not necessarily driven all the way back to the position shown in FIG. 41A, but are driven back to a position that is proximal to the distal position shown in FIG. 41B. The proximal motion of driver actuator (1264) will retract the knife back into the stapling head assembly. It should be understood that substantially flat surface (1224) provides clearance for first projection (1292) through the second range of angular motion, allowing cam follower (1290) to pivot as second cam feature (1226) pulls follower interface feature (1284) and driver actuator (1264) proximally from a distal position to a proximal position. It should also be understood that lead-in surface (1227) and a curved lead-in (1295) of second projection (1294) may cooperate to facilitate capture of second projection (1294) by second cam feature (1226) as multi-cam member (1220) transitions from the first range of angular motion to the second range of angular motion.

In view of the foregoing, it should be understood that curved cam surface (1223) of first cam feature (1222) drives driver actuator (1264) distally by bearing against first projection (1292) of cam follower (1290), thereby actuating the stapling head assembly; while second cam feature (1226) drives driver actuator (1264) proximally by bearing against second projection (1294) of cam follower (1290). Multi-cam member (1220) is thus operable to advance and retract driver actuator (1264) by rotating through a single revolution. In some other versions, multi-cam member (1220) is operable to advance and retract driver actuator (1264) by rotating through less than a single revolution. In the present example, the first angular range of motion of multi-cam member (1220), associated with advancement of driver actuator (1264), is approximately 270°; while the second angular range of motion of multi-cam member (1220), associated with retraction of driver actuator (1264), is approximately 90°. In some other versions, the first angular range of motion of multi-cam member (1220), associated with advancement of driver actuator (1264), is a first 180°; while the second angular range of motion of multi-cam member (1220), associated with retraction of driver actuator (1264), is a second 180°. Other suitable angular ranges of motion will be apparent to those of ordinary skill in the art in view of the teachings herein. In other words, the allocation of distal motion and proximal motion based on rotation of multi-cam member (1220) may be made in any other suitable fashion. It should also be understood that a full range of distal and proximal travel may be provided by less than 360° of rotation of multi-cam member (1220).

Some versions of the anvil contain a breakable washer that is broken by the knife when the knife completes a full distal range of motion, as discussed above with reference to FIG. 42. It will further be understood that the configuration of curved cam surface (1223) may provide an increasing mechanical advantage as the knife reaches the end of its distal movement, thereby providing greater force by which to break the washer and form the staples. Again, though, the breakable washer may be omitted entirely in some versions.

IV. Miscellaneous

In any of the examples described above, a microcontroller, ASIC, and/or other type of control module may be placed in communication with a power source and motor (210, 310, 410, 510, 610, 710, 810, 910, 1010, 1110, 1210) and may be configured to automatically stop motor (210, 310, 410, 510, 610, 710, 810, 910, 1010, 1110, 1210) thereby providing a way to dynamically brake motor (210, 310, 410, 510, 610, 710, 810, 910, 1010, 1110, 1210) such that motor (210, 310, 410, 510, 610, 710, 810, 910, 1010, 1110, 1210) may be actuated for exactly one rotation of a corresponding drive shaft. By way of example only, such a control module may be in communication with an encoder that is in communication with the drive shaft or some other component that moves in response to activation of motor (210, 310, 410, 510, 610, 710, 810, 910, 1010, 1110, 1210). As another merely illustrative example, such a control module may be in communication with one or more reed switches that are in communication with the drive shaft or some other component that moves in response to activation of motor (210, 310, 410, 510, 610, 710, 810, 910, 1010, 1110, 1210). Other suitable types of sensors and control modules that may be used to provide precise stopping of motor (210, 310, 410, 510, 610, 710, 810, 910, 1010, 1110, 1210) (e.g., based on tracked rotation of a component, based on translation of a component, and/or based on some other parameter, etc.) will be apparent to those of ordinary skill in the art in view of the teachings herein. Of course, a control module may be configured to control motor (210, 310, 410, 510, 610, 710, 810, 910, 1010, 1110, 1210) to activate for any suitable number of rotations, etc. In some instances, controlling the starting and stopping of motor (210, 310, 410, 510, 610, 710, 810, 910, 1010, 1110, 1210) may be performed in accordance with the teachings of U.S. patent application Ser. No. 14/033,751, entitled CONTROL FEATURES FOR MOTORIZED SURGICAL STAPLING INSTRUMENT, filed on Sep. 23, 2013, now U.S. Pat. No. 9,907,552, issued on Mar. 6, 2018, the disclosure of which is incorporated by reference herein.

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. patent application Ser. No. 13/693,430, entitled "Trans-Oral Circular Anvil Introduction System with Dilation Feature," filed Dec. 4, 2012, now U.S. Pat. No. 9,572,573, issued Feb. 21, 2017, the disclosure of which is incorporated by reference herein; U.S. patent application Ser. No. 13/688,951, entitled "Surgical Staple with Integral Pledget for Tip Deflection," filed Nov. 29, 2012, now U.S. Pat. No. 9,289,207, issued Mar. 22, 2016, the disclosure of which is incorporated by reference herein; U.S. patent application Ser. No. 13/706,827, entitled "Surgical Stapler with Varying Staple Widths along Different Circumferences," filed Dec. 6, 2012, now abandoned, the disclosure of which is incorporated by reference herein; U.S. patent application Ser. No. 13/688,992, entitled "Pivoting Anvil for Surgical Circular Stapler," filed Nov. 29, 2012, now U.S. Pat. No. 9,498,222, issued Nov. 22, 2016, the disclosure of which is incorporated by reference herein; U.S. patent application Ser. No. 13/693,455, entitled "Circular Anvil Introduction System with Alignment Feature," filed Dec. 4, 2012, now U.S. Pat. No. 9,724,100, issued Aug. 8, 2017, the disclosure of which is incorporated by reference herein; U.S. patent application Ser. No. 13/716,313, entitled "Circular Stapler with Selectable Motorized and Manual Control, Including a Control Ring," filed Dec. 17, 2012, now U.S. Pat. No. 9,532,783, issued Jan. 3, 2017, the disclosure of which is incorporated by reference herein; U.S. patent application Ser. No. 13/716,318, entitled "Motor Driven Rotary Input Circular Stapler with Modular End Effector," filed Dec. 17, 2012, now U.S. Pat. No. 9,597,081, issued Mar. 21, 2017, the disclosure of which is incorporated by reference herein; and/or U.S. patent application Ser. No. 13/716,323, entitled "Motor Driven Rotary Input Circular Stapler with Lockable Flexible Shaft," filed Dec. 17, 2012, now U.S. Pat. No. 9,463,022, issued Oct. 11, 2016, the disclosure of which is incorporated by reference herein. Various suitable ways in which such teachings may be combined will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, now U.S. Pat. No. 8,453,914, issued Jun. 4, 2013, the disclosure of which is incorporated by reference herein, and/or U.S. Pub. No. 2010/0264193, entitled "Surgical Stapling Instrument with An Articulatable End Effector," published Oct. 21, 2010, now U.S. Pat. No. 8,408,439, issued Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
    (a) a handle assembly;
    (b) a shaft extending distally from the handle assembly, wherein the shaft comprises a proximal end and a distal end;
    (c) a stapling assembly, wherein the stapling assembly is disposed at the distal end of the shaft, wherein the stapling assembly is configured to selectively move from an open position to a closed position, and wherein the stapling assembly is operable to drive a plurality of staples into tissue; and
    (d) a firing assembly, wherein the firing assembly comprises:
        (i) a motor housed within the handle assembly,
        (ii) a first cam member housed within the handle assembly, wherein the first cam member is coupled with the motor, wherein the motor is configured to rotate the first cam member in a first angular direction through a first range of motion and through a second range of motion, and
        (iii) a second cam member housed within the handle assembly, wherein the second cam member is pivotably coupled with the handle assembly, wherein the first cam member is configured to pivot the second cam member in a second angular direction relative to the handle assembly while rotating in the first angular direction, wherein the second cam member is configured to actuate a movable member of the stapling assembly distally to drive the plurality of staples while pivoting in the second angular direction,
    wherein the first cam member is configured to rotate in the first angular direction through the second range of motion to pivot the second cam member in a third angular direction, wherein the second cam member is configured to actuate the movable member of the stapling assembly proximally while pivoting in the third angular direction.

2. The surgical instrument of claim 1, wherein the first range of motion is 270 degrees, wherein the second range of motion of 90 degrees.

3. The surgical instrument of claim 1, wherein the third angular direction is opposite relative to the second angular direction.

4. The surgical instrument of claim 1, wherein the first cam member further comprises a first cam feature and a second cam feature, wherein the first cam feature is configured to contact the second cam member in order to pivot the second cam member in the second angular direction, wherein the second cam feature is configured to contact the second cam member in order to pivot the second cam member in the third angular direction.

5. The surgical instrument of claim 4, wherein the first cam member further comprises a distally projecting post defining an axis, wherein the first cam feature and the second cam feature are configured to rotate in the first angular direction about the axis.

6. The surgical instrument of claim 5, wherein the first cam feature is attached to the distally projecting post, wherein the second cam feature is spaced away from both the first cam feature and the distally projecting post.

7. The surgical instrument of claim 6, wherein the first cam feature comprises a first curved cam surface defined by a first radius of curvature extending from a first origin, wherein the second cam feature comprises a second curved cam surface defined by a second radius of curvature extending from a second origin.

8. The surgical instrument of claim 7, wherein the first origin and the second origin are offset from the axis.

9. The surgical instrument of claim 4, wherein the second cam feature further comprises a flat lead in surface and a curved cam surface, wherein the substantially flat lead in surface is configured to contact the second cam member prior to the curved cam surface.

10. The surgical instrument of claim 1, wherein the firing assembly further comprises a driver actuator coupled with the stapling assembly, wherein the driver actuator comprises a proximal portion defining a longitudinal axis.

11. The surgical instrument of claim 10, wherein the motor is oriented obliquely relative to the longitudinal axis.

12. The surgical instrument of claim 10, wherein the firing assembly further comprises an interface feature coupled with the proximal portion of the driver actuator, wherein the interface feature is further pivotably coupled with the second cam member.

13. The surgical instrument of claim 1, wherein the handle assembly comprises an obliquely oriented pistol grip, wherein the motor is housed within the obliquely oriented pistol grip.

14. The surgical instrument of claim 1, wherein the firing assembly further comprises a firing trigger configured to activate the motor.

15. A surgical instrument, comprising:
(a) a handle assembly;
(b) a shaft extending distally from the handle assembly, wherein the shaft comprises a proximal end and a distal end;
(c) a stapling assembly, wherein the stapling assembly is disposed at the distal end of the shaft, wherein the stapling assembly is configured to selectively move from an open position to a closed position, and wherein the stapling assembly is operable to drive a plurality of staples into tissue; and
(d) a firing assembly, wherein the firing assembly comprises:
(i) a motor housed within the handle assembly,
(ii) a first cam member housed within the handle assembly, wherein the first cam member comprises a first engagement body and a second engagement body, wherein the first cam member is coupled with the motor, wherein the motor is configured to rotate the first cam member in a first angular direction through a first range of motion, and
(iii) a second cam member housed within the handle assembly, wherein the second cam member is pivotably coupled with the handle assembly, wherein the first engagement body of the first cam member is configured to pivot the second cam member in a second angular direction relative to the handle assembly while rotating in the first angular direction, wherein the second engagement body of the first cam member is configured to pivot the second cam member in a third angular direction relative to the handle assembly while rotating in the first angular direction, wherein the second cam member is configured to actuate a movable member of the stapling assembly distally to drive the plurality of staples while pivoting in the second angular direction, wherein the second cam member is configured to actuate the moveable member of the stapling assembly proximally while pivoting in the third angular direction.

16. The surgical instrument of claim 15, wherein the first engagement body and the second engagement body both extend from a common surface.

17. The surgical instrument of claim 15, wherein the first engagement body is coupled to a distally projecting post, wherein the distally projecting post couples the first cam member with the motor.

18. The surgical instrument of claim 15, wherein the second engagement body comprises a curved cam surface.

19. A surgical instrument, comprising:
(a) a handle assembly;
(b) a shaft extending distally from the handle assembly, wherein the shaft comprises a proximal end and a distal end;
(c) a stapling assembly, wherein the stapling assembly is disposed at the distal end of the shaft, wherein the stapling assembly is configured to selectively move from an open position to a closed position, and wherein the stapling assembly is operable to drive a plurality of staples into tissue; and
(d) a firing assembly, wherein the firing assembly comprises:
(i) a motor housed within the handle assembly,
(ii) a first cam member housed within the handle assembly, wherein the first cam member is coupled with the motor, wherein the motor is configured to rotate the first cam member in a first angular direction through a single revolution, and
(iii) a second cam member housed within the handle assembly, wherein the second cam member is pivotably coupled with the handle assembly, wherein the first cam member is configured to pivot the second cam member in a second angular direction and a third angular direction relative to the handle assembly while rotating in the first angular direction through the single revolution, wherein the second cam member is configured to actuate a movable member of the stapling assembly distally to drive the plurality of staples while pivoting in the second angular direction, wherein the second cam member is configured to actuate the movable member of the stapling assembly proximally while pivoting in the third angular direction.

* * * * *